(12) United States Patent
Al Husban et al.

(10) Patent No.: US 10,729,655 B2
(45) Date of Patent: Aug. 4, 2020

(54) ORALLY DISINTEGRATING TABLETS

(71) Applicant: AstraZeneca AB, Södertälje (SE)

(72) Inventors: Farhan Abdel Karim Mohammad Al Husban, Cambridge (GB); Lars Håkan Christer Glad, Södertälje (SE); Jenny Malin Christina Hallstein, Södertälje (SE); Andrea Jane Moir, Cambridge (GB); Michael Peter Thompson, Cambridge (GB)

(73) Assignee: AstraZeneca AB, Södertälje (SE)

( * ) Notice: Subject to any disclaimer, the term of this patent is extended or adjusted under 35 U.S.C. 154(b) by 0 days.

(21) Appl. No.: 16/095,090

(22) PCT Filed: Apr. 20, 2017

(86) PCT No.: PCT/EP2017/059443
§ 371 (c)(1),
(2) Date: Oct. 19, 2018

(87) PCT Pub. No.: WO2017/182589
PCT Pub. Date: Oct. 26, 2017

(65) Prior Publication Data
US 2019/0117577 A1    Apr. 25, 2019

Related U.S. Application Data

(60) Provisional application No. 62/325,584, filed on Apr. 21, 2016.

(51) Int. Cl.
| A61K 31/519 | (2006.01) |
| A61K 9/20 | (2006.01) |
| A61J 1/03 | (2006.01) |
| B65D 75/32 | (2006.01) |
| A61K 9/00 | (2006.01) |
| A61J 3/10 | (2006.01) |

(52) U.S. Cl.
CPC ............ *A61K 9/2018* (2013.01); *A61J 1/035* (2013.01); *A61J 3/10* (2013.01); *A61K 9/0056* (2013.01); *A61K 9/2009* (2013.01); *A61K 9/2013* (2013.01); *A61K 9/2027* (2013.01); *A61K 9/2054* (2013.01); *A61K 9/2095* (2013.01); *A61K 31/519* (2013.01); *B65D 75/327* (2013.01)

(58) Field of Classification Search
CPC ........................... A61K 31/519; C07D 487/04
USPC ........................................ 514/261.1; 544/254
See application file for complete search history.

(56) References Cited

U.S. PATENT DOCUMENTS

| 7,390,503 B1 | 6/2008 | Ahmed et al. |
| 2013/0160408 A1 | 7/2013 | Neff |
| 2015/0044286 A1 | 2/2015 | Yoshida et al. |

FOREIGN PATENT DOCUMENTS

| CN | 2717851 Y | 8/2005 |
| CN | 101505754 A | 8/2009 |
| CN | 102058889 A | 5/2011 |
| CN | 104650091 A | 5/2015 |
| EP | 1289992 B1 | 3/2006 |
| WO | 2008-024045 A1 | 2/2008 |
| WO | 2015/110952 A1 | 7/2015 |

OTHER PUBLICATIONS

Badimon, et. al., European Heart Journal (2004) 25, 1197-1207.*
Written Opinion and International Search Report for PCT/EP2017/059443 dated Feb. 22, 2018.
Krupa, et al., The Influence of the API Properties on the ODTs Manufacturing from Co-processed Excipient Systems, AAPS ParmSciTech, 2012, 13:4, pp. 1120-1129.
Rowe, et al., Handbook of Pharmaceutical Excipients, Pharmaceutical Press and American Pharmacists Assoc., 2006, 5$^{th}$ edition, pp. 93-95, pp. 132-135, pp. 188-191, pp. 214-216, pp. 336-340, pp. 449-453 and pp. 705-707.
Pre-Grant Opposition dated Oct. 29, 2018, against Indian Patent Application No. 201817040637.
European Medicines Agency, "Brilique: European Public Assessment Report (EPAR)—Product Information" (last updated Oct. 16, 2019) https://www.ema.europa.eu/en/documents/product-information/brilique-epar-product-information_en.pdf).
Third Party Observation submitted Oct. 23, 2019, in counterpart European Application No. EP20170720055.
Brniak et al., Evaluation of co-processed excipients used for direct compression of orally disintegrating tablets (ODT) using novel disintegration apparatus, *Pharmaceutical Development and Technology* 2013, 18:2, pp. 464-474.
Chaudhary et al., Excipients Updates for Orally Disintegrating Dosage Forms, *Int. J. Res. Pharm. Sci.* 2010, 1:2, pp. 103-107.
Pabari RM, et al., Effect of a Disintegration Mechanism on Wetting, Water Absorption, and Disintegration Time of Orodispersible Tablets, *J. Young Pharmacists* 2012, vol. 4, pp. 157-163.
Pilchik, Pharmaceutical Blister Packaging, Part I (Rationale and Materials), *Pharmaceutical Technology* Nov. 2000, pp. 68, 70, 72, 74, 76, and 78.
Pilchik, Pharmaceutical Blister Packaging, Part II (Machinery and Assembly), *Pharmaceutical Technology* Dec. 2000, pp. 56, 58, and 60.
U.S. Dept. of Health and Human Services FDA Center for Drug Evaluation and Research (CDER), *Guidance for Industry Orally Disintegrating Tablets* 2008, pp. 1-3 (6 pages total).
European Pharmacopoeia, Eighth Edition. vol. 1, Directorate for the Quality of the Medicines & HealthCare of the Council of Europe (EDQM), Jan. 2014, pp. 809-811.
Ohrem, et al., Why is mannitol becoming more and more popular as a pharmaceutical excipient in solid dosage forms?, *Pharmaceutical Development and Technology*, Mar. 2013, 19:3, pp. 257-262.
Fuji Chemical Industries, F-Melt®-Fast Melt Tablets Made Easy!, 2015, 20 pgs.
Rowe, et al., Handbook of Pharmaceutical Excipients, Sixth Edition, 2009, pp. 185-186.

* cited by examiner

*Primary Examiner* — Jeffrey H Murray

(57) ABSTRACT

The present invention relates to rapidly disintegrating oral dosage forms, more particularly to rapidly disintegrating tablets containing (1S,2S,3R,5S)-3-[7-{[1R,2S)-2-(3,4-difluorophenyl)cyclopropyl]amino}-5-(propylthio)-3H-[1,2,3]-triazolo[4,5-d]pyrimidin-3-yl]-5 5-(2-hydroxyethoxy)cyclopentane-1,2-diol and a disintegrating excipient. Blister packs suitable for use with the rapidly disintegrating oral dosage form are also disclosed.

28 Claims, 9 Drawing Sheets

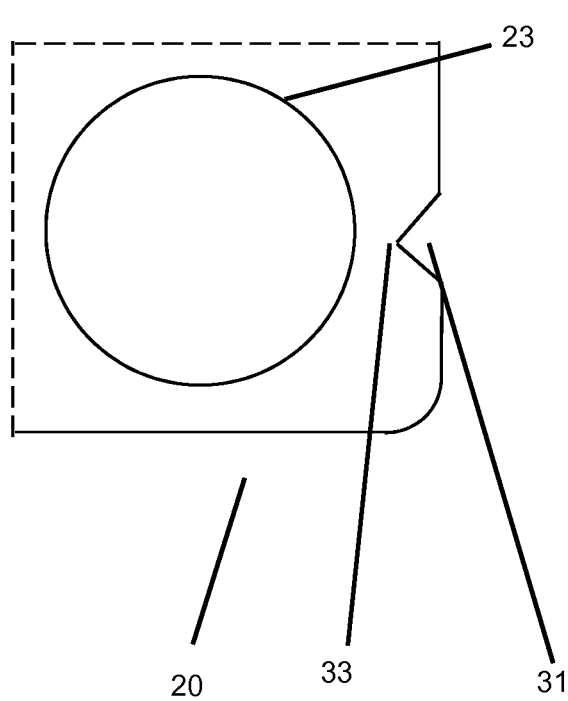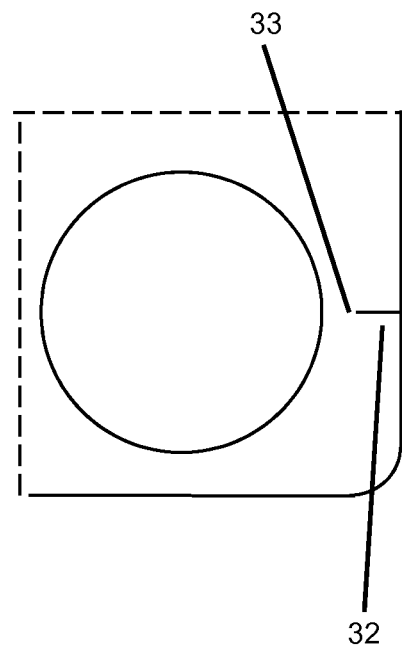
Fig 3A                    Fig 3B

ORALLY DISINTEGRATING TABLETS

CROSS-REFERENCE TO RELATED APPLICATIONS

This application is a U.S. National Stage application of International Application No. PCT/EP2017/059443, filed on Apr. 20, 2017, which claims the benefit under 35 U.S.C. § 119(e) of the U.S. Provisional Application No. 62/325,584, filed on Apr. 21, 2016. Each of the above listed applications is incorporated by reference herein in its entirety for all purposes.

FIELD OF THE INVENTION

The present invention relates to rapidly disintegrating oral dosage forms in the form of tablets, particularly tablets containing the compound of formula I:

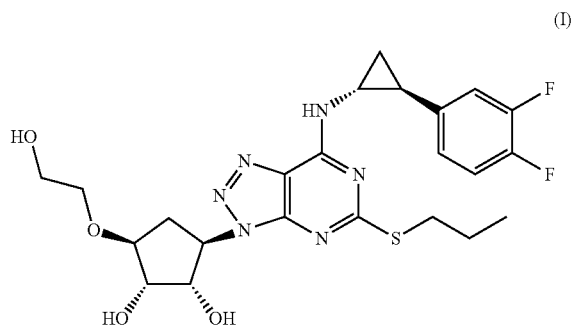 [SMILES: CCCSc1nc(N[C@@H]2C[C@H]2c2ccc(F)c(F)c2)c2nnn([C@@H]3C[C@H](OCCO)[C@@H](O)[C@H]3O)c2n1]

(I)

The compound of formula (I) is conventionally named (1S,2S,3R,5S)-3-[7-{[(1R,2S)-2-(3,4-difluorophenyl)cyclopropyl]amino}-5-(propylthio)-3H[1,2,3]-triazolo[4,5-d]pyrimidin-3-yl]-5-(2-hydroxyethoxy)cyclopentane-1,2-diol and hereinafter will be referred to as ticagrelor.

BACKGROUND OF THE INVENTION

Ticagrelor is the active ingredient in the drug product known as BRILINTA® (or BRILIQUE in Europe) which has been approved for use in multiple jurisdictions including the USA and Europe. Ticagrelor is disclosed as an ADP-receptor antagonist in International Patent Application number PCT/SE99/02256 (publication number WO 00/34283). The discovery of ticagrelor is discussed in Humphries B., et al., "'Daring to be Different': the Discovery of Ticagrelor", The Handbook of Medicinal Chemistry, Principles and Practice, 2015, The Royal Society of Chemistry, UK; and Springthorpe B., et al., *Biorg. Med. Chem. Lett.* 17 (2007) 6013-6018.

BRILINTA® is currently marketed in the form of 60 mg and 90 mg immediate release tablets. International Patent Application number PCT/SE2007/000736 (publication number WO 2008/024045) discloses certain pharmaceutical formulations containing ticagrelor for oral administration.

A significant proportion of patients with stroke have difficulty swallowing (dysphagia) in the acute phase, and many have ongoing problems. This potentially can lead to a reduction in patient compliance when such patients are administered oral formulations that must be swallowed intact. Other patients may also suffer from dysphagia as it is common among all age groups and is observed in about 35% of the general population, as well as up to 60% of the elderly institutionalized population and about 20% of all patients in long-term care facilities.

The present invention relates to alternative ticagrelor dosage forms that can be administered, for example, to such patients. These dosage forms are rapidly disintegrating oral dosage forms containing ticagrelor, including such dosage forms that produce a ticagrelor bioavailability substantially comparable to the currently marketed 60 mg or 90 mg immediate release dosage forms.

The listing or discussion of a prior-published document in this specification should not necessarily be taken as an acknowledgement that the document is part of the state of the art or is common general knowledge.

DISCLOSURE OF THE INVENTION

According to a first aspect of the invention there is provided a tablet comprising:
  (1S,2S,3R,5S)-3-[7-{[(1R,2S)-2-(3,4-difluorophenyl)cyclopropyl]amino}-5-(propylthio)-3H-[1,2,3]-triazolo[4,5-d]pyrimidin-3-yl]-5-(2-hydroxyethoxy)cyclo-pentane-1,2-diol; and
  at least one disintegrating excipient;
wherein the tablet has a hardness of from about 50 to about 150N and a disintegration time of less than about 3 minutes. Such compositions are referred to hereinafter as "the tablets of the invention".

The tablets of the present invention are pharmaceutical formulations that rapidly disintegrate in the mouth. In one embodiment the tablets of the invention have a disintegration time of less than about 2 minutes, or preferably less than about 1 minute. In a particular embodiment, the tablets of the invention have a disintegration time of less than about 60, 55, 50, 45, 40, 35 or 30 seconds. The rapid disintegration in the mouth makes it possible in particular for a patient to be administered ticagrelor without having to simultaneously drink liquid in order to ingest the formulation. Additionally, the rapid disintegration allows the ticagrelor to be more easily taken into the body by patients and in particular paediatric and elderly patients as well as other patients that may have difficulty swallowing (e.g. patients that have suffered a stroke).

Disintegration time may be measured in accordance with the method set out in US Pharmacopoeia (USP) monograph 701. This method acts as a model for oral disintegration and allows the determination of an in vitro disintegration time which may be used as a guide to understanding the rate of disintegration in the oral cavity.

Formulations which disintegrate within 3 minutes when tested under this method may be considered to be "orodispersible" in accordance with the European Pharmacopoeia (8$^{th}$ ed.). The US-FDA Guidelines recommend that the term "orally disintegrating tablet" be associated with solid oral preparations that disintegrate rapidly in the oral cavity, with an in vitro disintegration time of approximately 30 seconds or less when tested under this method. The tablets of the present invention may therefore be considered to be orodispersible tablets, or orally disintegrating tablets.

The tablets of the present invention are also suitable for nasogastric delivery to a patient. Nasogastric delivery requires that the constituents of the tablet be suspendable or soluble in water so that the tablet contents may be administered to the patient through a nasogastric tube.

It is also important that orally disintegrating formulations maintain an acceptable rate of disintegration following storage. Disintegration time for tablets may be detrimentally affected by a number of factors, including exposure to gases, moisture, and light. It is important to minimise changes in the formulation during storage which may increase aggregation of particles of the ticagrelor during disintegration as this slows down the dissolution of the ticagrelor in the oral cavity. Tablets may be administered to patients many months following their initial preparation, and the tablets of the invention have been found to maintain an acceptable disintegration time following storage.

In a preferred embodiment, the tablet has a disintegration time of less than 3 minutes (preferably less than 60 seconds) following storage for at least 1 month. Particular storage conditions that may be mentioned in this respect include storage at 25° C. and 60% relative humidity. In other embodiments, the tablet has a disintegration time of less than 3 minutes (preferably less than 60 seconds) following storage for longer periods (e.g. for 3, 6 or 12 months), and/or under harsher conditions (e.g. 40° C. and 75% relative humidity). Tablets which are stored in sealed containers, such as the blister packs described herein are also shown to maintain a disintegration time of less than 3 minutes, and even less than 60 seconds, following storage for up to 12 months.

An increase in the disintegration rate in the mouth facilitates administration to certain patients. Examples of tablets which are considered to be rapidly disintegrating are described in U.S. Pat. No. 3,885,026 and US patent publication number US 2013/280327.

It is important that the tablets of the invention exhibit rapid dispersion of the ticagrelor (e.g. in the form of granules) in physiological solutions (e.g. saliva). This rapid dispersion facilitates the swallowing of the drug by the patient. The dissolution rate of the ticagrelor should also be maintained within acceptable parameters. Tablets are typically considered to have a suitable dissolution profile if they comply with the requirement: Q=70% after 45 minutes. Suitable conditions for such measurements according to the Ph Eur include Apparatus 2, 75 rpm, 90 mL, 0.2% (w/v) Tween 80. In a further embodiment, the dissolution profile of the tablet of the invention is such that Q=70% after 45 minutes.

One of the qualities that is desirable in a rapidly disintegrating oral dosage form is bioavailability of the ticagrelor. The bioavailability of a drug is the amount of an administered dose that reaches the systemic circulation in an unchanged form. Therefore, sufficient bioavailability is important to achieve a therapeutically active concentration at the site of action. Both drug release from the formulation and the stability of the formulation will affect its bioavailability. It is therefore important that the drug formulation should rapidly release a sufficient quantity of the drug. In vitro drug release can be measured using tests known in the art, for example using a standard United States Pharmacopoeia (USP) dissolution apparatus and a standard 'biorelevant' dissolution medium, for example FaSSIF (Galia, E., et al., *Pharm. Res.* 1998, 15 (5), 698-705). These tests can provide some understanding of the likely formulation performance in vivo.

The tablets of the invention contain at least one disintegrating excipient. Said disintegrating excipient may be a single substance or it may be a mixture of substances (referred to herein as a disintegrating excipient pre-mix) wherein said mixture of substances functions as a disintegrant. In one embodiment, the disintegrating excipient is a fast oral disintegrating excipient. The use of a fast oral disintegrating excipient increases the rate of disintegration of the oral dosage form. Fast oral disintegrating excipients are excipients which are suitable for use in pharmaceutical and/or nutraceutical formulations and which enable the manufacture of tablets which have an oral disintegrating time of less than 3 minutes. It is preferred that the disintegrating excipients referred to in the embodiments disclosed herein are disintegrating excipient pre-mixes.

Disintegrants that are suitable for use as disintegrating excipients in the tablets of the present invention include, but are not limited to, low-substituted hydroxypropyl cellulose, and, particularly, crospovidone, microcrystalline cellulose, croscarmellose sodium, sodium starch glycolate, and mixtures thereof. Commercially available disintegrating excipient pre-mixes such as F-melt type C, F-melt type M, Ludiflash, GalenIQ, Prosolv and Pharmaburst may also be used in the tablets of the present invention.

F-melt type C, F-melt type M, Ludiflash, GalenIQ, Prosolv and Pharmaburst are examples of fast oral disintegrating excipients. F-melt (Fuji Chemicals) may be supplied as F-melt type C or F-melt type M. F-melt type C is a formulation consisting of mannitol (65%), xylitol (5%), anhydrous dibasic calcium phosphate (4%), crospovidone (8%) and microcrystalline cellulose (18%). F-melt type C is formed by a co-spray drying of the above ingredients. F-melt type M is a formulation consisting of mannitol, xylitol, magnesium aluminometasilicate, crospovidone and microcrystalline cellulose. Ludiflash (BASF Fine Chemicals) is a formulation consisting of mannitol (90%), crospovidone (Kollidon CL-SF) (5%) and polyvinyl acetate (Kollicoat SR 30D) (5%). GalenIQ (Grade 721; Beneo-Palatinit) is a formulation comprising a disaccharide alcohol in a 3:1 ratio of 6-O-α-D-glucopyranosyl-D-sorbitol and 1-O-α-D-glucopyranosyl-D-mannitol dihydrate. Prosolv ODT G2 (JRS Pharma) is a formulation comprising microcrystalline cellulose, colloidal silicon dioxide, mannitol, fructose and crospovidone. Pharmaburst (SPI Pharma) is a formulation comprising mannitol, sorbitol, crospovidone, croscarmellose sodium and colloidal silicon dioxide.

In an embodiment of the invention, the excipient is selected from the group consisting of F-melt type C, F-melt type M, Ludiflash, GalenIQ, Prosolv and Pharmaburst. F-melt type C and F-melt type M are particularly preferred as they have been found to be superior in terms of manufacturability with good flow and no sticking or picking on tablet punches in combination with an acceptable disintegration time when compared to tablets containing Prosolv and Pharmaburst.

A number of disintegrating excipient pre-mixes, including many of the commercially available fast oral disintegrating excipients, contain at least one carbohydrate filler and at least one disintegrant. In this context, the term "carbohydrate" includes sugars (e.g. monosaccharides, disaccharides and oligosaccharides, such as maltose and dextrin) as well as derivatives thereof (e.g. polyhydric alcohol derivatives, such as mannitol, xylitol and sorbitol). Particular carbohydrate fillers that may be mentioned in this respect include maltose, dextrin, mannitol, xylitol, sorbitol, and mixtures thereof. Mannitol is the most preferred carbohydrate filler, though other fillers (including non-carbohydrate fillers) may be present in the tablets of the invention. These materials exhibit a number of properties which make them particularly suitable for use in the tablets of the invention, including allowing rapid dissolution, smooth mouth feeling, and excellent compressibility for the final tablet. In one embodiment of the invention, the at least one disintegrating excipient comprises mannitol. Disintegrants that are typically useful in disintegrating excipients and the tablets of the invention include low-substituted hydroxypropyl cellulose, and, particularly, crospovidone, microcrystalline cellulose, croscarmellose sodium, sodium starch glycolate, and mixtures thereof. Crospovidone is particularly preferred in this respect. Thus, in a further embodiment, the at least one disintegrating excipient comprises crospovidone.

F-melt type C is the most preferred disintegrating excipient for use in the tablets of the invention. Thus, in one embodiment the at least one disintegrating excipient is a disintegrating excipient pre-mix comprising mannitol, xylitol, anhydrous dibasic calcium phosphate, crospovidone and microcrystalline cellulose. In a further embodiment, the at least one disintegrating excipient pre-mix comprises F-melt type C.

The tablets of the invention should contain a sufficient amount of the at least one disintegrating excipient in order for the tablet to disintegrate within a sufficiently short time. However, the amount of the at least one disintegrating excipient must not be so high as to cause difficulties in the manufacture of the tablet in view of the adhesiveness and/or cohesiveness of ticagrelor. It has been surprisingly found that tablets of the invention in which the at least one disintegrating excipient is a disintegrating excipient pre-mix that is present in an amount ranging from about 50% to about 80% by weight of the tablet have an acceptable disintegration time (e.g. less than 3 minutes) while simultaneously allowing the adhesiveness and/or cohesiveness of ticagrelor to be adequately countered during the manufacture of the tablets. Thus, in a further embodiment, the at least one disintegrating excipient is a disintegrating excipient pre-mix present in an amount ranging from about 50% to about 80% by weight of the tablet. As is discussed hereinbefore, it is particularly preferred that the at least one disintegrating excipient is a fast oral disintegrating excipient such as F-melt type C, however only a portion of the disintegrant may be a substance that is typically classified as a disintegrant. In the case of the formulation described in Example 7, the total amount of disintegrant (i.e. crospovidone and microcrystalline cellulose) in the tablet is about 19% by weight of the tablet. Nevertheless, the disintegrating excipient (i.e. F-melt type C) is a mixture comprising mannitol and other fillers, and this disintegrating excipient is present in about 64.8% by weight of the tablet. Thus, for the avoidance of doubt, the above-mentioned embodiment includes examples in which the tablet comprises fast oral disintegrating excipient (e.g. F-melt type C) in an amount ranging from about 50% to about 80% by weight of the tablet.

In a further embodiment, the tablet contains at least one disintegrant (e.g. as a component of the at least one disintegrating excipient) in a total amount of at least about 10% by weight of the tablet, such as from about 10 to about 30% by weight of the tablet.

Non-carbohydrate fillers which may be present in the tablets of the invention include dibasic calcium phosphate dehydrate or tribasic calcium phosphate, or particularly anhydrous dibasic calcium phosphate or magnesium aluminometasilicate, or mixtures of any of the foregoing. In a preferred embodiment, the tablet of the invention contains anhydrous dibasic calcium phosphate.

It will be appreciated that a particular excipient may act as both a binder and a filler, or as a binder, a filler and a disintegrant. Typically the combined amount of filler, binder and disintegrant comprises, for example, from 50 to 90%, e.g. from 70 to 85%, by weight of the tablet.

The tablets of the invention contain ticagrelor, (1S,2S,3R, 5S)-3-[7-{[(1R,2S)-2-(3,4-difluorophenyl)cyclopropyl] amino}-5-(propylthio)-3H-[1,2,3]-triazolo[4,5-d]pyrimidin-3-yl]-5-(2-hydroxyethoxy)cyclopentane-1,2-diol. Ticagrelor has surprisingly been found to exhibit a high degree of adhesiveness and cohesiveness. These properties cause sticking and picking of the composition during tableting which is undesirable as it leads to poor tablet weight uniformity as well as unacceptable tablet appearance. The adhesiveness and/or cohesiveness also causes other difficulties associated with manufacture of the product.

In one embodiment of the invention, the ticagrelor is present in an amount of from about 10 to about 18% by weight of the tablet. Preferably the ticagrelor is present in an amount of from about 12 to about 17% by weight of the tablet. In a further embodiment, the tablet comprises about 60 mg or about 90 mg of the ticagrelor. When used in this context, the term "about" encompasses variants ranging from 90% to 110% of the absolute amount of ticagrelor. That is, "about 60 mg" refers to a range of from 54 to 66 mg of ticagrelor, and "about 90 mg" refers to a range of from 81 to 99 mg of ticagrelor. In a preferred embodiment, the tablet comprises from 57 to 63 mg or from 85 to 95 mg of ticagrelor. Tablets which comprise about 90 mg of ticagrelor are particularly preferred.

The tablets of the invention have a disintegration time of less than about 3 minutes. In order to achieve this, various aspects of the tablet composition and its method of manufacture must be controlled, including the compression forces used in the tableting step. The compression forces used in the tableting step for the tablets of the invention are typically less than those used to form conventional oral tablets, and the tablets of the invention typically have a lower hardness as a result. This in turn allows the tablet to disintegrate more rapidly in the mouth and thereby facilitate dissolution of the ticagrelor. The tablet of the invention has a hardness of from about 50 to about 150N. In one embodiment, the tablet has a hardness of from about 50 to about 130N, e.g. from about 50 to about 120N, or preferably from about 50 to about 100N. In a more preferred embodiment, the tablet of the invention has a hardness of from about 55 to about 90N. The relatively low hardness that of these tablets renders them prone to breakage when they are removed from conventional push-through blister packs. Thus, the tablets of the invention are particularly suited for use in the blister packs of the eighth aspect of the invention, as are described hereinafter.

Tablets of the invention may comprise at least one anti-caking agent. For tablets which are prepared by a process which comprises a granulation step (e.g. a wet granulation step as described herein), said at least one anti-caking agent may be provided as one of the ingredients in the granulation step (i.e. as an intra-granular anti-caking agent). Alternatively, or additionally, said at least one anti-caking agent or a glidant may be added to the product obtained from the granulation step (i.e. as an extra-granular anti-caking agent or glidant). In preferred embodiments of the invention which involve a tablet obtainable by a process comprising granulation, at least one anti-caking agent may be included as both one or more intra-granular and one or more extra-granular anti-caking agents. For the avoidance of doubt, said intra-granular and extra-granular anti-caking agents may be the same or different. Furthermore, a substance may be chosen which has the properties of both an anti-caking agent and a glidant, e.g. colloidal anhydrous silica.

The anti-caking agent is typically added in order to counter the adhesiveness and/or cohesiveness of the ticagrelor. In a preferred embodiment of the invention, the at least one anti-caking agent is present in an amount of from about 0.5 to about 1% by weight of the tablet.

In one embodiment, the tablets of the invention comprise one or more lubricants. In another embodiment, the tablets of the invention comprises one lubricant.

Other suitable lubricants and additional excipients which may be used are described in Handbook of Pharmaceutical Excipients, 2$^{nd}$ Edition, American Pharmaceutical Association; The Theory and Practice of Industrial Pharmacy, 2$^{nd}$ Edition, Lachman, Leon, 1976; Pharmaceutical Dosage Forms: Tablets Volume 1, 2$^{nd}$ Edition, Lieberman, Hebert A., et al, 1989; Modern Pharmaceutics, Banker, Gilbert and Rhodes, Christopher T, 1979; and Remington's Pharmaceutical Sciences, 15th Edition, 1975.

Suitable lubricants include, for example, magnesium stearate, stearic acid, palmitic acid, calcium stearate, carnauba wax, hydrogenated vegetable oils, mineral oil, polyethylene glycols and sodium stearyl fumarate.

In one embodiment, the lubricant is selected from magnesium stearate and sodium stearyl fumarate. In another embodiment, the lubricant is sodium stearyl fumarate.

Use of an increased amount of lubricant in the tablets was found to improve the flowability of the powder during tableting, and to increase the disintegration time of the tablet. In embodiments of tablets of the invention which contain a lubricant, the lubricant is present in an amount of from about 1 to about 3% by weight of the tablet. In another embodiment, the lubricant is present in an amount of from about 1 to about 2% by weight. The use of a lubricant in this amount was found to provide a tablet with acceptable quality levels while maintaining an acceptable disintegration time.

Additional conventional excipients which may be added include preservatives, stabilisers and/or anti-oxidants. In a preferred embodiment, the tablet of the invention comprises no preservatives, stabilisers or anti-oxidants. In a further preferred embodiment, the tablet consists essentially of the ingredients listed in Example 7. The proportions for any of the ingredients indicated in Example 7 may be altered in line with the proportions described elsewhere here.

In one embodiment of the invention, the tablet comprises ticagrelor, hydroxypropyl cellulose, colloidal anhydrous silica, mannitol, xylitol, anhydrous dibasic calcium phosphate, microcrystalline cellulose, crospovidone, and sodium stearyl fumarate.

In a preferred embodiment of the invention, the tablet consists essentially of ticagrelor, hydroxypropyl cellulose, colloidal anhydrous silica, mannitol, xylitol, anhydrous dibasic calcium phosphate, microcrystalline cellulose, crospovidone, and sodium stearyl fumarate.

In another embodiment of the invention, the tablet comprises:
  ticagrelor at from about 10 to about 18% by weight of the tablet;
  hydroxypropyl cellulose at from about 0.9 to about 2% by weight of the tablet;
  colloidal anhydrous silica at from about 0.5 to about 1% by weight of the tablet;
  mannitol at from about 47 to about 67% by weight of the tablet;
  xylitol at from about 2.5 to about 4% by weight of the tablet;
  anhydrous dibasic calcium phosphate at from about 2 to about 3.5% by weight of the tablet;
  microcrystalline cellulose at from about 9 to about 15% by weight of the tablet;
  crospovidone at from about 5 to about 9% by weight of the tablet; and
  sodium stearyl fumarate at from about 1 to about 2% by weight of the tablet.

In a further embodiment, the ticagrelor is present in an amount of from about 12 to about 17% by weight of the tablet. In a further embodiment, the tablet comprises about 60 mg or about 90 mg of the ticagrelor. In a further embodiment, the tablet comprises about 60 mg of the ticagrelor. In a preferred embodiment, the tablet comprises about 90 mg of the ticagrelor. In further embodiments, such tablets have a disintegration time of less than 3 minutes (preferably less than 60 seconds) following storage for at least 1 month, e.g., storage at 25° C. and 60% relative humidity. In further embodiments, such tablets have a disintegration time of less than 3 minutes (preferably less than 60 seconds) following storage for longer periods (e.g. for 3, 6 or 12 months), and/or under harsher conditions (e.g. 40° C. and 75% relative humidity). In further embodiments, the tablets having the disintegration times described for the above embodiments also have an acceptable hardness (e.g., about 50 to about 150N about 50 to about 130N, about 50 to about 120N, about 50 to about 100N, or about 55 to about 90N).

In a preferred embodiment of the invention, the tablet consists essentially of:
  ticagrelor at from about 10 to about 18% by weight of the tablet;
  hydroxypropyl cellulose at from about 0.9 to about 2% by weight of the tablet;
  colloidal anhydrous silica at from about 0.5 to about 1% by weight of the tablet;
  mannitol at from about 47 to about 67% by weight of the tablet;
  xylitol at from about 2.5 to about 4% by weight of the tablet;
  anhydrous dibasic calcium phosphate at from about 2 to about 3.5% by weight of the tablet;
  microcrystalline cellulose at from about 9 to about 15% by weight of the tablet;
  crospovidone at from about 5 to about 9% by weight of the tablet; and
  sodium stearyl fumarate at from about 1 to about 2% by weight of the tablet.

In a yet further preferred embodiment, the tablet consists essentially of the ingredients listed in Example 7 in the proportions indicated therein. For the avoidance of doubt, the proportions for any of the ingredients indicated in Example 7 may be adjusted, e.g. in line with the proportions described in the embodiments above and below.

In another embodiment of the invention, the tablet comprises:
  about 60 mg of ticagrelor;
  about 259 mg of F-MELT type C;
  about 59.1 mg of mannitol in addition to the mannitol content of the F-MELT type C;
  about 8 mg of crospovidone in addition to the crospovidone content of the F-MELT type C;
  about 6 mg of sodium stearyl fumarate;
  about 5 mg of hydroxypropyl cellulose; and
  about 2.5 mg of colloidal anhydrous silica.

When used in this context, references to the amount of "F-Melt type C" comprised in the tablet are intended to refer to the amount of F-Melt type C used in the preparation of the tablet. This does not imply that any or all of that material retains the identical physical form in the final tablet. In a further embodiment, the tablet has a disintegration time of less than 3 minutes (preferably less than 60 seconds) following storage for at least 1 month, e.g., storage at 25° C. and 60% relative humidity. In further embodiments, the tablet has a disintegration time of less than 3 minutes (preferably less than 60 seconds) following storage for longer periods (e.g. for 3, 6 or 12 months), and/or under harsher conditions (e.g. 40° C. and 75% relative humidity). In further embodiments, the tablets having the disintegration times described for the above embodiments also have an acceptable hardness (e.g., about 50 to about 150N about 50 to about 130N, about 50 to about 120N, about 50 to about 100N, or about 55 to about 90N).

In another embodiment of the invention, the tablet comprises:
- about 90 mg of ticagrelor;
- about 389 mg of F-MELT type C; about 88.6 mg of mannitol in addition to the mannitol content of the F-MELT type C;
- about 12 mg of crospovidone in addition to the crospovidone content of the F-MELT type C;
- about 9 mg of sodium stearyl fumarate;
- about 7.5 mg of hydroxypropyl cellulose; and
- about 3.8 mg of colloidal anhydrous silica.

When used in this context, references to the amount of "F-Melt type C" comprised in the tablet are intended to refer to the amount of F-Melt type C used in the preparation of the tablet. This does not imply that any or all of that material retains the identical physical form in the final tablet. In a further embodiment, the tablet has a disintegration time of less than 3 minutes (preferably less than 60 seconds) following storage for at least 1 month, e.g., storage at 25° C. and 60% relative humidity. In further embodiments, the tablet has a disintegration time of less than 3 minutes (preferably less than 60 seconds) following storage for longer periods (e.g. for 3, 6 or 12 months), and/or under harsher conditions (e.g. 40° C. and 75% relative humidity). In further embodiments, the tablets having the disintegration times described for the above embodiments also have an acceptable hardness (e.g., about 50 to about 150N about 50 to about 130N, about 50 to about 120N, about 50 to about 100N, or about 55 to about 90N).

According to a further aspect of the invention, the tablet of the invention is obtainable by a process comprising granulation, for example wet granulation, of the ticagrelor.

Granulation is a process by which primary particles (powders) are made to adhere to form larger, multiparticulate entities called granules. Granulation normally commences after initial dry mixing of the powdered ingredients so that a fairly uniform distribution of ingredients through the mix is achieved. Granulation methods can be divided into two types, wet granulation methods that utilise a liquid to form the granules and dry methods that do not.

In dry granulation methods, primary powder particles are aggregated under pressure (or compaction). There are two main processes: a large tablet (also known as a slug) is produced with a heavy duty tablet press or the powder particles are compressed between two rollers to produce a sheet or 'ribbon' of material (process known as roller compaction). In both cases, the compacted material is milled using a suitable milling technique to produce granular material. The granules can then be compressed in a standard tablet press to produce tablets.

Wet granulation involves massing the primary powder particles using a granulating fluid. The fluid contains a solvent, which can be removed by drying, and is non-toxic. The granulating fluid can be used alone or more typically with a binding agent (binder) to ensure particle adhesion in the dry state. Binding agents can be added to the system as a binder solution (as part of the granulating fluid) or as dry material mixed with the primary powder particles. There are four main types of wet granulator: shear granulators (such as planetary mixers), high shear mixer granulators (such as Fielder or Diosna), twin screw granulators (such as ConsiGma) and Fluid Bed Granulators (such as Aeromatic or Glatt).

Wet granulation of a mixture comprising the ticagrelor has been found to overcome difficulties associated with the coherence and/or adherence of ticagrelor, and thereby improve the manufacturability of the active agent relative to tableting processes that involve simply direct compression of a powder.

Thus, according to a second aspect of the invention, there is provided a tablet obtainable by a process comprising wet granulation of the ticagrelor and at least one anti-caking agent. In a preferred embodiment of this aspect of the invention, the tablet is a tablet according to the first embodiment. That is, it is preferred that the tablet obtainable by a process comprising wet granulation of the ticagrelor and at least one anti-caking agent has a hardness of from about 50 to about 150N and a disintegration time of less than about 3 minutes.

In one embodiment, the wet granulation process involves the wet granulation of a mixture comprising the ticagrelor in an amount of at least about 30% of by weight of the dry ingredients in the mixture. In another embodiment, the wet granulation process involves the wet granulation of a mixture comprising the ticagrelor in an amount of at least about 35% of by weight of the dry ingredients in the mixture. The inclusion of higher concentrations of ticagrelor in the wet granulate allow the tablet to contain higher levels of disintegrating excipients, thereby improving the disintegration time.

In a further embodiment, the wet granulation process involves the wet granulation of a mixture comprising the ticagrelor in an amount of up to about 70% by weight of the dry ingredients in the mixture. In a still further embodiment, the wet granulation process involves the wet granulation of a mixture comprising the ticagrelor in an amount of from about 35 to about 70% by weight of the dry ingredients in the mixture. Surprisingly, it has been found that wet granulation of the ticagrelor is facilitated by reducing the level of ticagrelor present in the granulation mixture. Without wishing to be bound by theory, it is believed that many difficulties in manufacture, and particularly the wet granulation step, arise due to the adhesiveness and/or cohesiveness of ticagrelor. This can be countered by reducing the level of ticagrelor in the granulation mixture, and/or by increasing the relative amount of anti-caking agent present in the granulation mixture.

Thus, in a further preferred embodiment of the invention, for example one in which the tablet is made by a wet granulation process involving the wet granulation of a mixture comprising the ticagrelor at up to about 70% by weight of the dry ingredients in the mixture, the mixture used in the wet granulation process comprises an anti-caking agent in an amount ranging from about 0.1 to about 1% by weight of the dry ingredients in the mixture.

In another embodiment, the invention relates to a pharmaceutical composition prepared by high shear wet granulation. In a still further embodiment, the invention relates to a pharmaceutical composition prepared by a twin-screw wet granulation process.

High shear wet granulation is a process that involves intensive dry mixing of primary powders and subsequent addition of granulating fluid, which results in the formation of granules. The granulating fluid contains a volatile solvent (usually water) and may also include a binder; ensuring particle adhesion (binders may also be added dry as powders to the bulk of the formulation to be granulated). Granules possess major advantages compared to powders, which they are composed of, in terms of improved flow properties, reduced risk of segregation, increased homogeneity. (Information taken from Aulton ME, Pharmaceutics—The Science of Dosage Form Design, $2^{nd}$ Edition, 2002, Churchill Livingstone).

In one embodiment, the granular product obtained from the wet granulation process described herein comprises granules having a D (v, 0.9) value of less than about 1600 µm. In a preferred embodiment, the D (v, 0.9) value of less than about 1200 µm. In another embodiment, the granular product obtained from the wet granulation process described herein comprises granules having a D (v, 0.1) value of less than about 10 µm. Particle size distributions in the granules obtained in the granulation process may be determined using techniques which are known to the skilled person. Particular techniques that may be mentioned in this respect include laser diffraction techniques.

In one embodiment, as is mentioned hereinbefore, after completion of the wet granulation step the product of the granulation step may be mixed with a second amount of at least one anti-caking agent (in addition to any anti-caking agent that may be present in the granulate) after completion. This extra-granular anti-caking agent may be the same as or different from said anti-caking agent in the granulate. Alternatively, the product of the granulation step may be mixed with a glidant. In one embodiment, the second amount of an anti-caking agent or the glidant (i.e. the extra-granular anti-caking agent or glidant) is present at from about 0.2 to about 0.6% by weight of the tablet. The presence of an extra-granular anti-caking agent or glidant was advantageously found to improve the flowability of the mixture during tableting without significantly affecting the disintegration time, particularly when at least 0.3% by weight of the tablet was present. Therefore, in another embodiment, the second amount of an anti-caking agent or the glidant (i.e. the extra-granular anti-caking agent or glidant) is present at from about 0.3 to about 0.6% by weight of the tablet.

In another embodiment of the second aspect of the invention, the tablet is obtainable by a process comprising wet granulation of the ticagrelor, an anti-caking agent, and a binder. Substances that may be suitable for use as binders include hydroxypropyl cellulose, alginic acid, carboxymethylcellulose sodium, copovidone and methylcellulose or a mixture thereof. A particularly preferred binder is hydroxypropyl cellulose.

In an embodiment, the binder is present in the wet granulation mixture at an amount ranging from about 2 to about 6% by weight of the dry ingredients in the mixture. However, it has been found that increasing the amount of binder used in the granulation (e.g. wet granulation) step has been found to shorten the disintegration time for the tablet of the invention. Thus, in a preferred embodiment, the binder is present in the wet granulation mixture at an amount ranging from about 3 to about 6% by weight of the dry ingredients in the mixture. In a further embodiment the binder is present in the wet granulation mixture at an amount ranging from about 4 to about 5% by weight of the dry ingredients in the mixture.

The form in which the ticagrelor is supplied for the granulation step also affects the disintegration time of the tablet of the invention. Ticagrelor exists in an amorphous form and in four different substantially crystalline forms (see International Patent Application number PCT/SE01/01239 (publication number WO 01/92262)). In one embodiment of either the first or second aspects, the invention relates to a tablet as hereinabove defined in which the ticagrelor is in a crystalline form.

In one embodiment, the invention relates to a pharmaceutical composition in which the ticagrelor is substantially present in the form of polymorph II. In another embodiment, the invention relates to a pharmaceutical composition in which the ticagrelor is substantially present in the form of polymorph III. By the use of the term "substantially present" in this context, it is meant that the ticagrelor is provided in a form which is predominantly that of the specified polymorph, for example at least 80% by weight of the ticagrelor is in the form of the specified polymorph. More preferably, at least 90% or at least 95% (e.g. at least 96%, at least 97%, at least 98% or at least 99%) by weight of the ticagrelor is in the form of the specified polymorph (e.g. either polymorph II or polymorph III).

The particle size for the ticagrelor prior to its incorporation into the tablet of the invention may also affect the disintegration time of the tablet. Tablets prepared using ticagrelor having a range of particle sizes have been found to have the desired disintegration properties. In one embodiment, the ticagrelor has a D (v, 0.9) particle size distribution of from about 5 µm to about 50 µm. In a further embodiment, the ticagrelor has a D (v, 0.9) particle size distribution of from about 5 µm to about 40 µm. In a more preferred embodiment, the ticagrelor has a D (v, 0.9) particle size distribution of from about 10 µm to about 30 µm.

It is desirable that the physical properties of these compositions are stable on storage, as changes in for instance, disintegration times, dissolution rates or tablet hardness among others can affect product performance. It is possible that decreases in dissolution rate on storage under International Council for Harmonisation of Technical Requirements for Registration of Pharmaceuticals for Human Use (ICH) stability testing conditions, used to assign product shelf life, can reduce the bioavailability of the ticagrelor. Physical property stability can be measured by USP methodologies for disintegration times and dissolution testing, as is discussed elsewhere herein.

In a third aspect of the invention, there is provided a method of preparing the tablet of the first and second aspects of the invention.

Said method comprises mixing together ticagrelor and at least one anti-caking agent along with, or in, a liquid, so providing a wet granulate. In a preferred embodiment, the wet granulate mixture is mixed with a high shear mixer. In a still further embodiment, the wet granulate mixture is processed using a twin-screw granulator. In another embodiment, the liquid used in the wet granulation process is water.

The wet granulate mixture may further contain a filler and a binder. In one embodiment, the filler is mannitol. In a further embodiment, the binder is hydroxypropylcellulose.

In an embodiment of the third aspect of the invention, the method of preparing the tablet involves providing a wet granulation mixture comprising:
  ticagrelor at from about 35 to about 70% by weight of the dry ingredients in the mixture; and
  an anti-caking agent in an amount ranging from about 0.1 to about 1% by weight of the dry ingredients in the mixture.

In a further embodiment, in addition to containing the ticagrelor and the anti-caking agent in the proportions indicated immediately above, the mixture used in the method further comprises:

a filler in an amount ranging from about 25% to about 60% by weight of the dry ingredients in the mixture; and/or a binder in an amount ranging from about 3 to about 6% by weight of the dry ingredients in the mixture.

In each of the embodiments described herein in connection with the third aspect of the invention, said method may further comprise the steps of:

(I) drying the wet granulate mixture,
(II) adding one or more excipients to the dried granulates, and then
(III) forming the mixture into tablets.

The drying process of step (I) above may involve any conventional drying process, and in a preferred embodiment it involves fluid bed drying with an inlet air temperature of about 50° C. The granulate product obtained therefrom may further be milled in order to obtain granulates with a desired particle size distribution. A mill screen may further be used to achieve this. In one embodiment, the dried granules are milled to yield a particle size distribution in which the D (v, 0.9) is less than about 1600 μm. The particle size distribution may be determined using techniques known to those skilled in the art, for example the laser diffraction method described herein.

The drying process of step (I) may be preceded by a wet milling step in order to eliminate any large lumps that may be present in the wet granulate, and thereby facilitate the drying process.

The mixture containing the granulates and the one or more excipients may be formed into tablets using any conventional tableting press. In one embodiment, the tablets are compressed using a compaction force of between 6 kN and 15 kN (e.g. between 7.9 kN and 13.1 kN).

In a further embodiment, the one or more excipients introduced in step (II) above includes at least one disintegrating excipient as hereinbefore defined, a second amount of an anti-caking agent as hereinbefore defined, and/or a lubricant as hereinbefore defined.

Preferences and options for a given aspect, feature or parameter of the invention should, unless the context indicates otherwise, be regarded as having been disclosed in combination with any and all preferences and options for all other aspects, features and parameters of the invention. For example, any of the disintegrating excipients mentioned herein may be used in combination with any of the binders, anti-caking agents and/or lubricants mentioned herein. Furthermore, said components may be present in the tablets of the invention in any of the proportions mentioned herein, or in any combination of said proportions.

Ticagrelor in the tablets of the invention acts as $P_{2T}$ ($P2Y_{ADP}$ or $P2T_{AC}$) receptor antagonists. Accordingly, the tablets of the invention are useful in therapy. In particular, the tablets of the invention are indicated for use in the treatment or prophylaxis of arterial thrombotic complications in patients with coronary artery, cerebrovascular or peripheral vascular disease. Arterial thrombotic complications may include unstable angina, primary arterial thrombotic complications of atherosclerosis such as thrombotic or embolic stroke, transient ischaemic attacks, peripheral vascular disease, myocardial infarction with or without thrombolysis, arterial complications due to interventions in atherosclerotic disease such as angioplasty, including coronary angioplasty (PTCA), endarterectomy, stent placement, coronary and other vascular graft surgery, thrombotic complications of surgical or mechanical damage such as tissue salvage following accidental or surgical trauma, reconstructive surgery including skin and muscle flaps, conditions with a diffuse thrombotic/platelet consumption component such as disseminated intravascular coagulation, thrombotic thrombocytopaenic purpura, haemolytic uraemic syndrome, thrombotic complications of septicaemia, adult respiratory distress syndrome, anti-phospholipid syndrome, heparin-induced thrombocytopaenia and pre-eclampsia/eclampsia, or venous thrombosis such as deep vein thrombosis, venoocclusive disease, haematological conditions such as myeloproliferative disease, including thrombocythaemia, sickle cell disease; or in the prevention of mechanically-induced platelet activation in vivo, such as cardio-pulmonary bypass and extracorporeal membrane oxygenation (prevention of microthromboembolism), mechanically-induced platelet activation in vitro, such as use in the preservation of blood products, e.g. platelet concentrates, or shunt occlusion such as in renal dialysis and plasmapheresis, thrombosis secondary to vascular damage/inflammation such as vasculitis, arteritis, glomerulonephritis, inflammatory bowel disease and organ graft rejection, conditions such as migraine, Raynaud's phenomenon, conditions in which platelets can contribute to the underlying inflammatory disease process in the vascular wall such as atheromatous plaque formation/progression, stenosis/restenosis and in other inflammatory conditions such as asthma, in which platelets and platelet-derived factors are implicated in the immunological disease process. Further indications include treatment of CNS disorders and prevention of the growth and spread of tumours.

The tablets of the first and second aspects of the invention may be particularly useful in treating or preventing atherothrombotic events in patients with cardiovascular disease. In one embodiment, the patient is suffering from acute coronary syndrome and/or has a history of myocardial infarction. Thus, according to a fourth aspect of the invention, there is provided a method of treating or preventing atherothrombotic events in patients with cardiovascular disease, which method comprises administration of a tablet according to the first or second aspects of the invention to a patient suffering from or susceptible to such a disorder.

According to a fifth aspect, the invention provides the use of a composition comprising:

(1S,2S,3R,5S)-3-[7-{[(1R,2S)-2-(3,4-difluorophenyl)cyclopropyl]amino}-5-(propylthio)-3H-[1,2,3]-triazolo[4,5-d]pyrimidin-3-yl]-5-(2-hydroxyethoxy)cyclopentane-1,2-diol; and at least one disintegrating excipient;

in the manufacture of a medicament for use in treating or preventing atherothrombotic events in patients with cardiovascular disease, wherein the medicament is in the form of a tablet according to the first or second aspects of the invention.

Particular atherothrombotic events that may be mentioned in this respect include atherothrombotic events selected from the group consisting of cardiovascular death, myocardial infarction, stroke (e.g. ischemic stroke) and peripheral arterial disease. The tablets of the invention may also be useful in treating or preventing atherothrombotic events in patients with diabetes.

The ticagrelor is also capable of reducing the rate of stent thrombosis in a patient that has been stented for the treatment of acute coronary syndrome. Thus, according to a sixth aspect of the invention, there is provided a method of treating or preventing stent thrombosis in a patient that has been stented for the treatment of acute coronary syndrome, which method comprises administration of a tablet according to the first or second aspects of the invention to said patient.

According to a seventh aspect, the invention provides the use of a composition comprising:

(1S,2S,3R,5S)-3-[7-{[(1R,2S)-2-(3,4-difluorophenyl)cyclopropyl]amino}-5-(propylthio)-3H-[1,2,3]-triazolo[4,5-d]pyrimidin-3-yl]-5-(2-hydroxyethoxy)cyclopentane-1,2-diol; and at least one disintegrating excipient;

in the manufacture of a medicament for use in treating or preventing stent thrombosis, wherein the medicament is in the form of a tablet according to the first or second aspects of the invention. In a preferred embodiment, the patient is a patient that has been stented for the treatment of acute coronary syndrome.

The methods and uses of the fourth to seventh aspects of the invention are particularly useful in enabling the ticagrelor to be administered to patients that have difficulty swallowing conventional oral formulations (e.g. patients that suffer from dysphagia). Such patients include elderly patients. Other patients that may benefit from receiving the tablets of the invention include patients that have previously suffered a myocardial infarction or a stroke.

By the term "treat," "treating," or "treatment of" (and grammatical variations thereof) it is meant that the severity of the subject's condition is reduced, at least partially improved or ameliorated and/or that some alleviation, mitigation or decrease in at least one clinical symptom is achieved and/or there is a delay in the progression of the disease or disorder.

By the term "prevent", "preventing", or "prevention of" (and grammatical variations thereof) it is meant that the likelihood of the patient suffering from the condition is reduced, at least partially reduced or averted and/or that some prophylaxis, or inhibition of at least one clinical symptom is achieved and/or there is a delay in the onset of the disease or disorder.

A "subject in need" of the methods of the invention can be a subject known to have or suspected of suffering from an acute coronary syndrome.

Blister Packs

Push-through type blister packing is known in the art, and provides a simple method for packaging tablets and capsules in a manner which allows the patient to release each tablet or capsule at the moment of need. However, the push-through action associated with this type of packaging has been found to place forces on the tablets and capsules contained therein which can lead to unacceptable levels of breakage. This is particularly the case for tablets having a relatively low hardness, e.g. the tablets of the first and second aspects of the invention.

We have now discovered a novel form of packaging which overcomes some of these deficiencies.

Thus, in an eighth aspect of the invention, there is provided a blister pack that is suitable for use with pharmaceutical formulations, especially tablets and capsules. The blister pack comprises a blistered base sheet to which is bonded a lidding sheet. The blistered base sheet also comprises one or more cavities. A break is present in the blistered base sheet and lidding sheet such that the blister pack is tearable at the break to expose one of the cavities. Such a blister pack is referred to hereinafter as "the packaging of the invention".

Embodiments of the packing of the invention are shown in FIGS. 1A, 1B, 2A, 2B, 3A and 3B. The packaging of the invention is intended to provide a form of storage which is easily opened by patients, in particular the elderly or infirm. The packaging is also intended to be useful for tablets that are fragile (e.g. tablets having a high friability). The packaging is openable by way of a tearing action which serves to expose the contents of one of the cavities in the blister pack and thereby releasing the tablet or capsule contained within the cavity. Tablets and capsules may be packaged individually within each cavity.

The packaging of the invention comprises a sheet containing a blistered base sheet 10 to which is bonded a lidding sheet 11 in which one or more cavities are present between the blistered base sheet and lidding sheet. The blister pack 20 has an outer edge 21 which contains one or more breaks 22. These breaks 22, which may also be referred to as "tear notches", are breaks in both the blistered base sheet 10 and the lidding sheet 11. The breaks function to provide a tear point in the edge of the blister pack such that the blister pack is tearable. When torn at the break, the tearing action opens one of the cavities 23 in order to expose its contents. Typically, each cavity contains a single tablet or capsule 12.

The user may tear open the blister pack by grasping the portions of the blister pack which are located on either side 24, 25 of the break, and then pulling these portions apart. The action of pulling these regions apart causes a tear to occur at the break. Therefore, in one embodiment, the break separates two regions of the edge of the blister pack which are capable of being gripped and pulled apart to tear the blistered base sheet and the lidding sheet.

In one embodiment, the break 22 (or tear notch) is positioned adjacent to one of the cavities 23. By locating the break 22 adjacent to one of the cavities 23, a tear initiated at that break is more likely to follow a path which intercepts with, and thereby exposes, one of the cavities.

In a further embodiment, the blister pack contains a plurality of said breaks 22 in the outer edge 21. In such cases, more than one break may be associated with each cavity in the blister, thereby providing multiple points at which the user may initiate a tear in the packaging. By the use of the phrase "associated with" it is meant that the break is in close proximity to the cavity, or it is positioned such that a tear initiated at that break will follow a tear path which intercepts with the cavity. In one embodiment, the break 22 is positioned adjacent to a cavity 23. Preferably, the blister pack contains one break 22 in association with each cavity 23. Thus, in a further embodiment, the blister pack contains at least one break 22 positioned adjacent to each cavity 23.

In a preferred embodiment, the blister pack 20 contains a plurality of cavities, such as from 4 to 24 cavities (e.g. from 6 to 14 cavities). In a particular embodiment, the blister pack contains 8 or 10 cavities.

In embodiments in which the blister pack contains a plurality of cavities, the blister pack contains a plurality of said breaks 22. Preferably, the number of breaks is equal to the number of cavities, and the blister pack contains one break 22 in association with (e.g. positioned adjacent to) each cavity 23.

The break may take any shape, configuration or dimension suitable for facilitating tearing of the blister pack in the manner described herein. In one embodiment, the break is a cleft 31 or an incision 32. The term "cleft" refers to a cut-in in the outer edge of the blister pack wherein material has been removed from the base and lidding sheets to form the break. The cleft may take any suitable shape which facilitates the initiation of a tear at the break when the regions of the edge of the blister pack located either side of the break are pulled apart. Typically this is achieved by ensuring that the cleft comprises a cusp 33 (i.e. a form of singularity) at which the tear may be initiated. In one embodiment, the cleft 31 is triangular. In another embodiment, the edges of the cleft are curved inward (i.e. into the cleft), so giving a shape similar to the cusp of an astroid. By using a cleft with curved edges, this increases the area of the base and lidding sheets which may be gripped by the user.

The term "incision" refers to a linear or curved cut extending inward from the outer edge of the blistered base sheet 20. Where the cleft is in the form of an incision 32, little or none of the blister pack is removed in the formation of the cleft, and this also increases the area of the base and lidding sheets which may be gripped by the user. The innermost end of the incision (i.e. the end of the incision which does not lie on the outer edge of the blister pack) is a cusp.

The break should be sufficiently small so as to avoid compromising the seal around the cavities prior to tearing. Typically the minimum distance between the cavity 23 and the nearest break 22 (or the edge of the blister pack) should be at least 3 mm.

Typically, the cusp 33 of the break (e.g. wherein the break is a cleft or an incision) is the innermost point, and therefore the point of the break that is closest to any given cavity 23. Thus, in a further embodiment, the innermost part 33 of the break is at least 3 mm from the nearest cavity 23.

The break 22 should also be of sufficient size for it to be capable of initiating a tear in the blister pack when a tearing force is applied. Typically, the break should extend inward from the outer edge 21 to a distance of at least about 1 mm, and preferably at least about 2 mm.

The blistered base sheet 10 and the lidding sheet 11 should both be formed from a material (e.g. a plurality of materials in the form of a laminate) which is capable of being torn by a user when a sufficient tearing force is applied. The blistered base sheet and the lidding sheet should also be sufficiently strong durable to minimise the risk of compromising the integrity of the packaging prior to tearing by the user.

In one embodiment, the blistered base sheet 10 comprises an aluminium layer or a polymer layer. Preferably, the blistered base sheet 10 comprises an aluminium layer. In embodiments in which the blistered base sheet comprises an aluminium layer, said aluminium layer may have a thickness of from about 30 to about 60 µm, preferably about 45 µm.

In an alternative embodiment, the blistered base sheet 10 does not comprise an aluminium layer. In such alternative embodiments, the blistered base sheet comprises at least one layer formed from a polymer, such as polyvinyl chloride (PVC), polypropylene, a polyester (e.g. PET), or a polyamide.

In another embodiment, the blistered base sheet 10 comprises a plurality of layers. For example, one of said plurality of layers may be an aluminium layer as described above. Other materials that may be used in such laminates include polymers, such as polyvinyl chloride (PVC), polypropylene, a polyester (e.g. PET), and a polyamide. Other materials that may be used in the blistered base sheet comprising a plurality of layers includes a sealing agent. Typically, the sealing agent forms the innermost layer which therefore may come into contact with the contents of the cavities. Still further materials that may be used include coatings, e.g. polyvinylidene chloride (PVDC). Such materials may provide advantages in reducing the permeability of the blister pack to gas and moisture. This is particularly important for the tablets according to the first and second aspects of the invention as these tablets have a relatively high hygroscopicity.

In embodiments in which the blistered base sheet 10 comprises a plurality of layers, the blistered base sheet may have a thickness of from about 100 to about 200 µm.

In a further embodiment, the blistered base sheet 10 comprises (or consists essentially of) an aluminium layer, a PVC layer and a polyamide layer. In an example of such an embodiment, the PVC layer is the innermost layer and the polyamide layer is the outermost layer. Adhesive layers may also be present in such embodiments between the aluminium, OVC and polyamide layers in order to glue them together. One or more lacquer layers may also be present on the blistered base sheet. Lacquer layers may be used to aid in the formation of a heat seal between the blistered base sheet and the lidding sheet. In a further example of said blistered base sheet, the blistered base sheet 10 has a thickness of from about 100 to about 200 µm.

In one embodiment, the lidding sheet 11 comprises an aluminium layer. In embodiments in which the lidding sheet comprises an aluminium layer, said aluminium layer may have a thickness of from about 10 to about 30 µm, preferably about 20 µm.

In another embodiment, the lidding sheet 11 comprises a plurality of layers. For example, one of said plurality of layers may be an aluminium layer as described above. Other materials that may be used in such laminates include polymers, such as polyvinyl chloride (PVC), polypropylene, a polyester (e.g. PET), and a polyamide. Other materials that may be used in this respect is paper. The use of paper as the uppermost layer facilitates the printing with inks on the blister pack. One or more lacquer layers may also be present in the lidding sheet. Lacquer layers may be used to aid in the formation of a heat seal between the blistered base sheet and the lidding sheet.

In embodiments in which the lidding sheet 11 comprises a plurality of layers, the lidding sheet may have a thickness of from about 15 µm to about 60 µm.

In a further embodiment, the lidding sheet 11 comprises (or consists essentially of) an aluminium layer, and a lacquer layer. In an example of such an embodiment, the lacquer layer is the innermost layer. In a further example of said lidding sheet, the lidding sheet has a thickness of from about 15 µm to about 60 µm, e.g. from about 15 µm to about 45 µm. Printing may further be applied to the outermost surface of the lidding sheet.

In embodiments in which the blister pack comprises a plurality of cavities, the packaging may be provided in a form in which one or more of these cavities may be detached from the others without compromising the seal of any of the cavities. This may be done through the use of a perforated region 26 of the blister pack which facilitates separation by the user of one or more of the cavities from the remainder. The perforated region 26 should form a tear path which passes between two of said cavities such that tearing of the blister pack initiated at one end of the perforated region will lead to tearing along the perforation. This tear path differs from that associated with any of the breaks hereinbefore mentioned as it does not facilitate the formation of a tear which intercepts with one or more of the cavities.

Thus in a yet further embodiment the blister pack comprises at least two cavities and further comprises a perforated region which forms a tear path passing between two of said cavities.

As is stated above, the blister packs of the invention may be used in connection with any tablet, capsule or other suitable pharmaceutical formulation 27. However, the blister packs of the eighth aspect of the invention are particularly suited for use in storing the tablets 27 of the first or second aspects of the invention. Thus in one embodiment, the blister pack 20 of the invention contains one or more tablets or capsules 27. In a further embodiment, the blister pack of the invention contains one or more tablets according to the first or second aspects of the invention.

Blister packs without breaks in the outer edge may be manufactured by methods known to those skilled in the art. The primary processes that are used to form blister packs are thermoforming methods and cold forming methods.

Thermoformed blister packs have a forming film of (usually) transparent polymer, normally PVC based. The blister cavities are produced by heating the film to soften it and then to "push" the film into cavities in a steel tooling, typically using compressed air.

Cold form blister packs are made of an aluminium foil forming foil (base sheet). The cavities are produced by pressing a steel tool onto the foil. No heat is used for forming cavities in cold formed blister packs.

For both types of blister packs an aluminium lidding foil is sealed against the forming foil by applying heat in the sealing station.

Suitable materials and methods for manufacturing blister packs are disclosed in Pilchik R., Pharmaceutical Blister Packaging, Part I (Rationale and Materials), Pharmaceutical Technology NOVEMBER 2000, 668.

The introduction of a break in the outer edge of the blister packs of the invention may be readily achieved through the use of a punching or cutting tool. After sealing the forming film/foil (i.e. base sheet) and lidding foil, the individual blister packs (or blister sheets) are punched out with sharp punching tools. At this stage in the process, the outer edge of the blister packs may be shaped, and perforations may be added in the inner regions of the blister packs between the cavities. Punching is a standard technique that typically is used as last step in blister machines, thus the introduction of one or more breaks in the outer edge of the blister packs can be achieved at a very low cost.

The term "about," as used herein when referring to a measurable value such as an amount of an excipient, time, temperature, and the like, refers to variations of 20%, 10%, 5%, 1%, 0.5%, or even 0.1% of the specified amount, unless otherwise indicated.

FIGURES

FIG. 3A shows a plan view of a portion of a blister pack with a cleft. FIG. 3B shows a plan view of a portion of a blister pack with an incision.

ANALYTICAL METHODS

Figure 1A:
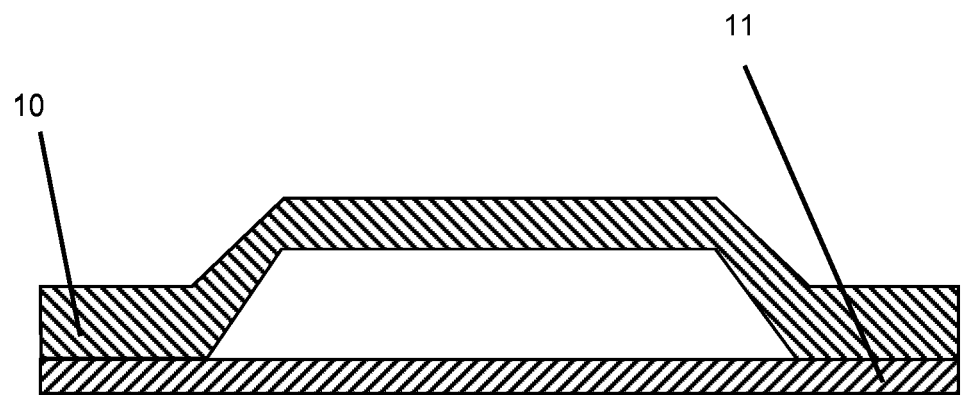
FIGS. 1A and 1B show plan views of a blister pack. Tablets are shown within the blister pack in FIG. 1B.
Figure 1B:
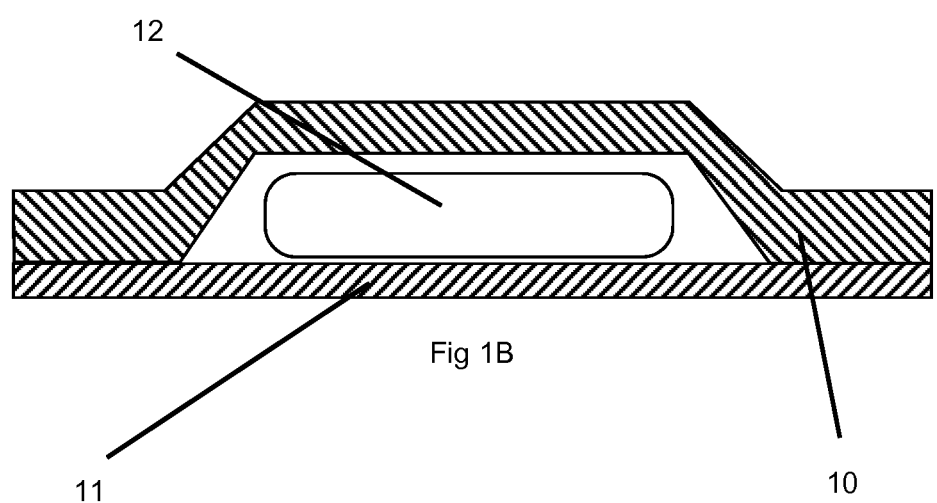
Figures 2A, 2B:
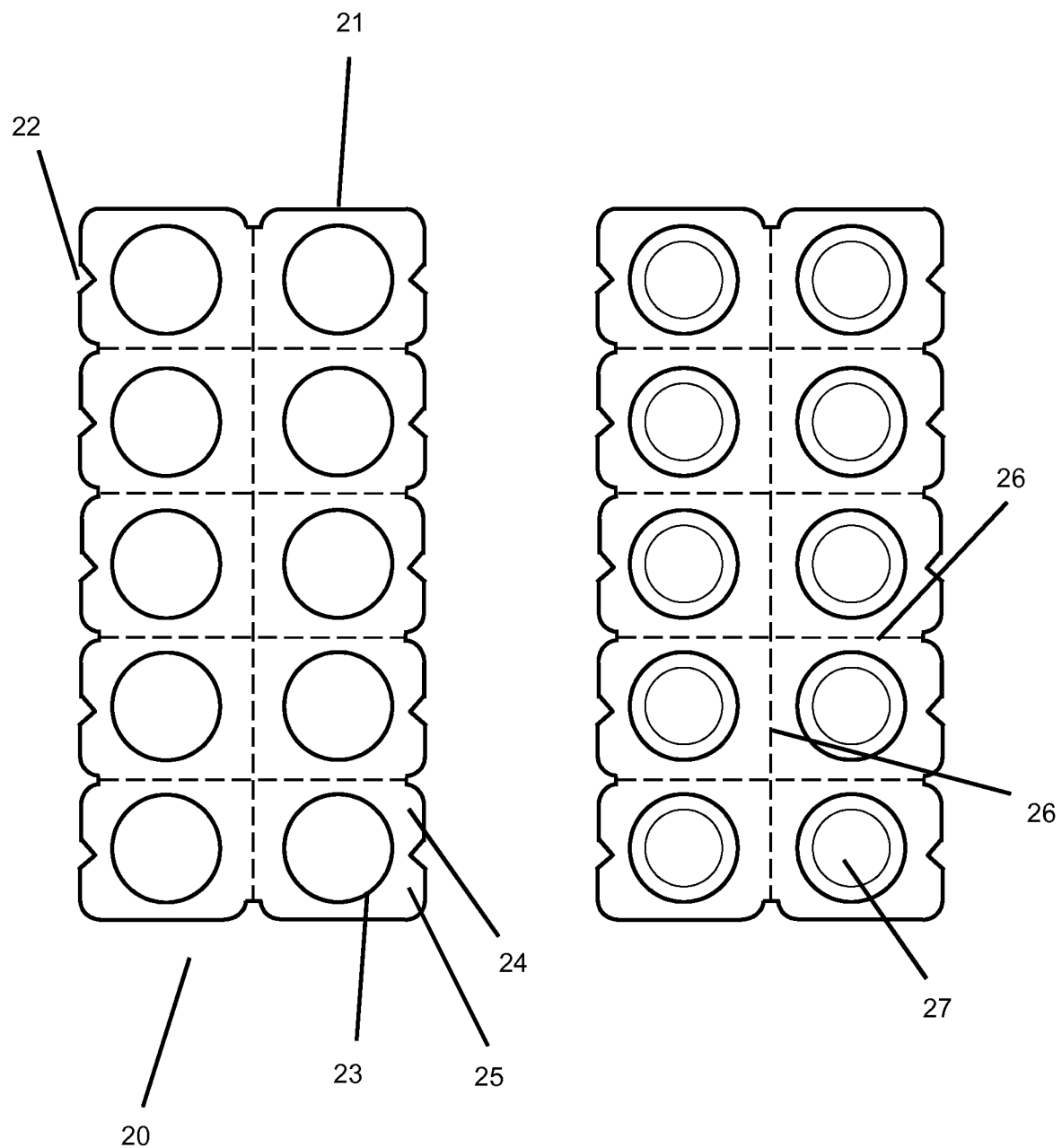
FIGS. 2A and 2B show side views of a single blister. A tablet is shown within the blister in FIG. 2B.

In the examples described below, various parameters were measures according to the following analytical methods.

Friability was measured in accordance with the method set out in USP monograph 1216 (Tablet Friability).

Hardness was measured in accordance with the method set out in USP monograph 1217 and PhEur 2.9.8 (Resistance to Crushing of Tablets).

Disintegration time was measured in accordance with the method set out in USP monograph 701 (Disintegration).

Dissolution time was measured in accordance with the method set out in USP monograph 711 (Dissolution).

Particle size distributions for the ticagrelor as received from suppliers and for granulates used in the tableting processes were measured using a laser diffraction method (in "wet" and "dry" conditions). In wet methods, particles of drug were suspended in a suitable suspending fluid (e.g. 0.5% v/v sorbitan trioleate in cyclohexane) and laser diffraction particle size analysis of the suspension was conducted using a Malvern Mastersizer 2000. In dry methods, particles size distribution measurements (typically for granules) were made by laser diffraction using dry material, i.e. without the aid of a suspending fluid. Unless otherwise specified, particle size measurements were made under standard measurement conditions appropriate for the technique.

Focused Beam Reflectance Measurement (FBRM) analyses were conducted in dissolution studies. The FBRM technique involves the insertion of a probe directly into a process stream, at an angle, to ensure particles can flow easily across the probe window where the measurement takes place. A laser beam is launched down the probe tube through a set of optics and focused to a tight beam spot at the sapphire window. The optics rotate at a fixed speed (typically 2 m/s) resulting in the beam spot rapidly scanning across particles as they flow past the window. As the focused beam scans across the particle system, individual particles or particle structures will backscatter the laser light to the detector. These distinct pulses of backscattered light are detected, counted, and the duration of each pulse is multiplied by the scan speed to calculate the distance across each particle. This distance is defined as the chord length, a fundamental measurement of the particle related to the particle size, and a precise and highly sensitive chord length distribution can be reported in real time, thus tracking how particle size and count change over time. In the measurements, the probe diameter was approximately 6 mm and has a sapphire window at the probe end. The integration time was set to 5 seconds. The instrument was set on "coarse" mode and focal spot scan rate on 2 m/sec. The probe was placed 2 cm above the paddle.

The invention may by illustrated by the following non-limiting examples.

In these examples, F-melt type M and F-melt type C (also referred to herein as "F-melt" in the Examples) were supplied by Fuji Chemicals, Ludiflash was supplied by BASF, and GalenIQ (Grade 721) was supplied by Beneo-Palatinit, Mannitol was supplied by Roquette, crospovidone (Kollidon CL-SF and Kollidon CL-F) was supplied by BASF. Sodium stearyl fumarate was supplied by JRS Pharma, Hydroxypropyl cellulose was supplied by Ashland, colloidal anhydrous silica was supplied by Cabot GmbH.

Example 1—Assessment of Direct Compression Tablets

Four 500 g batches of direct compression (DC) tablets were produced using the formulation compositions detailed in Table 1.

TABLE 1

Compositions of direct compression tablet batches

| Component | Batch 1 | Batch 2 | Batch 3 | Batch 4 |
|---|---|---|---|---|
| Ticagrelor | 15.0 | 15.0 | 15.0 | 15.0 |
| F-MELT, type M | 71.0 | — | — | — |
| F-MELT, type C | 10.0 | — | — | — |
| Ludiflash | — | 81.0 | — | — |
| GalenIQ | — | — | 81.0 | 75.0 |
| Crospovidone | — | — | — | 7.0 |
| Silica, collodial anhydrous | 1.0 | 1.0 | 1.0 | 1.0 |
| sodium stearyl fumarate | 3.0 | 3.0 | 3.0 | 3.0 |
| Total | 100.0 | 100.0 | 100.0 | 100.0 |

All values are weight percentages.

The first three batches varied in the use of fast oral disintegrating excipient. F-MELT type M and C, Ludiflash or GalenIQ was used. Colloidal anhydrous silica was added to overcome the adhesive and cohesive nature of ticagrelor. As lubricant, sodium stearyl fumarate was included. The formulation containing GalenIQ was shown to have long disintegration time, for that reason a fourth experiment with a composition containing GalenIQ and 7% of the disintegrant crospovidone was carried out.

The major observation during tablet compression was that the compositions including F-MELT (Batch 1) and Ludiflash (Batch 2) had poor flowability whereas the GalenIQ formulations (Batch 3 and Batch 4) had good flowability (see Table 2). This is reflected in the hardness and weight analysis where the F-MELT and Ludiflash formulations had high variability (RSD-value), whereas the opposite was observed for the two GalenIQ formulations.

TABLE 2

Observations and results

| Quality attribute | Batch 1 F-MELT | Batch 2 Ludiflash | Batch 3 GalenIQ | Batch 4 GalenIQ + cros. |
|---|---|---|---|---|
| Flowability | poor | poor | good | good |
| Picking/Sticking | no | no | no | no |
| Hardness, n = 10 | | | | |
| Average (N) | 60.3 | 67.4 | 37.3 | 35.4 |
| RSD (%) | 21.6 | 27.2 | 7.78 | 9.60 |
| Tablet weight, n = 10 | | | | |
| Average (mg) | 617.9 | 613.4 | 605.8 | 598.0 |
| RSD (%) | 4.35 | 3.54 | 1.04 | 1.95 |
| Friability (%) | 0.8 | 0.9 | 1.9 | 1.2 |
| Disintegration (s), n = 6 | 28 | 29 | 62 | 60 |

Typically preferred RSD values for the hardness measurements are less than 20%. Typically preferred RSD values for the tablet weight measurements are less than 4.0%. Typically preferred friability values are less than 1.0%. Typically preferred disintegration times are less than 30 seconds.

None of the tablet formulations showed any sign of sticking or picking tendencies. The analysis of friability and disintegration showed that F-MELT and Ludiflash provided tablets with good disintegration properties (disintegration time of about 30 seconds), and acceptable friability (less than 1%). The GalenIQ composition on the other hand had neither acceptable disintegration time nor friability. Adding 7% of the disintegrant crospovidone did not significantly shorten the disintegration time of the GalenIQ composition.

With tablets containing F-MELT or Ludiflash there was a risk of not meeting the (Critical Quality Attributes) QCA of uniformity of dosage units because of the low flowability. With tablets containing GalenIQ there was on the other hand a risk of not meeting the CQAs of assay (because of high friability) and disintegration. Further studies were conducted (see Examples 2 to 6) in which the ticagrelor particles were incorporated in granules to try to counter the flowability difficulties.

Example 2—Assessment of Wet-Granulation Tablets

This experiment was designed to assess wet granulation of ticagrelor, followed by dry-mixing with the other excipients prior to tablet compression. Included in the formulation was the fast oral disintegrating excipient of either F-MELT or Ludiflash, shown to provide favourable disintegrating properties. In this and all subsequent examples, only F-melt type C has been evaluated, rather than F-melt type M. References to "F-melt" in the compositions used in this and subsequent examples are references to F-melt type C, unless otherwise specified.

Table 3 details the composition of the granulation batches in this example. Water was chosen as the granulation liquid and the binder hydroxypropylcellulose was added dry. In order to reduce the cohesive and adhesive nature of ticagrelor, colloidal anhydrous silica was used as anticaking agent. Three 100 g batches of ticagrelor granules were composed. The two last batches were duplicates in order to evaluate the granules both with Ludiflash and F-MELT in the tablet composition.

TABLE 3

Composition of granulation batches

| Component | Batch 5 | Batch 6 | Batch 7 |
|---|---|---|---|
| Ticagrelor | 95.0 | 95.0 | 95.0 |
| Hydroxypropylcellulose | 5.0 | 4.5 | 4.5 |
| Silica, colloidal anhydrous | — | 0.5 | 0.5 |
| Water, purified[a] | 30.0 | 30.0 | 30.0 |

[a] removed during manufacturing process
All values are weight percentages.

The ticagrelor granules were included in two 500 g tablet batches, one containing Ludiflash and the other F-MELT, see Table 4 for the compositions. In order to further improve the disintegration time of the tablets, 5% of crospovidone was added to the formulation. Sodium stearyl fumarate and colloidal anhydrous silica were also included, as lubricant and glidant, respectively.

Granulation of ticagrelor without colloidal anhydrous silica showed poor manufacturability. The powder adhered to the walls of the granulator and was subjected to caking formation. For that reason the ticagrelor granule batch without silica (Batch 5) was not evaluated for tablet compression. When 0.5% (w/w) of silica was added to the granulation blend the problem was decreased and the two other batches of ticagrelor granules could be evaluated in tablet compositions.

TABLE 4

Composition of tablet batches

| | Batch (granulation batch) | |
|---|---|---|
| Components | 6 | 7 |
| Ticagrelor granules | 15.8 | 15.8 |
| F-MELT type C | 77.0 | — |
| Ludiflash | — | 77.0 |
| Crospovidone | 5.00 | 5.00 |
| Sodium stearyl fumarate | 2.00 | 2.00 |
| Silica, colloidal anhydrous | 0.20 | 0.20 |

All values are weight percentages.

Table 5 summarises the results and observations from tablet compression of the two granules, blended with either Ludiflash or F-MELT and compares the results with the results of the two batches in Example 1, with either Ludiflash or F-MELT where ticagrelor was not granulated. The attributes of picking, sticking and flowability in Table 5 are visual observations during compression whereas the other four quality attributes are analysis of the manufactured tablets.

Both F-MELT and Ludiflash compositions showed improved flowability when ticagrelor was granulated compared to the non-granulated powder blend in Example 1. This is reflected in the lower variability of tablet hardness and weight, see RSD-values in Table 5. Out of the two compositions including granules, the one containing F-MELT showed better flowability than the one containing Ludiflash, but both compositions provided tablets with disintegration of less than about 30 second and acceptable friability of less than 1%.

Including granules of ticagrelor in the formulation reduced the risk of not meeting the CQA of uniformity of dosage unit and maintained the desired CQAs of assay (connected to a low friability) and disintegration. This finding supports the incorporation of a granulation step for ticagrelor in the manufacturing process for ticagrelor orodispersible tablets. Only F-melt was evaluated further as it showed better flowability than Ludiflash, as is evident from the improved RSD value for the hardness. The RSD value for the weight was also better for batches containing F-melt rather than Ludiflash, and this is further evidence of the improved flowability observed when using F-melt in place of Ludiflash.

TABLE 5

Results and observations from Examples 1 and 2

| | Batch (explanation) | | | |
|---|---|---|---|---|
| Quality attributes | 6 F-MELT (gran) | 1 F-MELT (DC) | 7 Ludiflash (gran) | 2 Ludiflash (DC) |
| Picking/Sticking | no | no | no | no |
| Flowability | good | poor | moderate | poor |
| Hardness, n = 10 | | | | |
| Average (N) | 44.0 | 60.3 | 46.0 | 67.4 |
| RSD (%) | 6.8 | 21.6 | 21.3 | 27.2 |
| Tablet weight, n = 10 | | | | |
| Average (mg) | 603.4 | 617.9 | 606.4 | 613.4 |
| RSD (%) | 1.95 | 4.35 | 2.57 | 3.54 |
| Friability (%) | 0.5 | 0.8 | 0.6 | 0.9 |
| Disintegration (s), n = 6 | 28 | 28 | 29 | 28 |

Typically preferred RSD values for the hardness measurements are less than 20%. Typically preferred RSD values for the tablet weight measurements are less than 4.0%. Typically preferred friability values are less than 1.0%. Typically preferred disintegration times are less than 30 seconds.

Example 3—Assessment of Granulation Composition

The aim of this study was to build knowledge around, as well as improving the granulation and tablet composition. The granulation process was scaled up from 100 g to 500 g batches. The tablet batch size was still 500 g.

Table 6 details the composition of the granulation batches included in the study. The granules contain different amount of ticagrelor, 95% (Batch 8), 64% (Batch 10) and 48% (Batch 9) were evaluated. In the last two of the three batches a part of the ticagrelor was exchanged to the filler mannitol, where a small sized grade was chosen in order to get homogenous granules.

TABLE 6

Composition of granulation batches in Example 3

| | Batch | | |
|---|---|---|---|
| Components | 8 | 9 | 10 |
| Ticagrelor | 95.0 | 48.38 | 64.30 |
| Mannitol | — | 48.38 | 32.20 |
| Hydroxypropylcellulose | 4.50 | 3.00 | 3.00 |
| Silica, colloidal anhydrous | 0.50 | 0.25 | 0.50 |
| Water, purified[a] | 30.0 | 30.0 | 30.0 |

[a]Removed during process.
All values are weight percentages.

The granulation batches were evaluated in subsequent tablet compression. Table 7 details the composition of the tablet batches included in the study. The tablet compression experiment was divided into two sub-experiments. The first was two tablet batches (Batches 9A and 10A) included granules of either 48% (from Batch 9) or 64% (from Batch 10) ticagrelor, respectively. Scale up of the 95% ticagrelor granules showed poor manufacturability in the granulation process step, and therefore these granules were not compressed into tablets, see section conclusions for details.

Secondly, the granule containing 48% ticagrelor (Batch 9) was used for additional five tablet batches (Batches 9B to 9F) where the excipients in the tablet formulation were varied, see Table 7. In one batch colloidal anhydrous silica was excluded (Batch 9B), in one batch the amount of sodium stearyl fumarate was decreased from 1% (w/w) to 0.5% (Batch 9C), and in three batches the quality and quantity of disintegrant was examined. In Batch 9D the amount of disintegrant was increased from 5% (w/w) to 8%, in Batch 9E half the amount of crospovidone was exchanged to croscarmellose sodium, and in Batch 9F the crospovidone, which in all batches so far has been of a super fine particle size quality, was exchanged to a somewhat coarser quality of crospovidone. In the evaluation of the two crospovidone qualities, they are called crospovidone SF (as in super-fine) and crospovidone F (as in fine), respectively.

TABLE 7

Composition of tablet batches

| Components | Tablet batch (granulation batch included in the tablet composition) | | | | | | |
|---|---|---|---|---|---|---|---|
| | 9A | 10A | 9B | 9C | 9D | 9E | 9F |
| Ticagrelor granules | 31.0 | 23.3 | 31.0 | 31.0 | 31.0 | 31.0 | 31.0 |
| F-MELT, type C | 62.8 | 70.5 | 63.0 | 63.3 | 59.8 | 62.8 | 62.8 |
| Crospovidone SF | 5.00 | 5.00 | 5.00 | 5.00 | 8.00 | 2.50 | — |
| Crospovidone F | — | — | — | — | — | — | 5.00 |
| Croscarmellose sodium | — | — | — | — | — | 2.50 | — |
| Sodium stearyl fumarate | 1.00 | 1.00 | 1.00 | 0.50 | 1.00 | 1.00 | 1.00 |
| Silica, colloidal anhydrous | 0.20 | 0.20 | — | 0.20 | 0.20 | 0.20 | 0.20 |

All values are weight percentages.

Scale up of the 95% ticagrelor granule composition (Batch 8) from 100 g to 500 g affected manufacturability during the granulation process step. A lot of material adhered to the vessel walls as well as to the impeller causing strong friction between the impeller and the bottom of the vessel. The process had to be stopped several times to scrape off material. It was judged that the composition would never work in production scale and therefore these granules where never compressed into tablets.

Decreasing the amount of ticagrelor in the granule composition and instead adding mannitol as filler was found to improve the manufacturability, with less adhesion of material to vessel walls and impeller. It was still necessary to stop the process a few times and scrape off some material, but the composition was judged to be processable. Granules containing 64% (Batch 10) and 48% ticagrelor (Batch 9) with mannitol as filler were evaluated and the adhesion of material was more extensive when 64% ticagrelor was used. With granulation batches including 48% ticagrelor, just some material adhered to the vessel and impeller.

Table 8 summarises the results and observations from tablet compression of the different granules. As for the visual observations during compression, the only two batches with manufacturability problems were Batch 9C, where the amount of lubricant was decreased from 1.0% to 0.5% (w/w) that showed moderate flowability and tendencies of picking and sticking, and Batch 9B, where no glidant was included in the formulation and poor flowability was observed during tablet compression. All other batches showed excellent manufacturability. It was therefore concluded that a proper amount of lubricant corresponds to 1.0% (w/w) where no sticking or picking tendencies were observed and the flowability was good and that the amount of silica should be 0.2% (w/w) in order to generate a powder blend with good flowability.

Comparing tablet containing granules of 64% and 48% (w/w) ticagrelor, revealed that a higher amount of ticagrelor in the granules results in a slightly shorter disintegration time, see tablet Batch 9A and tablet Batch 10A. With a higher drug load in the granules, a smaller amount of granules is included in the tablet formulation (that should always carry a set amount of ticagrelor) and hence a larger amount of fast oral disintegrating excipient. Even though a short disintegration time is important for the product, it was decided that Batch 9 including 48% ticagrelor and mannitol as filler should be used for further formulation evaluation studies in view of the manufacturability problems shown in the granulation process step earlier.

Comparing Batch 10A (5% crospovidone SF), with Batch 9D (8% crospovidone SF), Batch 9E (2.5% crospovidone SF and 2.5% croscarmellose sodium), and 9F (5% crospovidone F) revealed that an increase of the disintegrant from 5% to 8% did not shorten the disintegration time, on the contrary it increased from 28 to 43 seconds. Exchanging half of the disintegrant with croscarmellose sodium did not affect the disintegration time (both batches 28 seconds). However, exchanging crospovidone SF with crospovidone F shortened the disintegration time from 28 to 22 seconds and resulted in selection of crospovidone F for use in the tablet composition.

TABLE 8

Observations and results from Example 3

| Quality attributes | 9A 48% gran | 10A 64% gran | 9B No glidant | 9C 0.5% lubric. | 9D 8% C-SF | 9E 2.5% + 2.5% | 9F 5% C-F |
|---|---|---|---|---|---|---|---|
| Flowability | good | good | poor | moderate | good | good | good |
| Picking/Sticking | no | no | no | yes | no | no | no |
| Hardness, n = 10 | | | | | | | |
| Average (N) | 52.6 | 54.3 | 61.8 | 64.8 | 60.3 | 59.1 | 61.6 |
| RSD (%) | 3.68 | 3.29 | 12.2 | 4.80 | 9.90 | 8.41 | 5.11 |

TABLE 8-continued

Observations and results from Example 3

| Quality attributes | 9A 48% gran | 10A 64% gran | 9B No glidant | 9C 0.5% lubric. | 9D 8% C-SF | 9E 2.5% + 2.5% | 9F 5% C-F |
|---|---|---|---|---|---|---|---|
| Tablet weight, n = 10 | | | | | | | |
| Average (mg) | 603.2 | 605.7 | 595.9 | 598.9 | 600.3 | 603.4 | 602.9 |
| RSD (%) | 0.51 | 0.49 | 1.26 | 0.52 | 0.99 | 0.82 | 0.52 |
| Friability (%) | 0.5 | 0.5 | 0.6 | 0.5 | 0.4 | 0.5 | 0.5 |
| Disintegration (s), n = 6 | 31 | 28 | 38 | 29 | 43 | 28 | 22 |

Typically preferred RSD values for the hardness measurements are less than 20%. Typically preferred RSD values for the tablet weight measurements are less than 4.0%. Typically preferred friability values are less than 1.0%. Typically preferred disintegration times are less than 30 seconds.

In summary, the manufacturability of the ticagrelor granules was improved by lowering the ticagrelor content from 95% to 48%. Exchanging the crospovidone to a somewhat coarser quality gave a better margin to meeting the CQA of disintegration. With a lubricant content of 1.0% and a glidant content of 0.2% the flowability during tablet compression was assured and thereby the risk of not meeting the CQA of uniformity of dosage unit was decreased. Based on these results, the tablet composition of Batch 9F was selected for further evaluation, see Table 9.

TABLE 9

Prototype composition of ticagrelor orodispersible tablet, 90 mg

| Components | Quantity per batch (%) | Quantity per tablet (mg) | Function |
|---|---|---|---|
| Ticagrelor[a] | 15.0 | 90.0 | Drug substance |
| F-MELT, type C[b,c] | 62.8 | 377 | Filler |
| Mannitol[a] | 15.0 | 90.0 | Filler |
| Crospovidone[b] | 5.00 | 30.0 | Disintegrant |
| Sodium stearyl fumarate[b] | 1.00 | 6.00 | Lubricant |
| Hydroxypropylcellulose[a] | 0.93 | 5.58 | Binder |
| Silica, colloidal anhydrous[a,b,d] | 0.28 | 1.68 | Glidant/anti-caking agent |
| Water[e] | qs | qs | Granulation liquid |

[a]Included in the granules. The granule consists of ticagrelor (48.4%), mannitol (48.4%), hydroxypropylcellulose (3.00%) silica (0.25%).
[b]Dry-mixed with the ticagrelor granules (31.25%) to form the final tablet composition.
[c]F-MELT type C is a mixture formed by a co-spray drying of mannitol (65%), microcrystalline cellulose (18%), crospovidone (8%), xylitol (5%), and anhydrous dibasic calcium phosphate (4%)
[d]total amount of silica, both intragranular (0.08%) and extragranular (0.20%).
[e]Removed during the manufacturing process
qs quantum satis Example 4—Assessment of Disintegrant Since disintegration is one of the primary characteristics for an orodispersible tablet, Example 4 was set up in order to evaluate quantity and quality of disintegrant to be used.

The lead composition from previous studies included 5% of the disintegrant crospovidone, of a fine particle size grade, here called crospovidone F[1]. It was compared to a crospovidone from another supplier, here called crospovidone F[2] (Table 10). Both have about the same particle size distribution. The amounts included were 0%, 2% and 5% (w/w) crospovidone and the amount was compensated with F-MELT type C in the composition. All batches contained the same batch of ticagrelor granules, with a composition as follows: 48.4% ticagrelor, 48.4% mannitol, 3.00% hydroxypropylcellulose, and 0.25% silica, all expressed in weight percentage.

TABLE 10

Disintegrant in tablet batches

| Batch | Disintegrant (crospovidone) | Amount (wt %) |
|---|---|---|
| 11 | — | 0.0 |
| 12 | Crospovidone F [1] | 5.0 |
| 13 | Crospovidone F [2] | 5.0 |
| 14 | Crospovidone F [1] | 2.0 |
| 15 | Crospovidone F [2] | 2.0 |

Table 11 summaries the outcome of the disintegrant evaluation experiments in Example 4.

TABLE 11

Observations and results

| | Batch (quantity and quality of crospovidone) | | | | |
|---|---|---|---|---|---|
| Quality attributes | 11 0% | 12 5% F [1] | 13 5% F [2] | 14 2% F [1] | 15 2% F [2] |
| Flowability | good | good | good | good | good |
| Picking/Sticking | no | no | no | no | no |
| Hardness, n = 10 | | | | | |
| Average (N) | 63.3 | 61.0 | 65.8 | 62.3 | 58.9 |
| RSD (%) | 7.06 | 6.73 | 10.1 | 4.59 | 5.04 |
| Tablet weight, n = 10 | | | | | |
| Average (mg) | 604.6 | 607.9 | 602.8 | 598.0 | 595.3 |
| RSD (%) | 0.74 | 0.68 | 1.10 | 0.48 | 0.50 |
| Friability (%) | 0.3 | 0.5 | 0.7 | 0.5 | 0.5 |
| Disintegration (s), n = 6 | 29 | 26 | 25 | 21 | 21 |
| Dissolution | | | | | |
| at 45 min (%) | 92.9 | 94.5 | NT | 94.3 | NT |
| at 60 min (%) | 93.9 | 95.4 | NT | 95.2 | NT |

NT not tested

Typically preferred RSD values for the hardness measurements are less than 20%. Typically preferred RSD values for the tablet weight measurements are less than 4.0%. Typically preferred friability values are less than 1.0%. Typically preferred disintegration times are less than 30 seconds. Typically preferred dissolution thresholds are at least 75% at 45 min and at least 80% at 60 min.

As can be seen all five batches showed good manufacturability with good flowability and no picking or sticking to tablet punches. The good flowability is reflected in the low variability in tablet hardness and weight (RSD-value) and all three quality attributes are good indicators for that the risk of not meeting the CQA of uniformity of dosage unit in production scale process is low. Disintegration was clearly affected by the amount of crospovidone. As can be seen 2% of either Crospovidone F[1] or Crospovidone F[2] gave the shortest disintegration time. Comparing dissolution of the tablets containing 0, 2 and 5% crospovidone F[1] revealed that the amount of crospovidone did not appear to have a major impact on the dissolution. In view of these findings it was decided that Crospovidone F[1] should continue to be included in the formulation and that the preferred quantity of crospovidone is closer to 2% than 5%.

Example 5—Assessment of Tablet Composition

The objective of this study was to investigate the tablet composition of the formulation. A 4+3 fractional factorial experimental design was carried out with three factors; amount of sodium stearyl fumarate, colloidal anhydrous silica and crospovidone.

The compositions of the tablet batches in this study are detailed in Table 12. Crospovidone was varied between 1.0 to 4.0% (w/w), sodium stearyl fumarate between 1.0 to 3.0% (w/w) and finally silica between 0.2 to 0.6% (w/w). One granulation batch of 600 g was manufactured to support all tablet compositions in the study. The composition of the granules was as follows: 48.4% ticagrelor, 48.4% mannitol, 3.00% hydroxypropylcellulose, and 0.25% silica, all expressed in weight percentage.

The observations and results from the study are detailed in Table 13. Visual observations during tablet compression such as flowability and picking/sticking were noticed. The tablets were analysed for weight and hardness variation, friability, disintegration, and dissolution. The results were studied and compared individually as well as evaluated using the experimental design tool Modde® (v 9.0 Umetrics AB, Sweden).

As can be seen in Table 13 all seven batches showed good manufacturability with good flowability and no picking or sticking to tablet punches. The good flowability is reflected in the low variability in tablet hardness and weight (RSD-value). All batches met the preferred threshold value for friability.

The results indicated that less of both crospovidone and sodium stearyl fumarate gives shorter disintegration time. The amount of silica did not significantly affect the disintegration time but both sodium stearyl fumarate and silica improved the flowability. Increased amount of both sodium stearyl fumarate and crospovidone gave slightly faster dissolution rate, although all complied with the preferred dissolution thresholds of Q=70 at 45 min and Q=75 at 60 min.

TABLE 12

Composition of tablet batches in Example 5 (% w/w)

| Components | Batch | | | | | | |
|---|---|---|---|---|---|---|---|
| | 16 | 17 | 18 | 19 | 20 | 21 | 22 |
| Ticagrelor granules | 31.0 | 31.0 | 31.0 | 31.0 | 31.0 | 31.0 | 31.0 |
| F-MELT, type C | 63.8 | 64.8 | 66.4 | 61.4 | 64.1 | 64.1 | 64.1 |
| Crospovidone | 4.00 | 1.00 | 1.00 | 4.00 | 2.50 | 2.50 | 2.50 |
| Sodium stearyl fumarate | 1.00 | 3.00 | 1.00 | 3.00 | 2.00 | 2.00 | 2.00 |
| Silica, colloidal anhyd. | 0.20 | 0.20 | 0.60 | 0.60 | 0.40 | 0.40 | 0.40 |
| Total | 100 | 100 | 100 | 100 | 100 | 100 | 100 |

All values are weight percentages.

TABLE 13

Observations and results

| Quality attributes | Batch | | | | | | |
|---|---|---|---|---|---|---|---|
| | 16 | 17 | 18 | 19 | 20 | 21 | 22 |
| Flowability | good | good | good | good | good | good | good |
| Picking/Sticking | no | no | no | no | no | no | no |
| Hardness, n = 10 | | | | | | | |
| Average (N) | 45.8 | 55.4 | 54.1 | 47.2 | 49.6 | 52.3 | 55.0 |
| RSD (%) | 9.21 | 4.97 | 4.49 | 4.98 | 4.49 | 4.81 | 5.57 |
| Tablet weight, n = 10 | | | | | | | |
| Average (mg) | 593 | 604 | 599 | 602 | 592 | 605 | 607 |
| RSD (%) | 1.24 | 0.58 | 0.86 | 0.99 | 0.53 | 0.62 | 0.57 |
| Friability (%) | 0.5 | 0.5 | 0.5 | 0.5 | 0.5 | 0.3 | 0.5 |
| Disintegration (s), n = 6 | 28 | 28 | 23 | 30 | 24 | 25 | 23 |
| Dissolution | | | | | | | |
| at 45 min (%) | 92.5 | 91.3 | 89.9 | 92.9 | 91.0 | NT | NT |
| at 60 min (%) | 93.2 | 92.0 | 90.8 | 93.8 | 91.8 | NT | NT |

NT not tested

Typically preferred RSD values for the hardness measurements are less than 20%. Typically preferred RSD values for the tablet weight measurements are less than 4.0%. Typically preferred friability values are less than 1.0%. Typically preferred disintegration times are less than 30 seconds. Typically preferred dissolution thresholds are at least 75% at 45 min and at least 80% at 60 min.

These findings lead to a tablet composition for further trials where the amount of crospovidone was lowered from 5.0% to 2.0% as it was shown to give the shortest disintegration time, and as both sodium stearyl fumarate and (extragranular) silica improved the flowability the amounts were slightly increased, for sodium stearyl fumarate from 1.00% to 1.50% and for silica from 0.20% to 0.40%.

Example 6—Assessment of Granulation Composition and Drying Method

In order to further investigate the composition of the granules a fractional factorial experimental design with 4+3 trials was carried out. The factors varied were amount of ticagrelor, hydroxypropylcellulose, and colloidal anhydrous silica.

In the studies detailed in Examples 2 to 5, the granules have been tray dried. Duplicates of two trials were carried out where the granules were dried in a fluid bed drier in order to find out if that had any impact on the tablet quality. The use of fluid bed driers is typical in commercial scale manufacture.

The compositions of the granulation trials in the study are detailed in Table 14 below. The content of ticagrelor was varied between 38 and 58%, hydroxypropylcellulose between 2 and 6%, and finally silica between 0.25 and 0.75%. As the tablet should always carry 90 mg ticagrelor, the composition of the tablet included between 25.9 and 39.5% of ticagrelor granules, see Table 15 below. The varying amount of granules was compensated with F-MELT type C in the tablet compositions. As for the other tablet excipients all tablets batches contained 2.0% crospovidone, 1.5% sodium stearyl fumarate and 0.4% silica. All expressed in weight percentage.

TABLE 14

Composition of granule batches

| Components | Batch (Trial number) | | | | | | |
|---|---|---|---|---|---|---|---|
| | 23 N1 | 24 N2 | 25 N3 | 26 N4 | 27 N5 | 28 N6 | 29 N7 |
| Ticagrelor | 38.0 | 58.0 | 38.0 | 58.0 | 48.0 | 48.0 | 48.0 |
| Mannitol | 59.25 | 39.75 | 55.75 | 35.25 | 47.50 | 47.50 | 47.50 |
| Hydroxypropylcellulose | 2.00 | 2.00 | 6.00 | 6.00 | 4.00 | 4.00 | 4.00 |
| Silica, colloidal anhyd. | 0.75 | 0.25 | 0.25 | 0.75 | 0.50 | 0.50 | 0.50 |
| Total | 100 | 100 | 100 | 100 | 100 | 100 | 100 |

All values are weight percentages.

TABLE 15

Composition of tablet batches

| Components | Batch (Trial number)[a] | | | | | | |
|---|---|---|---|---|---|---|---|
| | 30 N1 | 32 N3 | 34 N5 | 35 N6 | 36 N7 | 31 N2 | 33 N4 |
| Ticagrelor granules | 39.47 | | 31.25 | | | 25.86 | |
| F-MELT, type C | 56.63 | | 64.85 | | | 70.24 | |
| Crospovidone | 2.00 | | 2.00 | | | 2.00 | |
| Sodium stearyl fumarate | 1.50 | | 1.50 | | | 1.50 | |
| Silica, colloidal anhyd. | 0.40 | | 0.40 | | | 0.40 | |
| Total | 100 | | 100 | | | 100 | |

[a]Trial Nos. N1 and N3 contains granules of 38% ticagrelor, number N5-N7 granules of 48% ticagrelor and number N2 and N4 granules of 58% ticagrelor.
All values are weight percentages.

Observations during the manufacturing process such as processability during granulation, and flowability as well as picking/sticking during tablet compression were noticed. The tablets were analysed for hardness, weight, friability, disintegration and dissolution. The results were studied and compared individually as well as evaluated using the experimental design tool Modde® (v 9.0 Umetrics AB, Sweden). Table 16 summarise the outcome of the observations and results from Example 6.

During the granulation process, increasing the amount of ticagrelor included in the granules lead to an increase in processing difficulty. The adhesive, cohesive and small sized ticagrelor particles tended to adhere to the walls of the granulator and it was necessary to stop the process and scrape off material from the walls a couple of times during the process. On the other hand, the results from the analysis of the tablets revealed that the larger the amount of ticagrelor in the granules the shorter the disintegration time of the tablets, which occurs as the inclusion of greater amounts of ticagrelor in the granules leads to the need for smaller amounts of granules being included in the tablet formulation and hence more F-MELT which helps the disintegration. These findings confirm the results from Example 3, where granules of 95%, 64% and 48% (w/w) ticagrelor were compared.

The disintegration time was also decreased by adding a larger amount of hydroxypropylcellulose in the granules. This could be explained by that a larger amount of hydroxypropylcellulose makes the granules harder and less prone to crush during tablet compression. Crushing of granules would generate small particles that would bind to F-MELT and thereby increase the disintegration time. It was also shown that a larger amount of hydroxypropylcellulose slightly increased the dissolution rate of ticagrelor.

As can be seen in Table 16 all batches showed good manufacturability with good flowability and no picking or sticking to tablet punches. The good flowability is reflected in the low variability in tablet hardness and weight (RSD-value), all indicating that the risk of not meeting the CQA of uniformity of dosage unit in production scale process is low. It is also noticed that all tablets met the preferred threshold values for friability.

The amount of silica in the granules did not appear to impact the tablet quality, but as a larger amount facilitates the granulation process by reducing the adhesive and/or cohesive nature of ticagrelor particles it was decided that a larger amount of silica was to be included in the granules.

After the study the following changes were made to the granulation composition. The amount of hydroxypropylcellulose was increased from 3.0 to 4.0% as it was shown that a higher amount shortened the disintegration time. The amount of silica in the granules was increased from 0.25% to 0.75% in order to reduce the adhesive and/or cohesive nature of ticagrelor particles. The amount of ticagrelor was not changed as a higher amount appeared to have a negative impact on the processability whereas a smaller amount appeared to have a negative impact on the disintegration time.

TABLE 16

Observations and Results

| Quality attribute | Batch (Trial No (amount ticagrelor in granules)) | | | | | | |
|---|---|---|---|---|---|---|---|
| | 30 N1 (38%) | 31 N2 (58%) | 32 N3 (38%) | 33 N4 (58%) | 34 N5 (48%) | 35 N6 (48%) | 36 N7 (48%) |
| Flowability | good | good | good | good | good | good | good |
| Picking/Sticking | no | no | no | no | no | no | no |
| Hardness, n = 10 | | | | | | | |
| Average (N) | 56.7 | 59.6 | 47.4 | 50.6 | 48.8 | 50.8 | 54.7 |
| RSD (%) | 8.64 | 4.36 | 5.70 | 5.73 | 6.97 | 5.91 | 5.30 |
| Tablet weight, n = 10 | | | | | | | |
| Average (mg) | 604.5 | 610.6 | 605.5 | 601.5 | 599.3 | 593.5 | 603.9 |
| RSD (%) | 0.61 | 0.24 | 0.54 | 0.53 | 0.55 | 0.62 | 0.63 |
| Friability (%) | 0.3 | 0.5 | 0.3 | 0.5 | 0.5 | 0.5 | 0.3 |
| Disintegration (s), n = 6 | 31 | 22 | 26 | 23 | 24 | 26 | 23 |
| Dissolution | | | | | | | |
| at 45 min (%) | 92.3 | 88.7 | 95.2 | 93.1 | NT | 93.7 | NT |
| at 60 min (%) | 93.5 | 90.1 | 95.8 | 94.3 | NT | 94.5 | NT |

NT not tested

Typically preferred RSD values for the hardness measurements are less than 20%. Typically preferred RSD values for the tablet weight measurements are less than 4.0%. Typically preferred friability values are less than 1.0%. Typically preferred disintegration times are less than 30 seconds. Typically preferred dissolution thresholds are at least 75% at 45 min and at least 80% at 60 min.

Tables 17 and 18 below show the analysis of the granules and tablets containing the granules that were either tray dried or fluid bed dried. The granules in N1 and N1b contain 38% ticagrelor, whereas the granules in N4 and N4b contain 58% ticagrelor. N1 and N4 are tray dried and N1b and N4b are fluid bed dried. As can be seen in Table 17, N4 and N4b have a larger particle size distribution than N1 and N1b but in both cases does fluid bed drying generate smaller particles than tray drying which also results in a higher Carr's index for both the fluid bed dried granules. On the other hand the two drying methods generate no major difference in tablet quality, see Table 18. Hence it was found that fluid bed drying is potentially suitable for commercial manufacturing without significantly affecting tablet quality.

TABLE 17

Comparing tray dried and fluid bed dried granules

| | Granule Batch | | | |
|---|---|---|---|---|
| | 23 | 23A | 26 | 26A |
| Trial No | N1 | N1b[a] | N4 | N4b[a] |
| Carr's index (%) | 29.1 | 32.0 | 31.3 | 33.3 |
| Particle size distribution | | | | |
| d (0.1) | 8.05 | 6.64 | 7.70 | 7.18 |
| d (0.5) | 73.0 | 57.3 | 194 | 132 |
| d (0.9) | 874 | 709 | 1168 | 1020 |

[a]Trial Nos. N1b and N4b contain fluid bed dried granules (Trial Nos. N1 and N4 contain tray dried granules)

TABLE 18

Comparing tablets containing either tray dried or fluid bed dried granules

| | Tablet Batch | | | |
|---|---|---|---|---|
| | 30 | 30A | 33 | 33A |
| Trial No | N1 | N1b[a] | N4 | N4b[a] |
| Flowability | good | good | good | good |
| Picking/Sticking | no | no | no | no |
| Hardness, n = 10 | | | | |
| Average (N) | 56.7 | 55.8 | 50.6 | 56.8 |
| RSD (%) | 8.64 | 9.89 | 5.73 | 5.85 |
| Tablet weight, n = 10 | | | | |
| Average (mg) | 604.5 | 614.5 | 601.5 | 610.9 |
| RSD (%) | 0.61 | 1.28 | 0.53 | 0.70 |

TABLE 18-continued

Comparing tablets containing either tray dried or fluid bed dried granules

| | Tablet Batch | | | |
|---|---|---|---|---|
| | 30 | 30A | 33 | 33A |
| Friability (%) | 0.30 | 0.45 | 0.45 | 0.30 |
| Disintegration (s), n = 6 | 31 | 30 | 23 | 26 |
| Dissolution at 45 min (%) | 92.6 | 91.8 | 93.1 | 91.3 |

[a]N1b and N4b contain fluid bed dried granules (N1 and N4 contain tray dried granules)

Example 7—Tablet Compositions

The composition shown in Table 19A has been prepared and is intended to illustrate the invention.

TABLE 19A 90 mg Ticagrelor Tablet Composition

| Ingredient | Quantity per batch (%) | Quantity per tablet (mg) |
|---|---|---|
| Ticagrelor[a] | 15.0 | 90.0 |
| F-MELT type C[b,c] | 64.8 | 389 |
| Mannitol[a] | 14.8 | 88.6 |
| Crospovidone[b] | 2.00 | 12.0 |
| Sodium stearyl fumarate[b] | 1.50 | 9.00 |
| Hydroxypropylcellulose[a] | 1.25 | 7.50 |
| Silica, colloidal anhydrous[a,b,d] | 0.63 | 3.81 |
| Core tablet weight | 100 | 600 |

[a]Included in the granules. The granule consists of ticagrelor (48.0%), mannitol (47.25%), hydroxypropylcellulose (4.00%) silica (0.75%).
[b]Dry-mixed with the ticagrelor granules (31.25%) to form the final tablet composition.
[c]F-MELT type C is a mixture formed by a co-spray drying of mannitol (65%), microcrystalline cellulose (18%), crospovidone (8%), xylitol (5%), and anhydrous dibasic calcium phosphate (4%)
[d]total amount of silica, both intragranular (0.23%) and extragranular (0.40%).
[e]Removed during the manufacturing process
qs quantum satis The composition shown in Table 19B may also be prepared.

TABLE 19B 60 mg Ticagrelor Tablet Composition

| Ingredient | Quantity per batch (%) | Quantity per tablet (mg) |
|---|---|---|
| Ticagrelor[a] | 15.0 | 60.0 |
| F-MELT type C[b,c] | 64.8 | 259 |
| Mannitol[a] | 14.8 | 59.1 |
| Crospovidone[b] | 2.00 | 8.00 |
| Sodium stearyl fumarate[b] | 1.50 | 6.00 |
| Hydroxypropylcellulose[a] | 1.25 | 5.00 |
| Silica, colloidal anhydrous[a,b,d] | 0.63 | 2.54 |
| Core tablet weight | 100 | 400 |

[a]Included in the granules. The granule consists of ticagrelor (48.0%), mannitol (47.25%), hydroxypropylcellulose (4.00%) silica (0.75%).
[b]Dry-mixed with the ticagrelor granules (31.25%) to form the final tablet composition.
[c]F-MELT type C is a mixture formed by a co-spray drying of mannitol (65%), microcrystalline cellulose (18%), crospovidone (8%), xylitol (5%), and anhydrous dibasic calcium phosphate (4%)
[d]total amount of silica, both intragranular (0.23%) and extragranular (0.40%).
[e]Removed during the manufacturing process
qs quantum satis Example 8—Tablet Manufacture 600 mg tablets containing 90 mg ticagrelor, according to Example 7, were manufactured according to the following method. Silica, colloidal anhydrous, ticagrelor, hydroxypropylcellulose and mannitol were dry mixed in a high shear mixer for about 5 minutes to give a total mass of 9 kg of dry ingredients. Then, a wet granulation was carried out by adding a granulating liquid (water, 18.4% (w/w)) to the dry ingredients. The wet granule mix was milled in a rotating impeller screening mill and then dried in a fluid bed dryer with an inlet air drying temperature of 50° C. This was followed by milling in a rotating impeller screening mill. Final blending was performed in a diffusion mixer. Ticagrelor-containing granules, silica, colloidal anhydrous, F-MELT type C, crospovidone and sodium stearyl fumarate were then blended together for about 20 minutes. The final blend was compressed into tablets using a power assisted tablet press.

Tablet compaction forces of between 7.9 kN and 13.1 kN were found to be sufficient to provide tablets having an appropriate hardness (approximately 65N). These tablets had acceptable disintegration time, dissolution rate, hardness, and friability values.

This process has also been scaled up using batch sizes of the final blend in the region of 256 kg. These tablets also had acceptable disintegration time, dissolution rate, hardness, and friability values.

Example 9—Assessment of Drug Particle Size and Manufacturing Parameters on Tablet Properties The impact of (i) drug substance particle size, (ii) granulation liquid amount and (iii) water addition time on tablet manufacture were evaluated. The tablet composition was in accordance with Example 7, and the manufacturing method was in line with Example 8 except where specified otherwise. The tablets produced in this study were round and flat bevelled edged, 14 mm in size. 8 out of the 10 batches tested were also embossed.

Two drug substance batches were selected with a low and high D (v, 0.9) value. The water addition time was varied by using 2 or 4 spray nozzles. The experimental design is outlined in Table 20. The major responses were assay, Acceptance Value (AV) for content variation, disintegration and dissolution.

TABLE 20

Experimental design for the granulation step

| | Drug substance | | Water addition | |
|---|---|---|---|---|
| Batch | particle size, D (v, 0.9), μm | Water amount, kg | Calculated time, minutes | Number of nozzles |
| 37 | 22 | 10 | 4.3 | 4 |
| 38 | 11 | 12 | 10.3 | 2 |
| 39 | 22 | 10 | 4.3 | 4 |
| 40 | 22 | 10 | 8.6 | 2 |
| 41 | 11 | 10 | 8.6 | 2 |
| 42 | 11 | 12 | 5.2 | 4 |
| 43 | 22 | 12 | 5.2 | 4 |
| 44 | 11 | 10 | 4.3 | 4 |
| 45 | 11 | 12 | 10.3 | 2 |
| 46 | 22 | 12 | 10.3 | 2 |

All batches were sampled at three or four different compaction forces prior to commencing tablet batch compression. In addition, disintegration was analysed for each compaction force. Tablet hardness was tested as diametric compression breaking force.

The sample tablets were withdrawn for UoDU from a composite sample and the AV value was calculated.

In addition, the tablets were sampled and analysed according to the method proposed by Garcia (Garcia, Thomas et. al. Recommendations for the assessment of blend and content uniformity: modifications to withdrawn FDA draft stratified sampling guidance, *J. Pharm. Innov.*, 2014, (DOI) 10.1007/s12247-014-9207-0), see below. Samples from 40 locations were withdrawn, 20 locations were selected for analysis (n=3). The samples were assayed for 4 of the 10 batches.

To meet the acceptance criteria for blend uniformity, according to Garcia, the RSD of all individual results should be ≤3.0% (n=1 on 10 locations) or ≤5.0% (n=3 on 10 locations provided that the reason is not of analytical or sampling error). This criterion was used to gain knowledge to assess homogeneity.

Sampling and analysis for appearance was performed at 4 to 5 occasions. For disintegration and friability sampling and analysis was performed at approximately 5 occasions.

Analyses of dissolution were performed from a composite sample.

Final Blend

The overall objective of the final blend is to produce a uniform blend which can be compressed into tablets consistently containing the required dose of ticagrelor. Four batches were analysed, comprising trials with low/high water amount, small/large particle size drug substance and short/long water addition time. The results of the powder blend uniformity, shown in Table 21, confirms that the powder blend is adequately homogenous after final blend.

TABLE 21

Final blend assay

| Batch | Assay, % of nominal | Minimum, % of nominal | Maximum, % of nominal | SD, % of target |
|---|---|---|---|---|
| 39 | 96.9 | 93.3 | 101.0 | 2.4 |
| 53 | 98.1 | 95.6 | 100.2 | 1.4 |
| 44 | 98.3 | 95.2 | 102.2 | 2.4 |
| 46 | 99.1 | 95.4 | 103.5 | 2.5 |

Tablet Compression

The purpose of this unit operation was to compress the blended powder into tablets that consistently provide the target CQAs. Tablet properties results include assay and UoDU, weight, hardness, thickness, friability, disintegration and dissolution.

Assay and Uniformity of Dosage Units

In order to assess UoDU more thoroughly an assessment based on the method suggested by Garcia was used:

All individual assay results should be within the range of 75.0% to 125.0% of target strength.

Pass the ASTM E2709/E2810 using an acceptance criterion of 90% confidence and 95% coverage for the total number of dosage units assayed.

All batches that were evaluated with this method were successful in meeting the criteria, see Table 22.

TABLE 22

Individual Assay and acceptance test of ASTM E2709/E2810

| Batch | sample locations assayed | Average, % of nominal | Acceptance interval for average[a] | Min. individual tablets, % of nominal | Max. individual tablets, % of nominal | Pass or Fail acceptance test |
|---|---|---|---|---|---|---|
| 39 | 20 | 97.2 | 94.1-105.9 | 93.0 | 104.6 | Pass |
| 53 | 20 | 97.4 | 96.2-103.8 | 90.5 | 106.8 | Pass |
| 44 | 20 | 98.8 | 90.8-109.2 | 95.4 | 103.7 | Pass |
| 46 | 40 | 97.8 | 96.2-103.8 | 87.5 | 107.1 | Pass |

[a]Calculated interval for batch mean that would pass the acceptance test, based on the number of assayed tablets and their content distribution.

The assay results are shown in Table 23. The results show that all batches except one were within an assay interval of 95% to 105%.

TABLE 23

Assay

| Batch | Sample | Average, % of nominal | Min, % of nominal | Max, % of nominal | RSD, % |
|---|---|---|---|---|---|
| 37 | Composite | 97.2 | 94.6 | 101.7 | 2.2 |
| 38 | Composite | 98.6 | 92.8 | 109.0 | 4.7 |
| 39 | Composite | 94.5 | 88.4 | 97.2 | 3 |
| 40 | Composite | 98.1 | 90.2 | 102.8 | 3.4 |
| 41 | Composite | 97.4 | 92.4 | 100.5 | 2.1 |
| 42 | Composite | 100.6 | 94.5 | 107.1 | 4.4 |
| 43 | Composite | 97.4 | 93.2 | 101.8 | 2.9 |
| 44 | Composite | 99.4 | 97.1 | 102.9 | 2 |
| 45 | Composite | 95.4 | 91.1 | 98.8 | 2.8 |
| 46 | Composite | 97.5 | 91.1 | 98.8 | 3.3 |

Tablet Weight

The results are shown in Table 24 below. The batches were within 571 mg to 615 mg and had a mean value between 597 and 602 mg. The low variation in tablet weight indicates good powder flow which contributes to the ability of consequently deliver the right amount of ticagrelor in the final product.

TABLE 24

Tablet weights

| Batch | Mean, mg | Min, mg | Max, mg | RSD, % |
|---|---|---|---|---|
| 37 | 597 | 571 | 614 | 1.0 |
| 38 | 599 | 587 | 608 | 0.8 |
| 39 | 598 | 584 | 607 | 0.9 |
| 40 | 597 | 583 | 604 | 0.7 |
| 41 | 598 | 586 | 610 | 0.9 |
| 42 | 601 | 587 | 615 | 0.9 |
| 43 | 599 | 580 | 613 | 0.9 |
| 44 | 602 | 586 | 613 | 0.8 |
| 45 | 600 | 584 | 610 | 1.0 |
| 46 | 600 | 588 | 611 | 0.9 |

Tablet Hardness, Thickness, Friability, and Disintegration

The tablet hardness and disintegration in relation to compaction force was studied by obtaining a compaction profile for each batch, see Table 25.

TABLE 25

Disintegration time in seconds (n = 6) as a function of compaction force

| Batch | 8 kN | 11 kN | 14 kN |
|---|---|---|---|
| 37 | 20 | 23 | 26 |
| 38 | 24 | 22 | 26 |
| 39 | 21 | 23 | 28 |

TABLE 25-continued

Disintegration time in seconds (n = 6) as a function of compaction force

| Batch | 8 kN | 11 kN | 14 kN |
|---|---|---|---|
| 40 | 21 | 26 | 29 |
| 41 | 18 | 19 | 23 |
| 42 | 18 | 18 | 18 |
| 43 | 19 | 21 | 21 |
| 44 | 23 | 24 | 29 |
| 45 | 18 | 20 | 22 |
| 46 | 16 | 18 | 24 |

The compaction forces needed to obtain a hardness of 65N were between 7.9 kN to 13.1 kN between the batches. It was found that the more fine sized material, measured as D (v, 0.1) in the drug substance granules the lower the compaction force was to achieve the same tablet hardness, here 65 N.

The tablet disintegration time for all batches during the continuous tablet compression run was below the CQA target of 30 seconds. The disintegration dependence of compaction force is shown in Table 25 above. There is a slight curvature with a minimum approximately at the press force used for each batch.

During the continuous batch manufacture the tablet average hardness and friability were monitored. The results are shown in Table 26.

TABLE 26

Tablet hardness, friability and thickness

| Batch | Mean (N) | Min (N) | Max (N) | RSD (%) | Friability (%, n = 11) | Thickness, mm | RSD, % |
|---|---|---|---|---|---|---|---|
| 37 | 67 | 51 | 73 | 7.5 | 0.1 | 3.80 | 0.6 |
| 38 | 66 | 57 | 74 | 6.6 | 0.1 | 3.70 | 0.3 |
| 39 | 61 | 46 | 72 | 8.2 | <0.1 | 3.85 | 0.4 |
| 40 | 64 | 51 | 71 | 7.5 | <0.1 | 3.80 | 0.3 |
| 41 | 64 | 56 | 70 | 6.7 | <0.1 | 3.78 | 0.5 |
| 42 | 63 | 55 | 75 | 8.3 | <0.1 | 3.76 | 0.4 |
| 43 | 61 | 50 | 67 | 7.4 | <0.1 | 3.83 | 0.6 |
| 44 | 64 | 57 | 70 | 5.2 | 0.1 | 3.84 | 0.4 |
| 45 | 63 | 49 | 70 | 8.3 | <0.1 | 3.75 | 0.3 |
| 46 | 68 | 58 | 84 | 8.6 | 0.1 | 3.75 | 0.3 |

The tablet friability was 0.1% or less which is low in comparison with the requirement in the pharmacopeia (<1.0%). The disintegration time was below the CQA target for all batches.

The results show only a small variation between and within batches. The height was 3.7 to 3.8 mm in general. The slightly greater thickness in these tablets compared to earlier tested tablets is due to a short granulation time and low granulation liquid amount, which gives less dense granules and smaller particle sizes. Less compaction is needed to obtain the target hardness of 65 N used for these studies, hence the slightly thicker tablet.

To conclude, the low variation in tablet height is an indicator of the product robustness with respect to the evaluated changes of scale, process parameter settings and drug substance particle size.

Tablet Appearance

The appearance of the tablets was visually assessed. Edge damage related to the adjustment of the scrape off mechanism was discovered in a few cases, after the adjustment damages disappeared. Hardly visible spots of slightly pink colour have been seen in one case and were most likely related to the drug substance colour. Overall there were no observations of picking, sticking, capping or lamination for any of the batches.

Tablet Dissolution

The amount of dissolved ticagrelor after 45 and 60 minutes is summarised in Table 27.

TABLE 27

Dissolution at 45 and 60 minutes, % of label claim, (n = 6)

| Batch | Mean | Min | Max | Mean | Min | Max |
|---|---|---|---|---|---|---|
|  | 45 minutes | | | 60 minutes | | |
| 37 | 83 | 81 | 87 | 85 | 83 | 89 |
| 38 | 82 | 80 | 84 | 85 | 82 | 87 |
| 39 | 84 | 82 | 88 | 86 | 84 | 90 |
| 40 | 81 | 79 | 83 | 83 | 81 | 85 |
| 41 | 85 | 80 | 88 | 87 | 82 | 90 |
| 42 | 84 | 81 | 88 | 86 | 83 | 91 |
| 43 | 85 | 80 | 87 | 87 | 84 | 89 |
| 44 | 89 | 87 | 92 | 91 | 89 | 94 |
| 45 | 84 | 81 | 88 | 87 | 84 | 92 |
| 46 | 83 | 82 | 86 | 85 | 84 | 89 |

The amount of dissolved ticagrelor met the target in all batches. It was noted that the granulation factors that were evaluated influenced the dissolution rate slightly. Increased dissolution appears to come from a short granulation time, a low amount of granulation liquid and a drug substance with small particle size.

Conclusion of Tablet Compression

The results show that tablet compression step is adequate to compress the blended powder into tablets that provide the target Critical Quality Attributes (CQAs). In addition, the use of punch tools with embossing in this study appeared to have no impact on the tablet quality.

Example 10—Assessment of Tablet Dissolution Mechanism

Focused beam reflectance measurements were conducted on a series of ticagrelor granules and F-melt type C granules, each with a range of particle sizes.

Tablet Dissolution Mechanism

In the FBRM apparatus, the probe diameter was approximately 6 mm and had a sapphire window at the probe end. The integration time was set to 5 seconds. The instrument was set on "coarse mode" and focal spot scan rate on 2 m/sec. The probe was placed 2 cm above the paddle and slightly tilted towards the flow. The primary data set contains full particle size distributions 1-1000 μm at 5 sec time resolution. From that dataset kinetic curves were calculated showing different size fractions and the fraction 40-100 μm was the fraction selected for comparison. This fraction was selected since the amount of counts was higher for this fraction. In addition, the variability in between the kinetic profiles was low for the fractions with larger amounts of counts.

The measurements were conducted with a UV probe that was placed in the bath having a 2 mm gap. Dissolution media was 900 ml of water with 0.2% tween 80. 75 rpm paddle speed. In addition a FBRM probe was placed in the bath in order to simultaneously measure the particles in the bath.

Figure 4:
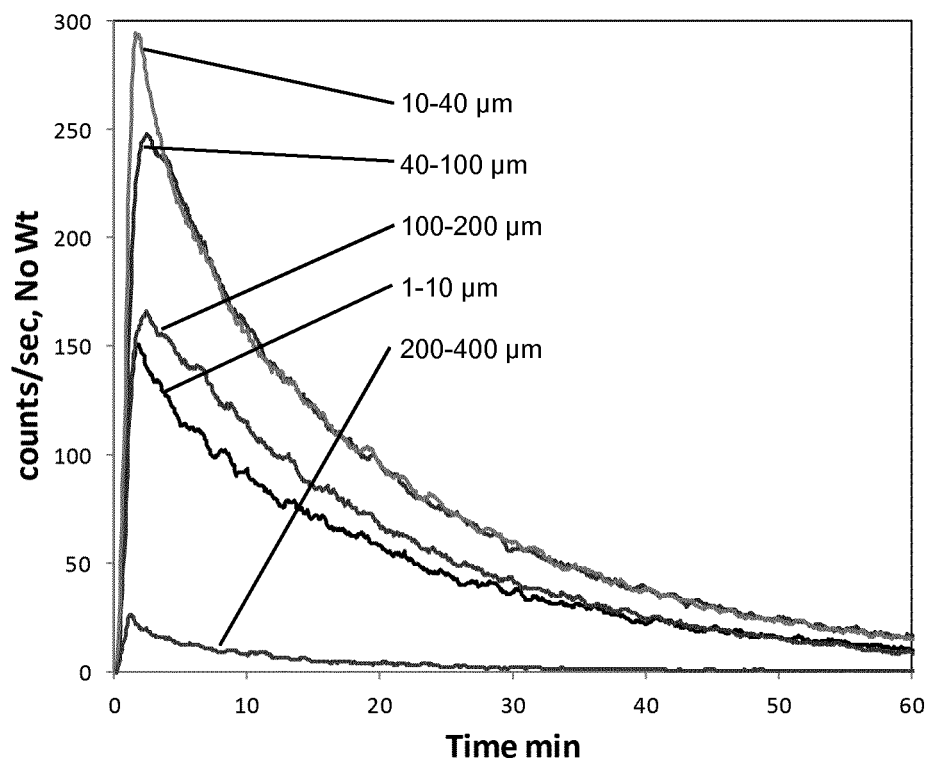
FIG. 4 shows FBRM data for ticagrelor granules.
Figure 5:
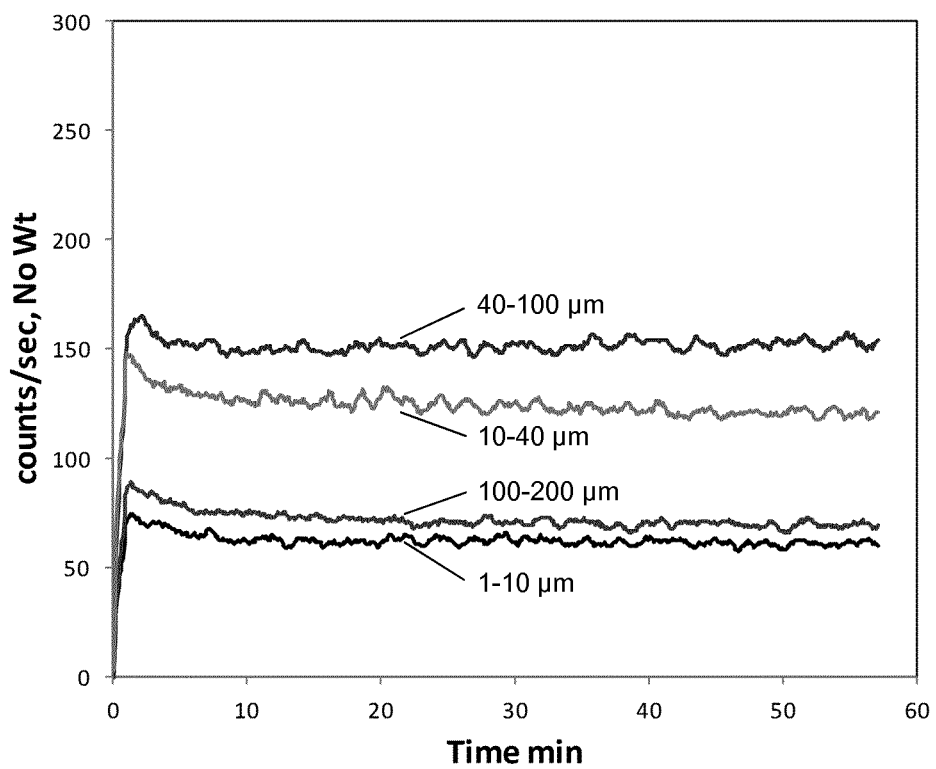
FIG. 5 shows FBRM data for F-Melt granules.

The results are shown in FIGS. 4 and 5.

The FBRM results in FIG. 4 show different particle size fractions from API granules in the dissolution bath. For all sizes the amount of counts are initially increasing in the bath and thereafter decreasing to only a few percent after 60 min. The initial increase in counts depend on that the granules are added to the bath at time zero and the kinetic of dissolving the particles is slower than the time it takes for the particles to be distributed in the bath. The time where the peak of counts appear would probably be different dependent on the way and time the granules are added to the bath and hence it is not relevant where on the time-axis the peak appears. However, the kinetics of the decreasing slopes indicates at what rate the particles dissolve and hence it can be seen that the dissolution of particles is faster during the first 30 min and thereafter the kinetic is slower.

The FBRM results in FIG. 5 show different particle size fractions from F-melt in the dissolution bath. For all sizes an initial increase in amount of particles can be seen during the first minutes, thereafter a small decrease during a few minutes before the number of counts stays at a somewhat constant value. The initial increase in counts depends on that the granules are added to the bath at time zero. However, the almost constant value of particles after that indicates that the dissolution of the F-melt particles is happening quite fast, during the first minutes and simultaneously as the particles are distributed in the bath and therefore a further decrease in counts of particles is not observed. This seems to be in line with the material of F-melt that to a large extent contains spray dried mannitol and hence is designed to dissolve fast.

In summary, tablet dissolution is found to be dominated by the API granule properties, whereas F-Melt is causing the rapid disintegration typical of an orodispersible tablet. It is therefore important to prevent aggregation of the API particles during disintegration and dissolution.

Influence of Storage

Figure 6:
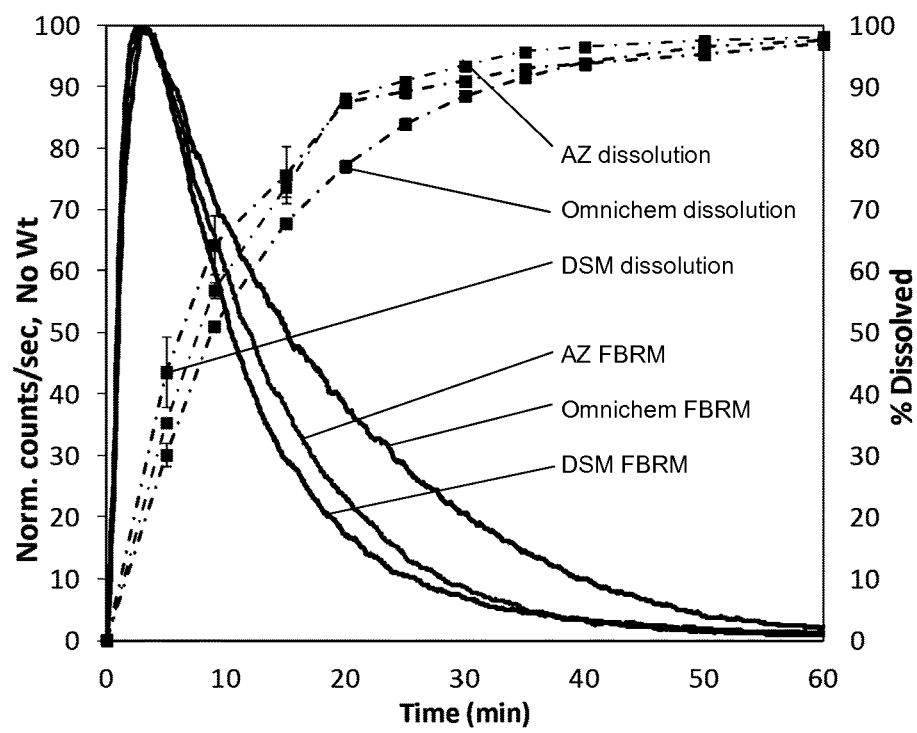
FIG. 6 shows FBRM and dissolution data for batches of ticagrelor prior to storage.
Figure 7:
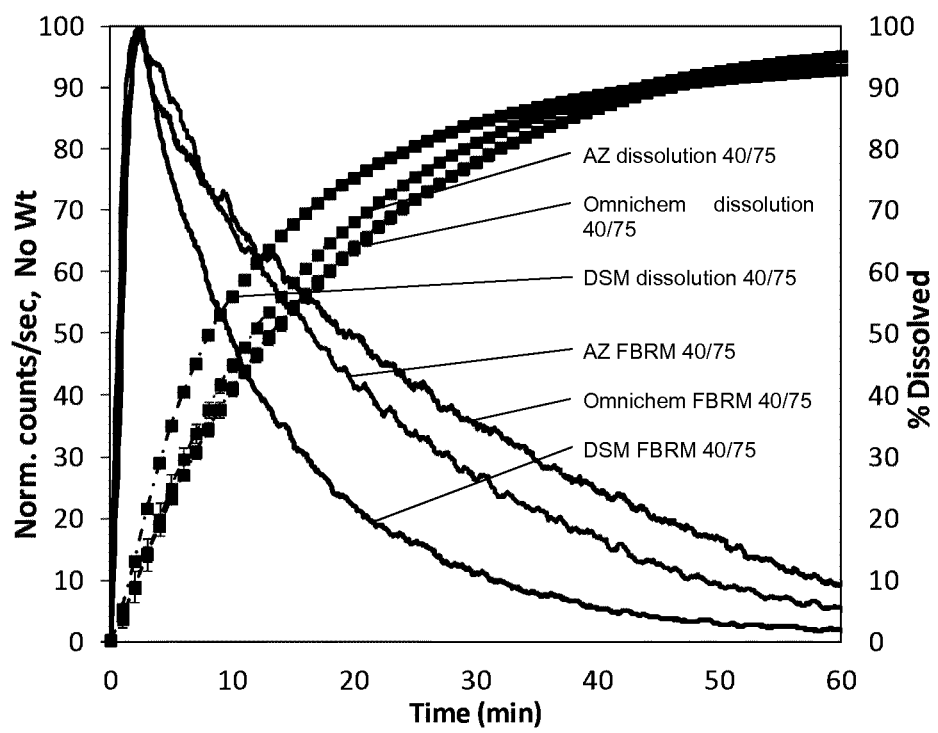
FIG. 7 shows FBRM and dissolution data for batches of ticagrelor following storage at 40° C., 75% RH.

Model granules containing ticagrelor were stored in 40° C. at 75% relative humidity (RH) for 1 month in order to study the dissolution behaviour using the FBRM method described above. Fresh, i.e. non-stored ("model"), granules were prepared for comparison. The results are shown in FIGS. 6 and 7. Ticagrelor particles were received from three different suppliers: supplier 1 ("AZ"); supplier 2 ("DSM"); supplier 3 ("Omnichem").

For both the model granule batch and the stored granule batch containing ticagrelor supplied by "AZ", both profiles show an increase in particles followed by a decrease in counts. However, for the material that has been stored at 40° C. and 75% RH for one month, a slower particle dissolution is observed. In addition, there are more particles left in the bath after 60 mins from the stored material. A similar overall pattern was observed for the material supplied by the other suppliers. The slower particle dissolution from the material that had been stored correlates to the release rates of ticagrelor. A comparison of the data shown in FIGS. 6 and 7 shows that ticagrelor has a slower release from granules that have been in storage for one month compared to the non-stored granules.

In summary, it was found that the behaviour of the model granules containing ticagrelor following storage matched that of the aged tablets. From this, it was concluded that the drug granules cause dissolution changes in aged in tablets.

Example 11—Effect of Storage on Drug Granule Porosity

The pore volume and the pore size distribution were determined using mercury intrusion porosimetry (Micromeritics AutoPore III 9410). The determination was performed within the pore diameter interval 115 µm≥ϕ≥0.0030 µm (30 Å). The surface tension and the contact angle of mercury are set to 485 mN/m and 130°, respectively. Blank correction has been used to compensate for compaction of parts of the penetrometer system at high pressures. The test materials used were: ticagrelor granules ("3606"), final tablet blend ("3606 FB"); F-melt type C granules ("F-melt"); Ticagrelor particles from supplier 1 ("AZ"); Ticagrelor particles from supplier 2 ("DSM"); Ticagrelor particles from supplier 3 ("Omnichem").

To ensure that the porosimeter shows correct intrusion a test with an alumina silica reference material was done prior to the analyses. One of the penetrometers used for analysis of the granules was used for the reference test. The result gave a cumulative pore volume of 0.55 cm³/g and a median pore diameter (based on volume) of 73 Å. The reference values are 0.56±0.02 cm³/g and 75±5 Å, respectively. Results are shown in Table 28.

TABLE 28

Hg porosity data for test materials before and after storage (1 month at 40° C./75% RH)

| | Specimen | Pore volume, cm³/g | | Median pore diameter (vol), µm | | Median pore diameter (area), µm/Å | | Pore area, m²/g | |
| --- | --- | --- | --- | --- | --- | --- | --- | --- | --- |
| | | >8 | <8 | >8 | <8 | >8 | <8 | >8 | <8 |
| Pre-storage | 3606 | 0.53 | 0.22 | 41 | 0.6 | 28 | 42 | <0.1 | 10 |
| | 3606 FB | 0.67 | 0.28 | 29 | 1.8 | 20 | 43 | 0.1 | 10 |
| | AZ | 0.62 | 0.23 | 24 | 0.9 | 21 | 45 | 0.1 | 14 |
| | DSM | 0.59 | 0.28 | 19 | 1.2 | 15 | 44 | 0.1 | 13 |
| | Omnichem | 0.53 | 0.28 | 35 | 0.5 | 26 | 41 | <0.1 | 12 |
| | F-melt | 0.76 | 0.23 | 25 | 2.9 | 19 | 41 | 0.1 | 3 |
| Post-storage (1 month) | 3606 | 0.55 | 0.20 | 40 | 0.6 | 24 | 39 | <0.1 | 8 |
| | 3606 FB | 0.69 | 0.26 | 35 | 1.7 | 28 | 40 | <0.1 | 8 |
| | AZ | 0.69 | 0.23 | 27 | 1.1 | 21 | 41 | 0.1 | 14 |
| | DSM | 0.64 | 0.29 | 20 | 1.5 | 16 | 41 | 0.1 | 12 |
| | Omnichem | 0.61 | 0.18 | 36 | 0.5 | 26 | 38 | <0.1 | 9 |
| | F-melt | 0.80 | 0.21 | 28 | 1.6 | 23 | 44 | 0.1 | 5 |

Hg porosity data for granules coupled with the data in Example 10 indicates that decreased porosity and/or increased aggregation causes a decrease in the dissolution rate for aged tablets. Drug particle size and particle surface properties appear to interact with wet granulation process parameters resulting in a specific aggregation size distribution, which in turn affects tablet dissolution.

Example 12—Effect of Particle Size on Dissolution Following Storage

Four tablet batches were assessed to study the effects of particle size on tablet dissolution rates before and after storage.

The tablets were made according to the composition in Example 7. Parameters associated with the API (D (v, 0.9)) and the tablet manufacture (granulation fluid and mixing time) are shown in Table 29.

TABLE 29 effect of porosity on dissolution following storage

| Batch | 38 | 40 | 43 | 44 |
| --- | --- | --- | --- | --- |
| DOE local. | D (v, 0.9) 11 µm 12 kg H₂O 10 min | D (v, 0.9) 22 µm 10 kg H₂O 8.6 min | D (v, 0.9) 22 µm 12 kg H₂O 5.2 min | D (v, 0.9) 11 µm 10 kg H₂O 4.3 min |

TABLE 29-continued effect of porosity on dissolution following storage

| Batch | 38 | 40 | 43 | 44 |
|---|---|---|---|---|
| Dissolution data | | | | |
| 0 month data, 45 min | 82.9 | 83.4 | 84.0 | 86.7 |
| 40° C., 75RH, 1 month open, 45 min | 72.0 | 73.1 | 73.0 | 77.8 |
| 40° C., 75RH, 1 month closed, 45 min | 76.0 | 77.0 | 77.9 | 81.0 |
| Porosity data | | | | |
| Porosity (<8 um) 0 month data | 0.411 | 0.588 | 0.516 | 0.572 |

The reduction in dissolution following 1 month of storage was typically no more than about 10 to 11%, though in Batch 44 the reduction was about 7%.

Example 13—Effect of Ticagelor Particle Size and Surface Properties

This study was conducted to assess the possible effects of raw material variability between suppliers, mainly physical characteristics such as particle size/habit and surface properties on tablet quality and disintegration time.

The batches of drug substances tested are shown in Table 30.

TABLE 30

Drug substance batches

| Supplier | Batch | Particle Size (μm) D (v, 0.1)/D (v, 0.5)/D (v, 0.9) |
|---|---|---|
| AZ Ops (EFA) | 128 | 3/8/19 |
| | AAUA | 3/7/18 |
| | AAAU | 3/7/18 |
| | AAAS | 3/8/23 |
| Omnichem (AOC) | 605770005 | 2/5/13 |
| | 605770021A | 2/6/14 |
| DSM | LHCYAA4005 | 3/5/9 |
| | LHCYAA5002 | 3/6/10 |

TOF-SIMS surface characterization was conducted on the various drug batches. TOF-SIMS spectra were acquired in positive and negative ion modes in high mass resolution mode for all powders. TOF.SIMS (ION-TOF GmbH, Germany) was used for the experiments. 30 keV $Bi_3^+$ ion clusters were the primary ions. An electron flood gun was used for charge compensation of the sample surface.

The samples were analysed as-received by dropping the powder from a mini-spatula onto double-sided tape on a 1 cm² aluminium plate. The plates were vibrated to allow the powders to settle onto the tape. The excess powder was blown away by clean $CO_2$. These samples were: batch 12801, batch AAAU, Omnichem batch 300000-01, and DSM batch LHCYAA4005. In addition to being analysed as received, DSM batch LHCYAA4005 was cryomilled by hand in a mortar filled with liquid nitrogen to expose the interior of the particles. The cryomilled powder which resulted was mounted as with the as-received powders.

The high mass resolution spectra of the as-received samples were obtained from 500 μm×500 μm areas with 128×128 pixels. The high mass resolution spectra of the cryomilled powder were obtained from 200 μm×200 μm areas with 64×64 pixels. The nominal primary beam size in high mass resolution mode is approximately 5-6 μm.

Additionally, high spatial resolution images were obtained of the DSM batch LHCYAA4005 powder before and after cryomilling. The high spatial resolution images were 200 μm×200 μm (at 1024×1024 pixels) for the as-received sample and 100 μm×100 μm (at 512×512 pixels) for the cryomilled sample. Thus, all images were matched to the nominal 0.2 μm primary beam diameter of high spatial resolution mode.

The data analysis was performed using the software provided by the instrument supplier (Surface Lab 6.3, Measurement Explorer, ION-TOF GmbH, Germany).

Particle Size Distribution: about 3 ml dry powder was measured at 0.1 bar using a Malvern Mastersizer 2000.

Ticagrelor powders are characterised by poor flowability, for example as indicated by a large Hausner ratio (tap density/bulk density ~1.8-2.0). Particle size distributions (PSD) typical for the three drug substance manufacturers are given in Table 30.

The larger D (v, 0.9) size fraction detected for AZ Ops supply corresponds to a more extended particle habit which, in turn, gives the lowest flowability (highest Hausner ratio).

For the ticagrelor rapidly disintegrating formulation, drug substance variability is likely to be important to control in the formulations.

In addition to drug substance PSD variations, it is believed that ticagrelor surface properties of different batches may also contribute to the tablet attributes, especially dissolution rate. TOF-SIMS analysis of a various batches of drug revealed a slightly different surface composition for one batch from DSM in comparison to AZ Ops and Omnichem materials.

In summary, it is important to control the physical properties of the drug in order to obtain a robust large-scale manufacturing process. Variations in particle habit and potentially particle surface properties were judged to be particularly capable of affecting the properties of the final product.

Example 14—Assessment of Tablet Stability

The effects of storage on the tablets of Example 7 were studied following both open storage under various conditions, as well as storage in aluminium/aluminium blister packs with aluminium laminate form foil and aluminium lid foil (Al/Al blister). The tablets were manufactured using a process in line with that in Example 8 above.

Investigational Stress Stability Study

The performance of ticagrelor orodispersible tablets under stressed open conditions has been demonstrated during development. The study exposed ticagrelor orodispersible tablets in an open dish to different temperature and humidity conditions. By storing the tablets in an open dish they were subject to additional humidity stress than would be encountered when packaged in Al/Al blister.

Stability Protocol

Storage Conditions and Sampling Protocols

The primary stability batches and the supportive batch have been stored in accordance with ICH guideline Q1A. Details of the sampling time points for each condition are presented in Table 31.

TABLE 31

Sampling and storage protocol for primary stability studies

| Storage condition | Time (months) | | | | |
|---|---|---|---|---|---|
| (° C./% RH)/container | 0.5 | 3 | 6 | 9 | 12 |
| 5 - control | − | (+) | (+) | (+) | (+) |
| 25/60 - blister | − | + | + | + | + |
| 25/60 - bulk | − | + | + | + | + |
| 40/75 - blister | − | + | + | − | − |
| 40/75 - bulk | − | + | + | − | − |
| 50/AH - blister | − | + | − | − | − |
| Photo stability[a] | + | − | − | − | − |

RH Relative Humidity.
AH Ambient Humidity.
+ Sample tested to appropriate schedule.
− No sampling.
Blister Al/Al blisters.
Bulk Al bags
5° C. Control sample to be used as a reference sample when performing the description test.
( ) Optional testing if changes seen at other conditions.
[a] 1.2 million lux-hours of visible light and 200 watt-hour/m² UV light; stressed condition. Tested on tablets stored in open dish covered with aluminium foil.

Temperature is controlled to ±2° C. and humidity is controlled to ±5% RH. The investigational stability batch have been stored in open dish for up to 1 month in the following climates 25° C./60% RH, 30° C./65% RH, 40° C./75% RH and 50° C./amb.

Photo Stability

Photo stability has been performed on one batch from the primary stability study in accordance with ICHQ1B.

Stability Tests and Acceptance Limits

The stability of ticagrelor orodispersible tablets 90 mg has been assessed by monitoring appropriate chemical and physical characteristics during the stability study. Testing performed included: assay by HPLC, degradation products by HPLC, disintegration, dissolution (0.2% Tween 80), microbial limits and tablet hardness. Microbial limits testing was applied at 6 month for 40° C./75% RH and at 12, 24 and 36 month time point for 25° C./60% RH in the ICH primary stability studies of the Al/Al blister.

Results

The ICH primary stability data and the supportive stability data obtained for tablets of Example 7 in Aluminium/Aluminium (Al/Al) blister packs are presented in Tables 32 to 39.

The ICH pivotal photo stability data obtained for tablets of Example 7 stored in open dish directly exposed to light are presented in Table 40.

The stability of tablets of Example 7 was tested at stressed conditions, 50° C./ambient humidity (amb) for up to 3 months in Al/Al blister. The results of this study are presented in Tables 41 to 44.

The stability of tablets of Example 7 was tested at stressed conditions, open storage (investigational study) for up to 1 month in different climates. The results can be found in Tables 45 to 48. The stability of tablets of Example 7 stored in a 4 layered aluminium bag (Al bag, bulk pack) was tested under various conditions for up to 6 months. The results can be found in Tables 49 to 54.

TABLE 32

Stability data for 25° C./60% RH of tablets, Batch 51, stored in Al/Al blisters

| | Stability pull times (months) | | | | |
|---|---|---|---|---|---|
| Test | Initial | 3 | 6 | 9 | 12 |
| Description | White, circular, convex tablet | NCH | NCH | NCH | NCH |
| Assay (% label claim) | 100 | 100 | 100 | 100 | 98 |
| Degradation products (% (w/w)): | | | | | |
| Unspecified | <0.05 | <0.05 | <0.05 | <0.05 | <0.05 |
| Total | <0.05 | <0.05 | <0.05 | <0.05 | <0.05 |
| Disintegration (seconds) | 15-28 | 21-27 | 21-31 | 19-33 | 19-29 |
| Dissolution (% label claim) | | | | | |
| Mean (45 min) | 85 | 85 | 92 | 86 | 85 |
| Range (45 min) | 83-88 | 84-87 | 91-93 | 84-87 | 84-86 |
| Mean (60 min) | 88 | 90 | 95 | 89 | 88 |
| Range (60 min) | 86-91 | 89-91 | 93-96 | 88-91 | 87-90 |
| Water content (% (w/w)) | 0.88 | 0.87 | 0.87 | 0.87 | 0.90 |
| Hardness (N) Mean | 62 | 65 | 57 | 65 | 56 |
| Range | 48-79 | 53-82 | 48-64 | 50-88 | 45-76 |
| Microbial quality[a] | Complies | NT | NT | NT | Complies |

[a] Total aerobic microbial count (<10³ cfu/g), total combined yeast and mould count (<10² cfu/g) and *Escherichia coli* (shall be absent)
NCH No change
NT Not tested

TABLE 33

Stability data for 40° C./75% RH of tablets, Batch 51, stored in Al/Al blisters

| | Time (months) | | |
|---|---|---|---|
| Test | Initial | 3 | 6 |
| Description | White, circular, biconvex tablet | NCH | NCH |
| Assay (% label claim) | 100 | 98 | 99 |
| Degradation products (% (w/w)): | | | |
| Unspecified | <0.05 | <0.05 | <0.05 |
| Total | <0.05 | <0.05 | <0.05 |
| Disintegration (seconds) | 15-28 | 17-35 | 17-23 |
| Dissolution (% label claim) | | | |
| Mean (45 min) | 85 | 78 | 88 |
| Range (45 min) | 83-88 | 77-79 | 85-92 |
| Mean (60 min) | 88 | 83 | 92 |
| Range (60 min) | 86-91 | 82-83 | 89-95 |
| Water content (% (w/w)) | 0.88 | 0.86 | 0.89 |
| Hardness (N) Mean | 62 | 58 | 60 |
| Range | 48-79 | 40-81 | 46-76 |
| Microbial quality[a] | Complies | NT | Complies |

[a] Total aerobic microbial count (<10³ cfu/g), total combined yeast and mould count (<10² cfu/g) and *Escherichia coli* (shall be absent)
NCH No change
NT Not tested

TABLE 34

Stability data for 25° C./60% RH of tablets, Batch 52, stored in Al/Al blisters

| Test | Initial | 3 | 6 | 9 | 12 |
|---|---|---|---|---|---|
| Description | White, circular, biconvex tablet | NCH | NCH | NCH | NCH |
| Assay (% label claim) | 99 | 101 | 101 | 101 | 98 |
| Degradation products (% (w/w)): | | | | | |
| Unspecified | <0.05 | <0.05 | <0.05 | <0.05 | <0.05 |
| Total | <0.05 | <0.05 | <0.05 | <0.05 | <0.05 |
| Disintegration (seconds) | 15-25 | 16-44 | 19-31 | 19-39 | 23-24 |
| Dissolution (% label claim) | | | | | |
| Mean (45 min) | 83 | 79 | 86 | 80 | 77 |
| Range (45 min) | 79-85 | 77-81 | 85-89 | 79-80 | 76-79 |
| Mean (60 min) | 87 | 84 | 91 | 84 | 82 |
| Range (60 min) | 83-89 | 82-85 | 89-93 | 84-85 | 80-83 |
| Water content (% (w/w)) | 0.82 | 0.80 | 0.80 | 0.82 | 0.83 |
| Hardness (N) Mean | 72 | 81 | 76 | 67 | 64 |
| Range | 55-90 | 66-91 | 62-86 | 46-83 | 54-81 |
| Microbial quality [a] | Complies | NT | NT | NT | Complies |

[a] Total aerobic microbial count (<10$^3$ cfu/g), total combined yeast and mould count (<10$^2$ cfu/g) and *Escherichia coli* (shall be absent)
NCH No change
NT Not tested

TABLE 35

Stability data for 40° C./75% RH of tablets, Batch 52, stored in Al/Al blisters

| Test | Initial | 3 | 6 |
|---|---|---|---|
| Description | White, circular, biconvex tablet | NCH | NCH |
| Assay (% label claim) | 99 | 101 | 102 |
| Degradation products (% (w/w)): | | | |
| Unspecified | <0.05 | <0.05 | <0.05 |
| Total | <0.05 | <0.05 | <0.05 |
| Disintegration (seconds) | 15-25 | 17-22 | 13-50 |
| Dissolution (% label claim) | | | |
| Mean (45 min) | 83 | 82 | 80 |
| Range (45 min) | 79-85 | 81-83 | 78-82 |
| Mean (60 min) | 87 | 88 | 84 |
| Range (60 min) | 83-89 | 87-89 | 83-85 |
| Water content (% (w/w)) | 0.82 | 0.76 | 0.79 |
| Hardness (N) Mean | 72 | 73 | 66 |
| Range | 55-90 | 63-84 | 58-80 |
| Microbial quality [a] | Complies | NT | Complies |

[a] Total aerobic microbial count (<10$^3$ cfu/g), total combined yeast and mould count (<10$^2$ cfu/g) and *Escherichia coli* (shall be absent)
NCH No change
NT Not tested

TABLE 36

Stability data for 25° C./60% RH of tablets, Batch 53, stored in Al/Al blisters

| Test | Initial | 3 | 6 | 9 | 12 |
|---|---|---|---|---|---|
| Description | White, circular, biconvex tablet | NCH | NCH | NCH | NCH |
| Assay (% label claim) | 98 | 100 | 98 | 100 | 99 |
| Degradation products (% (w/w)): | | | | | |
| Unspecified | 0.06[b] | 0.05[b] | 0.06[b] | 0.06[b] | 0.06[b] |
| Total | 0.06 | 0.05 | 0.06 | 0.06 | 0.06 |
| Disintegration (seconds) | 15-31 | 25-40 | 14-32 | 23-31 | 22-25 |
| Dissolution (% label claim) | | | | | |
| Mean (45 min) | 87 | 86 | 94 | 87 | 86 |
| Range (45 min) | 87-89 | 84-87 | 91-96 | 86-88 | 83-87 |
| Mean (60 min) | 91 | 90 | 97 | 91 | 90 |
| Range (60 min) | 90-92 | 89-91 | 94-100 | 90-91 | 88-92 |
| Water content (% (w/w)) | 0.83 | 0.84 | 0.84 | 0.85 | 0.84 |
| Hardness (N) Mean | 75 | 73 | 69 | 64 | 64 |
| Range | 60-92 | 60-84 | 60-83 | 50-77 | 45-81 |
| Microbial quality [a] | Complies | NT | NT | NT | Complies |

[a] Total aerobic microbial count (<10$^3$ cfu/g), total combined yeast and mould count (<10$^2$ cfu/g) and *Escherichia coli* (shall be absent)
[b] Impurity RRT 1.84
NCH No change
NT Not tested

TABLE 37

Stability data for 40° C./75% RH of tablets, Batch 53, stored in Al/Al blisters

| Test | Initial | 3 | 6 |
|---|---|---|---|
| Description | White, circular, biconvex tablet | NCH | NCH |
| Assay (% label claim) | 98 | 100 | 99 |
| Degradation products (% (w/w)): | | | |
| Unspecified | 0.06[b] | 0.06[b] | 0.07[b] |
| Total | 0.06 | 0.06 | 0.07 |
| Disintegration (seconds) | 15-31 | 17-25 | 15-37 |
| Dissolution (% label claim) | | | |
| Mean (45 min) | 87 | 91 | 87 |
| Range (45 min) | 87-89 | 88-94 | 85-90 |
| Mean (60 min) | 91 | 94 | 92 |
| Range (60 min) | 90-92 | 92-96 | 89-94 |
| Water content (% (w/w)) | 0.83 | 0.81 | 0.84 |
| Hardness (N) Mean | 75 | 69 | 66 |

TABLE 37-continued

Stability data for 40° C./75% RH of tablets, Batch 53, stored in Al/Al blisters

| Test | Time (months) | | |
|---|---|---|---|
| | Initial | 3 | 6 |
| Range | 60-92 | 55-89 | 52-78 |
| Microbial quality [a] | Complies | NT | Complies |

[a] Total aerobic microbial count (<$10^3$ cfu/g), total combined yeast and mould count (<$10^2$ cfu/g) and *Escherichia coli* (shall be absent)
[b] Impurity RRT 1.84
NCH No change
NT Not tested

TABLE 38

Stability data for 25° C./60% RH of tablets, Batch 54, stored in Al/Al blisters

| Test | Time (months) | | |
|---|---|---|---|
| | Initial | 3 | 6 |
| Description | White, circular, flat bevelled tablet | NCH | NCH |
| Assay (% label claim) | 98 | 99 | 98 |
| Degradation products (% (w/w)): | | | |
| Unspecified | <0.05 | <0.05 | <0.05 |
| Total | <0.05 | <0.05 | <0.05 |
| Disintegration (seconds) | 26-52 | 35-45 | 29-41 |
| Dissolution (% label claim) | | | |
| Mean (45 min) | 93 | 86 | 86 |
| Range (45 min) | 91-94 | 84-88 | 85-88 |
| Mean (60 min) | 95 | 86 | 89 |
| Range (60 min) | 94-95 | 85-88 | 86-90 |
| Water content (% (w/w)) | 0.82 | 0.80 | 0.80 |
| Hardness (N) Mean | 55 | NT | 66 |
| Range | 45-66 | NT | 58-71 |
| Microbial quality [a] | Complies | NT | NT |

[a] Total aerobic microbial count (<$10^3$ cfu/g), total combined yeast and mould count (<$10^2$ cfu/g) and *Escherichia coli* (shall be absent)
NCH No change
NT Not tested

TABLE 39

Stability data for 40° C./75% RH of tablets, Batch 54, stored in Al/Al blisters

| Test | Time (months) | | |
|---|---|---|---|
| | Initial | 3 | 6 |
| Description | White, circular, flat bevelled tablet | NCH | NCH |
| Assay (% label claim) | 98 | 98 | 98 |
| Degradation products (% (w/w)): | | | |
| Unspecified | <0.05 | <0.05 | <0.05 |
| Total | <0.05 | <0.05 | <0.05 |
| Disintegration (seconds) | 26-52 | 17-43 | 29-35 |
| Dissolution (% label claim) | | | |
| Mean (45 min) | 93 | 77 | 78 |
| Range (45 min) | 91-94 | 75-79 | 77-80 |
| Mean (60 min) | 95 | 80[b] | 80[b] |
| Range (60 min) | 94-95 | 76-85[b] | 79-82[b] |
| Water content (% (w/w)) | 0.82 | 0.79 | 0.80 |
| Hardness (N) Mean | 55 | NT | 63 |
| Range | 45-66 | NT | 55-71 |
| Microbial quality [a] | Complies | NT | Complies |

[a] Total aerobic microbial count (<$10^3$ cfu/g), total combined yeast and mould count (<$10^2$ cfu/g) and *Escherichia coli* (shall be absent)
[b] Stage 2 requirements have been met (12 units tested),
NCH No change
NT Not tested

TABLE 40

Stability data for photo stability of tablets, Batch 51

| Test | Time (months) | | |
|---|---|---|---|
| | Initial | 0.5 (sample) | 0.5 (reference) |
| Description | White, circular, biconvex tablet | NCH | NT |
| Assay (% label claim) | 100 | 98 | NT |
| Degradation products (% (w/w)): | | | |
| Unspecified | <0.05 | 0.15[b] | <0.05 |
| Total | <0.05 | 0.15 | <0.05 |
| Disintegration (seconds) | 15-28 | 16-34 | NT |
| Dissolution (% label claim) | | | |
| Mean (45 min) | 85 | 84 | NT |
| Range (45 min) | 83-88 | 82-86 | NT |
| Mean (60 min) | 88 | 86 | NT |
| Range (60 min) | 86-91 | 84-88 | NT |
| Water content (% (w/w)) | 0.88 | 1.6 | NT |
| Hardness (N) Mean | 62 | 54 | NT |
| Range | 48-79 | 46-78 | NT |
| Microbial quality [a] | Complies | NT | NT |

[a] Total aerobic microbial count (<$10^3$ cfu/g), total combined yeast and mould count (<$10^2$ cfu/g) and *Escherichia coli* (shall be absent)
[b] Impurity at RRT 0.88
NCH No change
NT Not tested

TABLE 41

Stability data for stressed condition, 50° C./amb for tablets, Batch 51 stored in Al/Al blister

| Test | Initial | 3 months |
|---|---|---|
| Description | White, circular, biconvex tablet | White, circular, biconvex tablet |
| Assay (% label claim) | 100 | 99 |
| Degradation products (% (w/w)): | | |
| Unspecified | <0.05 | <0.05 |
| Total | <0.05 | <0.05 |
| Disintegration (seconds) | 15-28 | 17-25 |
| Dissolution (% label claim) | | |
| Mean (45 min) | 85 | 80[b] |
| Range (45 min) | 83-88 | 73-88[b] |
| Mean (60 min) | 88 | 85[b] |
| Range (60 min) | 86-91 | 78-93[b] |
| Water content (% (w/w)) | 0.88 | 0.87 |
| Hardness (N) Mean | 62 | 52 |
| Range | 48-79 | 46-61 |
| Microbial quality [a] | Complies | Complies |

[a] Total aerobic microbial count (<10$^3$ cfu/g), total combined yeast and mould count (<10$^2$ cfu/g) and *Escherichia coli* (shall be absent)
[b] Stage 2 requirements have been met (12 units tested)

TABLE 42

Stability data for stressed condition, 50° C./amb for tablets, Batch 52 stored in Al/Al blister

| Test | Initial | 3 months |
|---|---|---|
| Description | White, circular, biconvex tablet | White, circular, biconvex tablet |
| Assay (% label claim) | 99 | 101 |
| Degradation products (% (w/w)): | | |
| Unspecified | <0.05 | <0.05 |
| Total | <0.05 | <0.05 |
| Disintegration (seconds) | 15-25 | 13-30 |
| Dissolution (% label claim) | | |
| Mean (45 min) | 83 | 74[b] |
| Range (45 min) | 79-85 | 68-81[b] |
| Mean (60 min) | 87 | 80[b] |
| Range (60 min) | 83-89 | 74-87[b] |
| Water content (% (w/w)) | 0.82 | 0.77 |
| Hardness (N) Mean | 72 | 64 |
| Range | 55-90 | 56-80 |
| Microbial quality [a] | Complies | Complies |

[a] Total aerobic microbial count (<10$^3$ cfu/g), total combined yeast and mould count (<10$^2$ cfu/g) and *Escherichia coli* (shall be absent)
[b] Stage 2 requirements have been met (12 units tested)

TABLE 43

Stability data for stressed condition, 50° C./amb for tablets, Batch 53 stored in Al/Al blister

| Test | Initial | 3 months |
|---|---|---|
| Description | White, circular, biconvex tablet | White, circular, biconvex tablet |
| Assay (% label claim) | 98.4 | 99.3 |
| Degradation products (% (w/w)): | | |
| Unspecified | 0.06[b] | 0.06[b] |
| Total | 0.06 | 0.06 |
| Disintegration (seconds) | 15-31 | 14-26 |
| Dissolution (% label claim) | | |
| Mean (45 min) | 87 | 87 |
| Range (45 min) | 87-89 | 84-89 |
| Mean (60 min) | 91 | 91 |
| Range (60 min) | 90-92 | 88-95 |
| Water content (% (w/w)) | 0.83 | 0.82 |
| Hardness (N) Mean | 75 | 58 |
| Range | 60-92 | 48-74 |
| Microbial quality [a] | Complies | Complies |

[a] Total aerobic microbial count (<10$^3$ cfu/g), total combined yeast and mould count (<10$^2$ cfu/g) and *Escherichia coli* (shall be absent)
[b] Impurity RRT 1.84

TABLE 44

Stability data for stressed condition, 50° C./amb, for tablets, Batch 54 stored in Al/Al blister

| Test | Initial | 3 months |
|---|---|---|
| Description | White, circular, flat bevelled tablet | NCH |
| Assay (% label claim) | 98 | 99 |
| Degradation products (% (w/w)): | | |
| Unspecified | <0.05 | <0.05 |
| Total | <0.05 | <0.05 |
| Disintegration (seconds) | 26-52 | 15-22 |
| Dissolution (% label claim) | | |
| Mean (45 min) | 93 | 74[b] |
| Range (45 min) | 91-94 | 73-76[b] |
| Mean (60 min) | 95 | 78[b] |
| Range (60 min) | 94-95 | 76-79[b] |
| Water content (% (w/w)) | 0.82 | 0.78 |
| Hardness (N) Mean | 55 | 57 |
| Range | 45-66 | 52-63 |
| Microbial quality [a] | Complies | Complies |

[a] Total aerobic microbial count (<10$^3$ cfu/g), total combined yeast and mould count (<10$^2$ cfu/g) and *Escherichia coli* (shall be absent)
[b] Stage 2 requirements have been met (12 units tested)
NCH No change

TABLE 45

Stability data for stressed condition, 25° C./60% RH for tablets, Batch 45 stored open

| Test | Initial | 1 week | 2 weeks | 1 month |
|---|---|---|---|---|
| Description | White, circular, flat bevelled tablet | NCH | NCH | NCH |
| Assay (% label claim) | 101 | NT | NT | 97 |
| Degradation products (% (w/w)): | | | | |
| Unspecified | <0.05 | NT | NT | <0.05 |
| Total | <0.05 | NT | NT | <0.05 |
| Disintegration (seconds) | ≤60 | ≤60 | ≤60 | ≤60 |
| Dissolution (% label claim) | | | | |
| Mean | 83 | 78 | 79 | 77[a] |
| Range | 81-87 | 75-82 | 78-82 | 73-80[a] |
| Water content (% (w/w)) | 0.9 | 2.7 | 2.3 | 2.2 |
| Tablet Hardness (N) | 56 | 23 | 26 | 28 |

[a] Stage 2 requirements have been met (12 units tested)
NCH No change
NT Not tested

TABLE 46

Stability data for stressed condition, 30° C./65% RH for tablets, Batch 45 stored open

| Test | Initial | 1 week | 2 weeks | 1 month |
|---|---|---|---|---|
| Description | White, circular, flat bevelled tablet | NCH | NCH | NCH |
| Assay (% label claim) | 101 | NT | NT | 100 |
| Degradation products (% (w/w)): | | | | |
| Unspecified | <0.05 | NT | NT | <0.05 |
| Total | <0.05 | NT | NT | <0.05 |
| Disintegration (seconds) | ≤60 | ≤60 | ≤60 | ≤60 |
| Dissolution (% label claim) | | | | |
| Mean | 83 | 76[a] | 75[a] | 74[a] |
| Range | 81-87 | 73-78[a] | 72-77[a] | 71-76[a] |
| Water content (% (w/w)) | 0.9 | 2.9 | 2.4 | 2.2 |
| Tablet Hardness (N) | 56 | 18 | 19 | 20 |

[a] Stage 2 requirements have been met (12 units tested)
NCH No change
NT Not tested

TABLE 47

Stability data for stressed condition, 40° C./75% RH for tablets, Batch 45 stored open

| Test | Initial | 1 week | 2 weeks | 1 month |
|---|---|---|---|---|
| Description | White, circular, flat bevelled tablet | NCH | NCH | NCH |
| Assay (% label claim) | 101 | NT | NT | 99 |
| Degradation products (% (w/w)): | | | | |
| Unspecified | <0.05 | NT | NT | <0.05 |
| Total | <0.05 | NT | NT | 0.10 |
| Disintegration (seconds) | ≤60 | ≤60 | ≤60 | ≤60 |
| Dissolution (% label claim) | | | | |
| Mean | 83 | 73[a] | 74[a] | 72[a] |
| Range | 81-87 | 70-74[a] | 71-76[a] | 69-75[a] |
| Water content (% (w/w)) | 0.9 | 3.4 | 2.7 | 2.4 |
| Tablet Hardness (N) | 56 | 15 | 16 | 15 |

[a] Stage 2 requirements have been met (12 units tested)
NCH No change
NT Not tested

TABLE 48

Stability data for stressed condition, 50° C./amb for tablets, Batch 45 stored open

| Test | Initial | 1 week | 2 weeks | 1 month |
|---|---|---|---|---|
| Description | White, circular, flat bevelled tablet | NCH | NCH | NCH |
| Assay (% label claim) | 101 | NT | NT | 99 |
| Degradation products (% (w/w)): | | | | |
| Unspecified | <0.05 | NT | NT | <0.05 |
| Total | <0.05 | NT | NT | <0.05 |
| Disintegration (seconds) | ≤60 | ≤60 | ≤60 | ≤60 |
| Dissolution (% label claim) | | | | |
| Mean | 83 | 78 | 77 | 77 |
| Range | 81-87 | 78-79 | 75-80 | 75-78 |
| Water content (% (w/w)) | 0.9 | 0.3 | 0.6 | 0.7 |
| Tablet Hardness (N) | 56 | 56 | 53 | 53 |

NCH No change
NT Not tested

TABLE 49

Stability data for 25° C./60% RH of ticagrelor orodispersible tablets, 90 mg, Batch 51, stored in Al bags

| | | Time (months) | | | |
|---|---|---|---|---|---|
| Test | Initial | 3 | 6 | 9 | 12 |
| Description | White, round, convex tablet | NCH | NCH | NCH | NCH |
| Assay (%) | 100 | 99 | 100 | 98 | 99 |
| Degradation products (% (w/w)): | | | | | |
| Unspecified | <0.05 | <0.05 | <0.05 | <0.05 | <0.05 |
| Total | <0.05 | <0.05 | <0.05 | <0.05 | <0.05 |
| Disintegration (seconds) | 28 | 48 | 31 | 37 | 23 |
| Dissolution (% label claim) | | | | | |
| Mean | 88 | 89 | 97 | 89 | 89 |
| Range | 86-91 | 85-92 | 95-101 | 87-91 | 85-91 |

TABLE 49-continued

Stability data for 25° C./60% RH of ticagrelor orodispersible tablets, 90 mg, Batch 51, stored in Al bags

| Test | Initial | Time (months) 3 | 6 | 9 | 12 |
|---|---|---|---|---|---|
| Water content (% (w/w)) | 0.88 | 0.90 | 0.90 | 0.92 | 0.95 |
| Microbial quality [a] | Complies | NT | NT | NT | NT |

[a] Total aerobic microbial count (<$10^3$ cfu/g), total combined yeast and mould count (<$10^2$ cfu/g) and *Escherichia coli* (shall be absent)
NCH No change
NT Not tested

TABLE 50

Stability data for 40° C./75% RH of ticagrelor orodispersible tablets, 90 mg, Batch 51, stored in Al bags

| Test | Initial | Time (months) 3 | 6 |
|---|---|---|---|
| Description | White, round, convex tablet | NCH | NCH |
| Assay (%) | 100 | 99 | 100 |
| Degradation products (% (w/w)): | | | |
| Unspecified | <0.05 | <0.05 | <0.05 |
| Total | <0.05 | <0.05 | <0.05 |
| Disintegration (seconds) | 28 | 29 | 25 |
| Dissolution (% label claim) | | | |
| Mean | 88 | 83 | 92 |
| Range | 86-91 | 81-85 | 90-95 |
| Water content (% (w/w)) | 0.88 | 0.86 | 0.89 |
| Microbial quality [a] | Complies | NT | Complies |

[a] Total aerobic microbial count (<$10^3$ cfu/g), total combined yeast and mould count (<$10^2$ cfu/g) and *Escherichia coli* (shall be absent)
NCH No change
NT Not tested

TABLE 51

Stability data for 25° C./60% RH of ticagrelor orodispersible tablets, 90 mg, Batch 52, stored in Al bags

| Test | Initial | Time (months) 3 | 6 | 9 | 12 |
|---|---|---|---|---|---|
| Description | White, round, convex tablet | NCH | NCH | NCH | NCH |
| Assay (%) | 99 | 99 | 99 | 100 | 99 |
| Degradation products (% (w/w)): | | | | | |
| Unspecified | <0.05 | <0.05 | <0.05 | <0.05 | <0.05 |
| Total | <0.05 | <0.05 | <0.05 | <0.05 | <0.05 |
| Disintegration (seconds) | 25 | 35 | 54 | 31 | 26 |
| Dissolution (% label claim) | | | | | |
| Mean | 87 | 82 | 91 | 83 | 83 |
| Range | 83-89 | 80-84 | 88-93 | 80-85 | 81-85 |

TABLE 51-continued

Stability data for 25° C./60% RH of ticagrelor orodispersible tablets, 90 mg, Batch 52, stored in Al bags

| Test | Initial | Time (months) 3 | 6 | 9 | 12 |
|---|---|---|---|---|---|
| Water content (% (w/w)) | 0.82 | 0.82 | 0.85 | 0.87 | 0.88 |
| Microbial quality [a] | Complies | NT | NT | NT | NT |

[a] Total aerobic microbial count (<$10^3$ cfu/g), total combined yeast and mould count (<$10^2$ cfu/g) and *Escherichia coli* (shall be absent)
NCH No change
NT Not tested

TABLE 52

Stability data for 40° C./75% RH of ticagrelor orodispersible tablets, 90 mg, Batch 52, stored in Al bags

| Test | Initial | Time (months) 3 | 6 |
|---|---|---|---|
| Description | White, round, convex tablet | NCH | NCH |
| Assay (%) | 99 | 99 | 100 |
| Degradation products (% (w/w)): | | | |
| Unspecified | <0.05 | <0.05 | <0.05 |
| Total | <0.05 | <0.05 | <0.05 |
| Disintegration (seconds) | 25 | 29 | 40 |
| Dissolution (% label claim) | | | |
| Mean | 87 | 85 | 84 |
| Range | 83-89 | 82-87 | 82-91 |
| Water content (% (w/w)) | 0.82 | 0.81 | 0.86 |
| Microbial quality [a] | Complies | NT | Complies |

[a] Total aerobic microbial count (<$10^3$ cfu/g), total combined yeast and mould count (<$10^2$ cfu/g) and *Escherichia coli* (shall be absent)
NCH No change
NT Not tested

TABLE 53

Stability data for 25° C./60% RH of ticagrelor orodispersible tablets, 90 mg, Batch 53, stored in Al bags

| Test | Initial | Time (months) 3 | 6 | 9 | 12 |
|---|---|---|---|---|---|
| Description | White, round, convex tablet | NCH | NCH | NCH | NCH |
| Assay (%) | 98 | 101 | 100 | 100 | 99 |
| Degradation products (% (w/w)): | | | | | |
| Unspecified | $0.06^1$ | $0.05^1$ | $0.06^1$ | $0.06^1$ | $0.06^1$ |
| Total | 0.06 | 0.05 | 0.06 | 0.06 | 0.06 |
| Disintegration (seconds) | 31 | 38 | 31 | 31 | 29 |
| Dissolution (% label claim) | | | | | |
| Mean | 91 | 89 | 97 | 91 | 90 |
| Range | 90-92 | 87-91 | 93-100 | 89-92 | 90-92 |

TABLE 53-continued

Stability data for 25° C./60% RH of ticagrelor orodispersible tablets, 90 mg, Batch 53, stored in Al bags

|  | | Time (months) | | | |
|---|---|---|---|---|---|
| Test | Initial | 3 | 6 | 9 | 12 |
| Water content (% (w/w)) | 0.83 | 0.88 | 0.89 | 0.88 | 0.94 |
| Microbial quality [a] | Complies | NT | NT | NT | NT |

[1]Impurity RRT 1.84
[a] Total aerobic microbial count (<$10^3$ cfu/g), total combined yeast and mould count (<$10^2$ cfu/g) and *Escherichia coli* (shall be absent)
NCH No change
NT Not tested

TABLE 54

Stability data for 40° C./75% RH of ticagrelor orodispersible tablets, 90 mg, Batch 53, stored in Al bags

|  | | Time (months) | |
|---|---|---|---|
| Test | Initial | 3 | 6 |
| Description | White, round, convex tablet | NCH | NCH |
| Assay (%) | 98 | 98 | 99 |
| Degradation products (% (w/w)): | | | |
| Unspecified | 0.06[1] | 0.06[1] | 0.07[1] |
| Total | 0.06 | 0.06 | 0.07 |
| Disintegration (seconds) | 31 | 37 | 23 |
| Dissolution (% label claim) | | | |
| Mean | 91 | 98 | 92 |
| Range | 90-92 | 94-102 | 90-93 |
| Water content (% (w/w)) | 0.83 | 0.85 | 0.87 |
| Microbial quality [a] | Complies | NT | Complies |

[1]Impurity RRT 1.84
[a] Total aerobic microbial count (<$10^3$ cfu/g), total combined yeast and mould count (<$10^2$ cfu/g) and *Escherichia coli* (shall be absent)
NCH No change
NT Not tested Summary of Results and Discussion ICH Primary Stability Studies Stability data for the tablets stored in Al/Al blisters show no significant change in description, assay, degradation products, disintegration or dissolution after 12 months storage at 25° C./60% RH. Storage at the accelerated condition of 40° C./75% RH after 6 months show no significant change in description, assay, degradation products, disintegration or dissolution. Dissolution shows a variation in data over time but no trend can be seen and all results fulfil the specification requirement.

The water content and microbial quality shows no significant changes after 12 months storage at 25° C./60% RH. Storage at the accelerated condition of 40° C./75% RH after 6 months shows no significant changes.

Tablet hardness generally decreases as a result of moisture uptake, which weakens the tablets. Therefore, inhibition of moisture uptake is beneficial for tablet stability. However, the subjective toughness of the tablets is still good even if the hardness has been reduced through moisture uptake.

Photo Stability and Stressed Condition

Stability data for tablets stored in an open dish under photo stability conditions show that light has no significant effect on the stability of the tablets. Formation of one degradation product was seen at very low levels for the tablets that were directly exposed to light. The drug product is fully protected in the Al/Al blister pack since this is impenetrable to light. The stressed condition of 50° C./ambient shows no significant changes in description, assay, degradation products, disintegration, dissolution, water or microbial quality after 3 months storage in Al/Al blisters.

Investigational Stressed Stability Study

The stability data generated during the investigational study demonstrate that storage up to 1 month open, does not appear to have an adverse effect on description, assay, degradation products, disintegration or dissolution. An increase in water content was observed for the tablets stored at humid conditions. This increase in water amount appears to impact on the tablet hardness as it makes the tablets softer. This is an inherent property for orodispersible tablets as they are designed to take up water to readily disintegrate.

Example 15—Relative Bioavailability Study (Study A)

A relative bioavailability study (hereafter referred to as clinical study A) compared the orodispersible tablet of Example 7, administered with water (after oral dispersion) and without water, to a film-coated tablet containing 90 mg of ticagrelor. In clinical study A the orodispersible tablet was also suspended in water and administered through a nasogastric tube and compared to the film-coated tablet.

The composition of the orodispersible tablet used in clinical study A was identical to that in Example 7 and was manufactured at a batch size of 256 kg.

The film-coated tablet used in clinical study A was equivalent to the marketed ticagrelor film-coated tablet.

Figure 8:
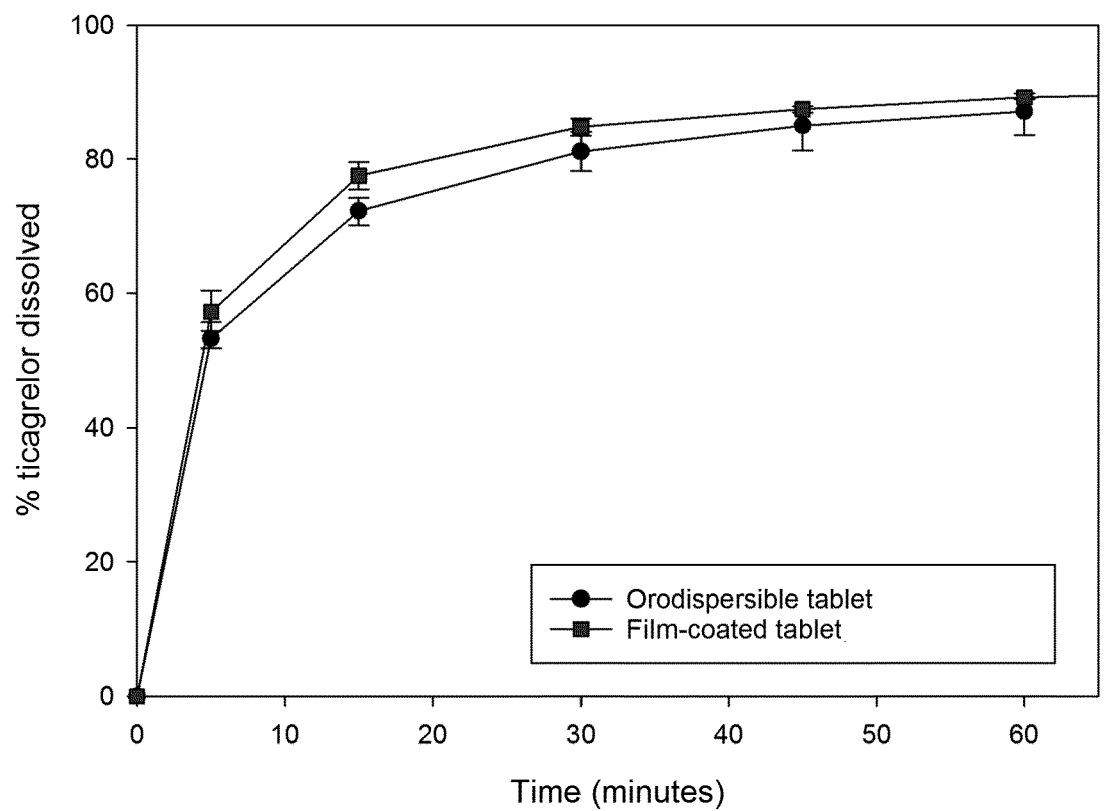
FIG. 8 shows the dissolution of ticagrelor orodispersible and film-coated tablets 90 mg dosed in clinical study A in 0.2% (w/v) Tween 80, mean values (n=6). Error bars represent min and max values.

The dissolution profiles for the orodispersible and film-coated tablets used in clinical study A, obtained using the proposed release method (manual sampling used and % ticagrelor dissolved measured by UV) are presented in FIG. 8. As can be seen, the dissolution profiles of the orodispersible and film-coated tablets are similar, which in vivo results in similar exposure.

Study Design and Methodology:

This study was an open-label, randomised, four-period, four-treatment, crossover study in healthy male and female of non-childbearing potential subjects, performed at a single study centre. The study was comprised of:

A screening period of maximum 21 days;

Four treatment periods during which subjects were resident prior to the evening meal the night before dosing with ticagrelor (Day −1) until at least 48 hours after dosing; discharged on the morning of Day 3; and A final visit within 5 to 10 days after the last administration of ticagrelor.

There was a minimum washout period of 7 days between each dose administration.

Subjects received single doses of ticagrelor in 4 different ways under fasted conditions. Following an overnight fast of at least 10 hours, each subject received a single dose of each treatment on 4 occasions, respectively. The treatment protocol is summarised in Table 55.

TABLE 55

Treatment protocol

| Treatment | Product | Administration | Dose |
|---|---|---|---|
| Treatment A | Test product | Ticagrelor OD tablets administered with 200 mL of water | 1 × 90 mg |
| Treatment B | Test product | Ticagrelor OD tablets administered without water | 1 × 90 mg |
| Treatment C | Test product | Ticagrelor OD tablets suspended in water to be administered through a NG tube into the stomach (total of 200 mL of water) | 1 × 90 mg |
| Treatment D | Reference product | Ticagrelor IR tablets administered with 200 mL of water | 1 × 90 mg |

Test product: Ticagrelor 90 mg OD tablet according to Example 7

Reference product: Ticagrelor 90 mg IR (immediate release) tablet

Study Subjects

36 Healthy male and female (non-childbearing potential) subjects were enrolled in the study and 30 subject completed it. All subjects were healthy male or female subjects aged 18 to 55 years, with a body mass index between 18.5 and 29.9 kg/m² inclusive weighing at least 50 kg and no more than 100 kg inclusive.

Duration of Treatment:

The duration of study participation for each subject was approximately 7 to 8 weeks consisting of a Screening visit (from Day −21 to −1), admission to the clinical unit (on Day −1 of each treatment period), 4 in-house treatment periods (Days 1 to 3) with a 7-day washout period between administrations of investigational medicinal product (IMP) in each treatment period and a Follow-up visit after Treatment Period 4.

Subjects received a single dose of IMP on Day 1 of each of the 4 in-house treatment periods.

Treatment Compliance:

Dosing took place at the PAREXEL Early Phase Clinical Unit. After IMP administration, a check of the subject's mouth and hands was performed. The exact day and time of IMP administration, as well as the volume of water accompanying the administration were recorded.

Criteria for Evaluation:

Pharmacokinetic Parameters:

The PK parameters were assessed for ticagrelor (parent) and its active metabolite AR-C124910XX based on plasma concentrations.

Primary PK Parameters:

| | |
|---|---|
| $C_{max}$ | Maximum observed plasma concentration |
| $AUC_{(0-t)}$ | Area under the plasma concentration-time curve from time zero to time of last quantifiable analyte concentration |
| AUC | Area under plasma concentration-time curve from zero to infinity |

Secondary PK Parameters:

| | |
|---|---|
| $t_{max}$ | Time to reach maximum observed concentration |
| $t_{1/2\lambda z}$ | Half-life associated with terminal slope ($\lambda_z$) of a semi-logarithmic concentration-time curve |
| $MRC_{max}$ | Ratio of metabolite $C_{max}$ to parent $C_{max}$, adjusted for differences in molecular weights |
| $MRAUC_{(0-t)}$ | Ratio of metabolite $AUC_{(0-t)}$ to parent $AUC_{(0-t)}$, adjusted for differences in molecular weights |
| MRAUC | Ratio of metabolite AUC to parent AUC, adjusted for differences in molecular weights |

Diagnostic PK parameters were listed.

Safety Variables:

Safety variables included adverse events (AEs), vital signs (blood pressure and pulse), 12-lead electrocardiograms (ECGs) and laboratory assessments (hematology, clinical chemistry and urinalysis).

In addition to the above, physical examination findings, pregnancy testing (females only) and use of concomitant medication were also reported. Viral serology, thyroid-stimulating hormone (TSH) and follicle-stimulating hormone (FSH) (females only), coagulation and urine drugs of abuse, alcohol and cotinine were assessed for eligibility.

Statistical Methods:

Determination of Sample Size

Based on the bioequivalence range of 0.80-1.25 for ticagrelor and its active metabolite AR-C124910XX and a within-subject coefficient of variation (CV) for $C_{max}$ and AUC of ticagrelor and AR-C124910XX of less than or equal to 24%, 28 evaluable subjects were needed to achieve a power of 90%.

Up to 36 subjects were randomised to a 4 sequence Williams design for 4 periods and 4 treatments: ADBC, BACD, CBDA and DCAB, in order to ensure at least 28 evaluable subjects at the end of the last treatment period.

Pharmacokinetic Analysis:

Pharmacokinetic parameters were summarised for each treatment using descriptive statistics. Where possible, the following descriptive statistics were presented: n, geometric mean, geometric CV, arithmetic mean, arithmetic standard deviation, median, minimum and maximum. For $t_{max}$, only n, median, minimum and maximum were presented.

Bioavailability comparison of treatments A, B and C (test product) and D (reference product) were assessed on the ratio of log-transformed $C_{max}$, $AUC_{0-t}$, and AUC of both ticagrelor and AR-C124910XX using a 2-sided 90% confidence interval (CI) approach based on an analysis of variance (ANOVA) model including fixed effects for treatment, sequence, period and subject within sequence.

All PK parameters were log-transformed prior to analysis. The estimated treatment differences and the 90% CIs on the log scale were back transformed to obtain the geometric mean ratios for each pair of treatments.

For exploratory purposes, the ANOVA as outlined above was repeated with a random effect of subject within sequence.

Safety Analysis:

All AEs were coded using Medical Dictionary for Regulatory Activities (MedDRA), and were listed for each subject. The results of the vital signs measurements, hematology, clinical chemistry and coagulation values were listed by subject and time-point. 12-lead ECG results were listed for each subject and the results of the physical examination were listed by body system for each subject.

Pharmacokinetic Results:

Following 90 mg ticagrelor OD tablets with water, without water, or suspended in water to be administered via NG tube, plasma concentration-time profiles for ticagrelor and metabolite AR-C124910XX were generally similar to those following 90 mg ticagrelor IR tablets. The profiles were characterised as rapid ticagrelor absorption with $C_{max}$ achieved at median $t_{max}$ of approximately 2 hours post-dose and rapid formation of metabolite AR-C124910XX with median $t_{max}$ of 2 to 3 hours post-dose. After reaching $C_{max}$, plasma ticagrelor and metabolite AR-C124910XX concentrations declined with terminal mean $t_{1/2\lambda z}$ of 7.99-8.21 hours and 9.35-9.48 hours, respectively. Plasma metabolite AR-C124910XX $C_{max}$ and AUC was 27.1-30.0% and 38.2-40.5% of plasma ticagrelor $C_{max}$ and AUC, respectively.

The derived mean PK parameters were similar across the 4 treatments for ticagrelor and metabolite AR-C124910XX, suggesting that the rate of absorption ($C_{max}$ and $t_{max}$) and extent of absorption (AUC) amongst the treatments were similar.

The 90% CIs of the geometric mean ratios for ticagrelor AUC (90.27, 99.89) and metabolite AR-C124910XX AUC (91.36, 98.42) were entirely contained within the acceptance interval of 80-125%. The ticagrelor $C_{max}$ from OD tablets with water was about 15% (90% CI: 76.77, 93.78) lower than the IR tablets, while the 90% CI for metabolite AR-C124910XX C (82.03, 98.39) was contained within the 80-125% interval.

The 90% CIs of geometric mean ratios for ticagrelor and AR-C124910XX AUC ([89.81, 100.99] and [91.78, 99.82], respectively) and $C_{max}$ ([88.22, 105.79] and [90.53, 104.90], respectively) after ticagrelor OD tablets without water, and AUC ([90.26, 98.73] and [93.26, 99.87], respectively) and $C_{max}$ ([85.59, 99.25] and [90.83, 103.74], respectively) after ticagrelor OD tablets suspended in water to be administered via NG tube, were entirely contained within the acceptance interval of 80-125%.

The between-subject variability was low to moderate and was similar across treatments for both ticagrelor and metabolite AR-C124910XX; the geometric mean CV % in $C_{max}$ of ticagrelor and metabolite AR-C124910XX was approximately 25-34%, and in AUC of ticagrelor and metabolite AR-C124910XX was approximately 19-44%.

Safety Results

There were no deaths, serious adverse event or AEs leading to permanent discontinuation of IMP during the conduct of this study.

A total of 18 AEs were reported for 9 (25.0%) subjects, all classified as mild in intensity. All AEs resolved by the end of the study.

The most commonly reported AEs were dizziness in the system organ class of Nervous System Disorders and thrombophlebitis in the SOC of Vascular Disorders in 2 (5.6%) subjects, respectively.

No trends were observed in AEs, clinical laboratory values, vital sign measurements, 12 lead ECG readings and physical examination.

This open-label, randomised, four period, four treatment, crossover, single centre, single dose study was designed to assess the bioavailability of ticagrelor OD tablets, compared to ticagrelor IR tablets in healthy subjects.

The extent of absorption (AUC) after ticagrelor OD tablets with water, without water, or suspended in water to be administered via NG tube was equivalent to that after ticagrelor IR tablets, with the 90% CIs of geometric mean ratios for ticagrelor and metabolite AR-C124910XX AUC entirely contained within the acceptance interval of 80-125%. The ticagrelor $C_{max}$ from ticagrelor OD tablets with water was about 15% (90% CI: 76.77, 93.78) lower than ticagrelor IR tablets, while the 90% CI for metabolite AR-C124910XX $C_{max}$ as well as the $C_{max}$ of ticagrelor and metabolite AR-C124910XX from ticagrelor OD tablets without water or suspended in water to be administered via NG tube were entirely contained within the 80-125% interval.

(i) The extent of absorption from ticagrelor 90 mg OD tablets administered with water was equivalent to ticagrelor IR, while its $C_{max}$ was about 15% lower than ticagrelor 90 mg IR tablets.

(ii) Ticagrelor 90 mg OD tablets administered without water were bioequivalent to ticagrelor 90 mg IR tablets.

(iii) Ticagrelor 90 mg OD tablets suspended in water, administered through NG tube into stomach were bioequivalent to ticagrelor 90 mg IR tablets.

This result demonstrated that ticagrelor OD tablets formulation as well as the ways of administering ticagrelor OD tablets did not greatly affect the pharmacokinetic profiles of ticagrelor and metabolite AR-C124910XX, compared to IR tablets. Overall single 90 mg doses of ticagrelor tablets in healthy male and non-childbearing female subjects were considered safe and well tolerated in this study.

Pharmacokinetic parameters and comparisons according to standard bioequivalence criteria are presented in Table 56.

TABLE 56

Comparisons of exposures from clinical study A, orodispersible versus film-coated tablet, according to bioequivalence criteria

| Parameter | Treatment | N | GLS mean | n | Pair | GLS mean ratio (%) | 90% CIs |
|---|---|---|---|---|---|---|---|
| AUC (ng · h/mL) | A | 30 | 3072 | 30 | A/D | 94.96 | 90.27, 99.89 |
| | D | 33 | 3236 | | | | |
| | B | 31 | 3241 | 31 | B/D | 95.24 | 89.81, 100.99 |
| | D | 33 | 3404 | | | | |
| | C | 33 | 3220 | 33 | C/D | 94.40 | 90.26, 97.73 |
| | D | 33 | 3411 | | | | |
| $C_{max}$ (ng/mL) | A | 30 | 428.3 | 30 | A/D | 84.85 | 76.77, 93.78 |
| | D | 33 | 504.8 | | | | |
| | B | 31 | 500.0 | 31 | B/D | 96.61 | 88.22, 105.79 |
| | D | 33 | 517.5 | | | | |
| | C | 33 | 477.9 | 33 | C/D | 92.16 | 85.59, 99.25 |
| | D | 33 | 518.6 | | | | |

ODT—Orodispersible tablet.
Treatment A - ODT with water. ODT placed on the tongue, after disintegration subsequently swallowed with 200 mL water;
Treatment B - ODT without water. ODT placed on the tongue, after disintegration subsequently swallowed with saliva;
Treatment C - ODT suspended in water and given via nasogastric tube (total water volume of 200 mL given);
Treatment D - Film-coated tablet given with 200 mL water.
AUC - Area under the plasma concentration-time curve from zero to infinity;
$C_{max}$- Maximum plasma (peak) drug concentration after single dose administration;
N - all subjects in the pharmacokinetic analysis set;
n - all subjects included in the statistical analysis set;
GLS—Geometric least squares;
CI—Confidence interval.

Example 16—Assessment of Bioequivalence (Study B)

A bioequivalence study (clinical study B) was also performed in Japanese subjects. The study was an open-label, randomised, three-period, three-treatment, crossover study in healthy Japanese subjects (males and females), performed at a single study center.

The study comprised:
(i) A screening period of maximum 28 days;
(ii) Three treatment periods during which subjects will be resident prior to the evening meal the night before dosing with ticagrelor (Day −1) until at least 48 hours after dosing; discharged on the morning of Day 3; and
(iii) A final visit within 5 to 10 days after the last administration of ticagrelor.

There was a minimum washout period of 7 days between each dose administration. Subjects received single doses of ticagrelor in three different ways under fasted conditions. Following an overnight fast of at least 10 hours, each subject received a single dose of each treatment on three occasions, respectively. The treatment protocol is summarised in Table 57.

TABLE 57

Treatment protocol

| Treatment | Product | Administration | Dose |
|---|---|---|---|
| Treatment A | Test product (Ticagrelor 90 mg OD tablets) | Ticagrelor OD tablets administered with 150 mL of water | 1 × 90 mg |
| Treatment B | Test product (Ticagrelor 90 mg OD tablets) | Ticagrelor OD tablets administered without water | 1 × 90 mg |
| Treatment C | Reference product (Ticagrelor 90 mg IR tablets) | Ticagrelor IR tablets administered with 150 mL of water | 1 × 90 mg |

The route of administration was oral. Patients received a single dose of either the test product or the reference product. Each subject was involved in the study for 7 to 8 weeks.

Blood samples for the determination of plasma concentrations of both ticagrelor and its active metabolite AR-C124910XX were collected for each treatment period: 0 hours (pre-dose) and post-dose at 0.5 (30 minutes), 1, 2, 3, 4, 6, 8, 10, 12, 16, 24, 36 and 48 hours (14 samples per treatment period). Plasma samples were analysed for ticagrelor and AR-C124910XX using a validated assay.

In the study, the ticagrelor orodispersible tablet (according to Example 7) was administered with water (after oral dispersion) and without water and compared to ticagrelor film-coated tablet 90 mg. The same batches as included in clinical study A were used for the test product and the reference product. The ticagrelor orodispersible tablet administered with and without water was shown to be bioequivalent to ticagrelor film-coated tablet in Japanese subjects. Pharmacokinetic parameters and comparisons according to standard bioequivalence criteria are presented in Table 58.

TABLE 58

Tablets Compared to Ticagrelor IR Tablets (Pharmacokinetic Analysis Set)

| Pair (Test/ Reference) | Parameter (unit) | n | Geometric LS Mean* | | Pairwise Comparison§ | |
|---|---|---|---|---|---|---|
| | | | Test | Reference | Ratio# | 90% CI# |
| OD with water/ IR | AUC (h · ng/mL) | 41 | 3515 | 3595 | 97.75 | 94.40, 101.21 |
| | AUC$_{(0-t)}$ (h · ng/mL) | 41 | 3457 | 3536 | 97.76 | 94.46, 101.18 |
| | C$_{max}$ (ng/mL) | 41 | 529.8 | 568.7 | 93.16 | 85.80, 101.15 |
| OD without water/ IR | AUC (h · ng/mL) | 41 | 3468 | 3594 | 96.50 | 93.31, 99.80 |
| | AUC$_{(0-t)}$ (h · ng/mL) | 41 | 3406 | 3534 | 96.38 | 93.24, 99.63 |

TABLE 58-continued

Tablets Compared to Ticagrelor IR Tablets (Pharmacokinetic Analysis Set)

| Pair (Test/ Reference) | Parameter (unit) | n | Geometric LS Mean* | | Pairwise Comparison§ | |
|---|---|---|---|---|---|---|
| | | | Test | Reference | Ratio# | 90% CI# |
| | C$_{max}$ (ng/mL) | 41 | 532.7 | 568.7 | 93.67 | 87.88, 99.84 |

ANOVA: analysis of variance;
AUC = area under plasma concentration-time curve from zero extrapolated to infinity;
AUC$_{(0-t)}$: area under the plasma concentration-time curve from time zero to time of last quantifiable analyte concentration;
CI: confidence interval;
C$_{max}$: maximum observed plasma concentration;
IR: immediate-release;
max: maximum;
min: minimum;
n: number of subjects included in the statistical comparison analysis;
OD: orodispersible;
SD: standard deviation.
*Based on pairwise balanced comparisons and were back-transformed.
Geometric mean ratio and CI were back-transformed and presented as percentage.
§Result based on ANOVA of log-transformed pharmacokinetic parameter with treatment, sequence, period and subject within sequence as fixed effects.

Comparative Example 17—Assessment of Push-Through Blister Packs

A study was conducted involving 10 test persons (7 female and 3 male, aged 22 to 58) with push-through blister packs.

Each person was provided with 10 blister cards, each blister card containing 10 tablets (100 tablets per person in total). The tablets were identical with the orodispersible tablets of Example 7.

Each person was then asked to push out all of the tablets in the manner in which they normally would.
Result
The number of broken tablets was as follows:
Mean: 2.5 broken tablets per 100 (i.e. per person)
Range: 0-7 broken tablets per 100 (i.e. per person)

Example 18—Assessment of Tearable Blister Packs

Tests conducted with standard push through aluminium/aluminium blister packs resulted in approx. 2.5% broken tablets (see Comparative Example 17). A further study was conducted involving 10 test persons (4 female and 6 male, aged 25 to 53) with modified push-through blister packs.

Figure 9:
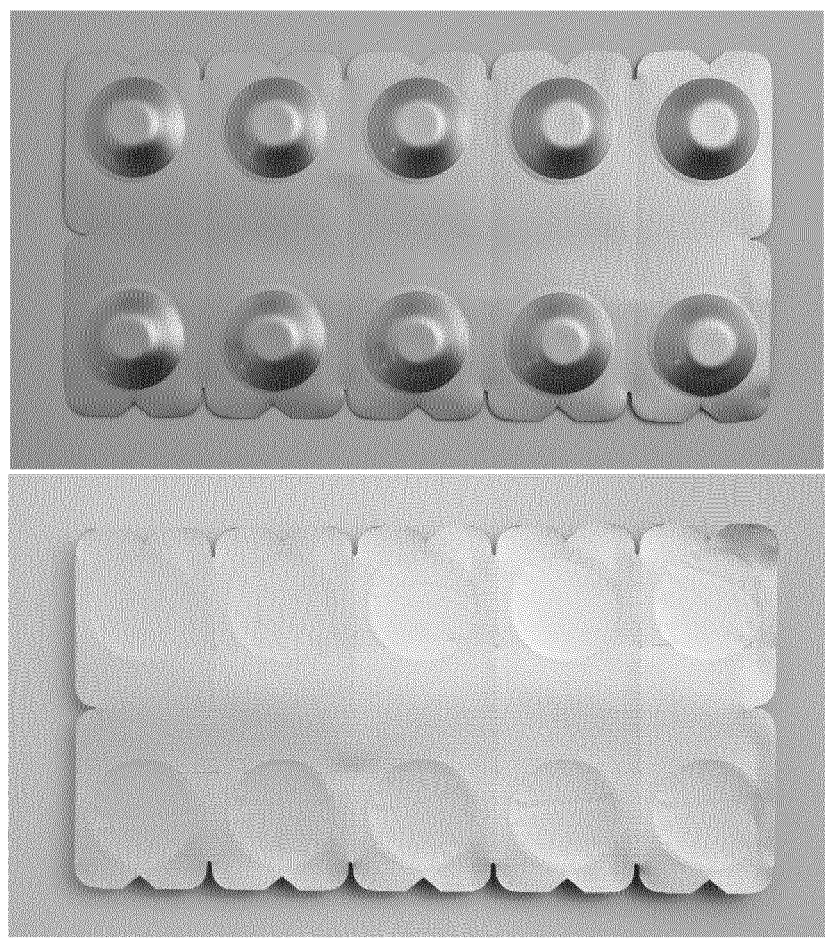
FIG. 9 is a photograph of a push-through type blister pack which has been modified to include triangular breaks (as tear notches).

The modified blister packs are shown in FIG. 9. The modification consisted of the excision of a triangular portion of the blister pack material from the outer edge adjacent to each of the blisters. The excision was achieved using a shaped punching tool.

The subjects in this study differed from those in the earlier study using the push-through blister packs (i.e. the study of Comparative Example 17).

Packaging samples were prepared, including samples containing graphic elements, to evaluate breakage of tablets and to see if patients would understand how to open the packaging. The outer dimensions 172×88 mm.

Each person was provided with 10 blister cards, each blister card containing 10 tablets (100 tablets per person in total). The tablets were identical with the orodispersible tablets of Example 7.

Test Protocol

Show the blister pack (10 tablets) with a label containing graphics (text and symbols) to the test person and say with approx. wording:

"We are doing a packaging test on ten persons to see how this packaging works. We will ask you to take out all tablets from this blister pack. You can start on any tablet of the blister pack. Before you start taking out tablets, please look at this blister pack that contains some text on one side. You will then get an identical blister pack but without any text. From that blister pack you should then take out all ten tablets. The tablets contain active ingredient, Brilinta. When you have emptied one blister pack I will put all tablets in the plastic container and then hand you another blister pack. You will take out in total 100 tablets i.e. 10 blister packs. When all tablets have been taken out I will ask you some questions."

The first blister pack with the label is then handed to the subject. This was taken back when the subject had read it. One blister pack was handed over at time. The approximate time for reading the label was noted. The method by which test persons start to take out tablets was noted (e.g. tearing, pushing or otherwise). The number of broken tablets was noted.

If a test person pushed out all tablets on the first blister pack, he/she was asked to read the label again and tearing was prompted. The test person was then expected to tear open the 9 remaining blister packs.

After the test, the test persons were asked a number of questions for scoring, including:

How easy was it to take out the tablets out of the blister pack?

Do you think this pack is easier or more difficult to open than a standard push through blister pack?

Result

The number of broken tablets was as follows:

953 tablets were removed using the tear opening method—of these, 1 tablet was broken.

47 tablets were removed using the push through method—of these, 7 tablets were broken.

The data are summarised in Table 59.

TABLE 59

Results

| Gender | Age | Started with tear or push? | No. of tablets pushed out | Broken | No. of tablets tear opened | Broken | Easy to take out by tearing | Tear easier than push out? |
|---|---|---|---|---|---|---|---|---|
| Man | 27 | Push | 10 | 3 | 90 | 0 | 5 | Tear |
| Woman | 38 | Tear | 7 | 1 | 93 | 0 | 4 | Tear |
| Man | 41 | Tear | 0 | — | 100 | 0 | 5 | Tear |
| Man | 39 | Push | 10 | 1 | 90 | 0 | 5 | Tear |
| Man | 53 | Push | 10 | 1 | 90 | 0 | 4 | Tear |
| Woman | 44 | Tear | 0 | — | 100 | 1 | 4 | Same |
| Woman | 46 | Tear | 0 | — | 100 | 0 | 4 | Tear |
| Man | 25 | Tear | 10 | 1 | 90 | 0 | 4 | Same |
| Man | 41 | Tear | 0 | — | 100 | 0 | 5 | Tear |
| Woman | 51 | Tear | 0 | — | 100 | 0 | 3 | Push |

The invention claimed is:

1. A tablet comprising:
(1S,2S,3R,5S)-3-[7-{[(1R,2S)-2-(3,4-difluorophenyl)cyclopropyl]amino}-5-(propylthio)-3H-[1,2,3]-triazolo[4,5-d]pyrimidin-3-yl]-5-(2-hydroxyethoxy)cyclo-pentane-1,2-diol; and
at least one disintegrating excipient;
wherein the tablet has a hardness of from about 50 to about 150N and a disintegration time of less than about 3 minutes.

2. The tablet according to claim 1, wherein the tablet has a disintegration time of less than about 60 seconds.

3. The tablet according to claim 1, wherein the at least one disintegrating excipient comprises a fast oral disintegrating excipient.

4. The tablet according to claim 1, wherein the at least one disintegrating excipient comprises at least one carbohydrate filler and at least one disintegrant.

5. The tablet according to claim 1, wherein the at least one disintegrating excipient comprises mannitol.

6. The tablet according to claim 1, wherein the at least one disintegrating excipient comprises crospovidone.

7. The tablet according to claim 1, wherein the at least one disintegrating excipient comprises mannitol, xylitol, anhydrous dibasic calcium phosphate, crospovidone and microcrystalline cellulose.

8. The tablet according to claim 1, wherein the at least one disintegrating excipient is a disintegrating excipient pre-mix that is present in an amount ranging from about 50% to about 80% by weight of the tablet.

9. The tablet according to claim 1, wherein the (1S,2S,3R,5S)-3-[7-{[(1R,2S)-2-(3,4-difluorophenyl)cyclopropyl]amino}-5-(propylthio)-3H-[1,2,3]-triazolo[4,5-d]pyrimidin-3-yl]-5-(2-hydroxyethoxy)cyclopentane-1,2-diol is present in an amount of from about 10 to about 18% by weight.

10. The tablet according to claim 1, wherein the tablet comprises about 60 mg or about 90 mg of (1S,2S,3R,5S)-3-[7-{[(1R,2S)-2-(3,4-difluorophenyl)cyclopropyl] amino}-5-(propylthio)-3H-[1,2,3]-triazolo[4,5-d]pyrimidin-3-yl]-5-(2-hydroxyethoxy)cyclopentane-1,2-diol.

11. The tablet according to claim 10, wherein the tablet comprises about 90 mg of (1S,2S,3R,5S)-3-[7-{[(1R,2S)-2-(3,4-difluorophenyl)cyclopropyl]amino}-5-(propylthio)-3H-[1,2,3]-triazolo[4,5-d]pyrimidin-3-yl]-5-(2-hydroxyethoxy)cyclopentane-1,2-diol.

12. The tablet according to claim 1, wherein the tablet has a hardness of from about 55 to about 90N.

13. The tablet according to claim 1, wherein the tablet further comprises at least one anti-caking agent.

14. The tablet according to claim 13, wherein the at least one anti-caking agent is present in an amount of from about 0.5 to about 1% by weight of the tablet.

15. The tablet according to claim 1, wherein the tablet is obtainable by a process comprising wet granulation of:

(1S,2S,3R,5S)-3-[7-{[(1R,2S)-2-(3,4-difluorophenyl)cyclopropyl]amino}-5-(propylthio)-3H-[1,2,3]-triazolo[4,5-d]pyrimidin-3-yl]-5-(2-hydroxyethoxy)cyclo-pentane-1,2-diol; and an anti-caking agent.

16. The tablet according to claim 9, wherein the tablet has a disintegration time of less than about 60 seconds.

17. The tablet according to claim 11, wherein the tablet has a disintegration time of less than about 60 seconds.

18. The tablet according to claim 1, wherein the tablet comprises:

(1S,2S,3R,5S)-3-[7-{[(1R,2S)-2-(3,4-difluorophenyl)cyclopropyl]amino}-5-(propylthio)-3H-[1,2,3]-triazolo[4,5-d]pyrimidin-3-yl]-5-(2-hydroxyethoxy)cyclo-pentane-1,2-diol at from about 10 to about 18% by weight of the tablet;

hydroxypropyl cellulose at from about 0.9 to about 2% by weight of the tablet;

colloidal anhydrous silica at from about 0.5 to about 1% by weight of the tablet;

mannitol at from about 47 to about 67% by weight of the tablet;

xylitol at from about 2.5 to about 4% by weight of the tablet;

anhydrous dibasic calcium phosphate at from about 2 to about 3.5% by weight of the tablet;

microcrystalline cellulose at from about 9 to about 15% by weight of the tablet;

crospovidone at from about 5 to about 9% by weight of the tablet; and sodium stearyl fumarate at from about 1 to about 2% by weight of the tablet.

19. The tablet according to claim 18, wherein the tablet has a disintegration time of less than about 60 seconds.

20. The tablet according to claim 1, wherein the (1S,2S,3R,5S)-3-[7-[(1R,2S)-2-(3,4-difluorophenyl)cyclopropyl]amino-5-(propylthio)-3H-[1,2,3]-triazolo[4, 5-d]pyrimidin-3-yl]-5-(2-hydroxyethoxy)cyclopentane-1,2-diol has a D (v, 0.9) particle size distribution of from about 5 μm to about 50 μm.

21. The tablet according to claim 1, wherein the (1S,2S,3R,5S)-3-[7-[(1R,2S)-2-(3,4-difluorophenyl)cyclopropyl]amino-5-(propylthio)-3H-[1,2,3]-triazolo[4,5-d]pyrimidin-3-yl]-5-(2-hydroxyethoxy)cyclopentane-1,2-diol is substantially present in the form of polymorph II.

22. A process for the preparation of a tablet as defined in claim 1, wherein the process comprises the step of mixing together (1S,2S,3R,5S)-3-[7-{[(1R,2S)-2-(3,4-difluorophenyl)cyclopropyl] amino}-5-(propylthio)-3H-[1,2,3]-triazolo[4,5-d]pyrimidin-3-yl]-5-(2-hydroxyethoxy)cyclopentane-1,2-diol and at least one anti-caking agent along with, or in, a liquid, so providing a wet granulate.

23. A blister pack containing one or more tablets as defined in claim 1.

24. The blister pack of claim 23, wherein the blister pack comprises a blistered base sheet comprising one or more cavities, and a lidding sheet bonded to the base sheet, wherein the edge of the blister pack comprises at least one break in the blistered base sheet and the lidding sheet such that the blister pack is tearable at the break to expose the cavity.

25. The blister pack according to claim 23, wherein the one or more tablets have a disintegration time of less than about 60 seconds.

26. The blister pack according to claim 24, wherein the one or more tablets have a disintegration time of less than about 60 seconds.

27. A method of treating atherothrombotic events in patients with cardiovascular disease, which method comprises administration of a tablet as defined in claim 1 to a patient suffering from or susceptible to such a disorder.

28. The method according to claim 27, wherein the tablet has a disintegration time of less than about 60 seconds.

* * * * *